United States Patent
Fallin et al.

(10) Patent No.: US 7,955,390 B2
(45) Date of Patent: *Jun. 7, 2011

(54) METHOD AND APPARATUS FOR SPINE JOINT REPLACEMENT

(75) Inventors: T Wade Fallin, Hyde Park, UT (US); Robert W. Hoy, Columbus, OH (US); E. Marlowe Goble, Logan, UT (US)

(73) Assignee: GME Delaware 2 LLC, Audubon, PA (US)

( * ) Notice: Subject to any disclaimer, the term of this patent is extended or adjusted under 35 U.S.C. 154(b) by 60 days.

This patent is subject to a terminal disclaimer.

(21) Appl. No.: 12/262,341

(22) Filed: Oct. 31, 2008

(65) Prior Publication Data

US 2009/0082871 A1    Mar. 26, 2009

Related U.S. Application Data

(63) Continuation of application No. 11/151,140, filed on Jun. 13, 2005, now Pat. No. 7,445,635, and a continuation of application No. 10/090,293, filed on Mar. 4, 2002, now Pat. No. 7,090,698.

(60) Provisional application No. 60/273,031, filed on Mar. 2, 2001.

(51) Int. Cl.
*A61F 2/44* (2006.01)
*A61B 17/70* (2006.01)

(52) U.S. Cl. .................... 623/17.11; 623/17.16; 606/257

(58) Field of Classification Search .... 623/17.11–17.16; 606/247, 250, 257, 263
See application file for complete search history.

(56) References Cited

U.S. PATENT DOCUMENTS

| | | | |
|---|---|---|---|
| 3,426,364 A * | 2/1969 | Lumb | |
| 3,486,505 A * | 12/1969 | Morrison | |
| 3,508,954 A | 4/1970 | White et al. | |
| 3,648,691 A | 3/1972 | Lumb et al. | |
| 3,857,642 A | 12/1974 | Miller | |
| 3,867,728 A | 2/1975 | Stubstad et al. | |
| 3,875,595 A | 4/1975 | Froning | |
| 4,003,376 A | 1/1977 | McKay | |
| 4,092,078 A | 5/1978 | Klotz et al. | |
| 4,289,123 A | 9/1981 | Dunn | |
| 4,349,921 A | 9/1982 | Kuntz | |
| 4,369,769 A | 1/1983 | Edwards | |
| 4,479,491 A | 10/1984 | Martin | |
| 4,483,334 A | 11/1984 | Murray | |
| 4,501,269 A | 2/1985 | Bagby | |
| 4,554,914 A * | 11/1985 | Kapp et al. | 606/86 A |
| 4,599,086 A | 7/1986 | Doty | |
| 4,604,995 A | 8/1986 | Stephens et al. | |
| 4,611,581 A | 9/1986 | Steffee | |
| 4,641,636 A | 2/1987 | Cotrel | |

(Continued)

FOREIGN PATENT DOCUMENTS

CN    2386790 Y    7/2000

(Continued)

OTHER PUBLICATIONS

Goh JC, et al., "Influence of PLIF cage size on lumber spine stability", Spine, Jan. 2000 25:1, PubMed abstract.

(Continued)

*Primary Examiner* — Pedro Philogene

(57) ABSTRACT

A prosthesis for the replacement of the cartilaginous structures of a spine motion segment is described. The prosthesis comprises an intervertebral disc prosthesis in combination with a facet joint prosthesis.

15 Claims, 53 Drawing Sheets

U.S. PATENT DOCUMENTS

| | | | |
|---|---|---|---|
| 4,653,481 | A | 3/1987 | Howland et al. |
| 4,657,550 | A | 4/1987 | Daher |
| 4,696,290 | A | 9/1987 | Steffee |
| 4,743,260 | A | 5/1988 | Burton |
| 4,759,769 | A | 7/1988 | Hedman et al. |
| 4,772,287 | A | 9/1988 | Ray et al. |
| 4,790,303 | A | 12/1988 | Steffee |
| 4,800,874 | A | 1/1989 | David et al. |
| 4,805,602 | A | 2/1989 | Puno et al. |
| 4,827,918 | A | 5/1989 | Olerud |
| 4,863,476 | A | 9/1989 | Shepperd |
| 4,863,477 | A | 9/1989 | Monson |
| 4,892,545 | A | 1/1990 | Day et al. |
| 4,904,260 | A | 2/1990 | Ray et al. |
| 4,911,718 | A | 3/1990 | Lee et al. |
| 4,946,458 | A | 8/1990 | Harms et al. |
| 4,955,908 | A | 9/1990 | Frey et al. |
| 5,011,484 | A | 4/1991 | Breard |
| 5,015,255 | A | 5/1991 | Kuslich |
| 5,047,055 | A | 9/1991 | Bao et al. |
| 5,071,437 | A | 12/1991 | Steffee |
| 5,092,866 | A | 3/1992 | Breard et al. |
| 5,092,867 | A | 3/1992 | Harms et al. |
| 5,092,893 | A * | 3/1992 | Smith ............... 606/290 |
| 5,127,912 | A | 7/1992 | Ray et al. |
| 5,129,900 | A | 7/1992 | Asher et al. |
| 5,147,361 | A | 9/1992 | Ojima et al. |
| 5,147,404 | A | 9/1992 | Downey |
| 5,171,279 | A | 12/1992 | Mathews |
| 5,171,280 | A | 12/1992 | Baumgartner |
| 5,180,393 | A | 1/1993 | Commarmond |
| 5,192,326 | A | 3/1993 | Bao et al. |
| 5,236,460 | A | 8/1993 | Barber |
| 5,246,458 | A | 9/1993 | Graham |
| 5,258,031 | A | 11/1993 | Salib et al. |
| 5,261,910 | A | 11/1993 | Warden et al. |
| 5,263,953 | A | 11/1993 | Bagby |
| 5,282,863 | A | 2/1994 | Burton |
| 5,304,178 | A | 4/1994 | Stahurski |
| 5,306,275 | A | 4/1994 | Bryan |
| 5,306,308 | A | 4/1994 | Gross et al. |
| 5,306,309 | A | 4/1994 | Wagner et al. |
| 5,313,962 | A | 5/1994 | Obenchain |
| 5,318,567 | A | 6/1994 | Vichard |
| 5,360,430 | A | 11/1994 | Lin |
| 5,366,455 | A | 11/1994 | Dove et al. |
| 5,370,697 | A | 12/1994 | Baumgartner |
| 5,375,823 | A | 12/1994 | Navas |
| 5,387,213 | A | 2/1995 | Breard et al. |
| 5,391,168 | A | 2/1995 | Sanders et al. |
| 5,401,269 | A | 3/1995 | Buttner-Janz et al. |
| 5,415,661 | A | 5/1995 | Holmes |
| 5,437,669 | A | 8/1995 | Yuan et al. |
| 5,437,672 | A | 8/1995 | Alleyne |
| 5,439,464 | A | 8/1995 | Shapiro |
| 5,443,516 | A | 8/1995 | Albrektsson et al. |
| 5,456,722 | A | 10/1995 | McLeod et al. |
| 5,458,641 | A | 10/1995 | Ramirez Jimenez |
| 5,458,642 | A | 10/1995 | Beer et al. |
| 5,458,643 | A | 10/1995 | Oka et al. |
| 5,464,439 | A | 11/1995 | Gendler |
| 5,470,333 | A | 11/1995 | Ray |
| 5,476,463 | A | 12/1995 | Boachie-Adjei et al. |
| 5,480,401 | A | 1/1996 | Navas |
| 5,489,308 | A | 2/1996 | Kuslich et al. |
| 5,496,318 | A | 3/1996 | Howland et al. |
| 5,507,745 | A | 4/1996 | Logroscino et al. |
| 5,507,813 | A | 4/1996 | Dowd et al. |
| 5,514,180 | A | 5/1996 | Heggeness et al. |
| 5,522,899 | A | 6/1996 | Michelson |
| 5,527,312 | A | 6/1996 | Ray |
| 5,531,745 | A | 7/1996 | Ray |
| 5,531,747 | A | 7/1996 | Ray |
| 5,534,028 | A | 7/1996 | Bao et al. |
| 5,534,030 | A | 7/1996 | Navarro et al. |
| 5,534,031 | A | 7/1996 | Matsuzaki et al. |
| 5,540,688 | A | 7/1996 | Navas |
| 5,545,166 | A | 8/1996 | Howland |
| 5,545,229 | A | 8/1996 | Parsons et al. |
| 5,549,607 | A | 8/1996 | Olson et al. |
| 5,556,431 | A | 9/1996 | Buttner-Janz |
| 5,556,687 | A | 9/1996 | McMillin |
| 5,562,735 | A | 10/1996 | Margulies |
| 5,562,736 | A | 10/1996 | Ray et al. |
| 5,562,737 | A | 10/1996 | Graf |
| 5,569,248 | A | 10/1996 | Mathews |
| 5,571,189 | A | 11/1996 | Kuslich |
| 5,571,191 | A | 11/1996 | Fitz |
| 5,572,191 | A | 11/1996 | Lundberg |
| 5,582,612 | A | 12/1996 | Lin |
| 5,584,832 | A | 12/1996 | Schlapfer |
| 5,603,713 | A | 2/1997 | Aust et al. |
| 5,609,634 | A | 3/1997 | Voydeville |
| 5,645,597 | A | 7/1997 | Krapiva |
| 5,645,599 | A * | 7/1997 | Samani ............... 623/17.16 |
| 5,649,926 | A | 7/1997 | Howland |
| 5,653,762 | A | 8/1997 | Pisharodi |
| 5,666,243 | A | 9/1997 | Brent |
| 5,672,175 | A | 9/1997 | Martin |
| 5,674,295 | A | 10/1997 | Ray et al. |
| 5,674,296 | A | 10/1997 | Bryan |
| 5,676,701 | A * | 10/1997 | Yuan et al. ............. 623/17.15 |
| 5,681,310 | A | 10/1997 | Yuan et al. |
| 5,683,464 | A | 11/1997 | Wagner et al. |
| 5,683,465 | A | 11/1997 | Shinn et al. |
| 5,688,272 | A | 11/1997 | Montague et al. |
| 5,690,629 | A | 11/1997 | Asher et al. |
| 5,702,392 | A | 12/1997 | Wu et al. |
| 5,702,450 | A | 12/1997 | Bisserie |
| 5,702,453 | A | 12/1997 | Rabbe et al. |
| 5,704,936 | A | 1/1998 | Mazel |
| 5,713,900 | A | 2/1998 | Benzel et al. |
| 5,716,415 | A | 2/1998 | Steffee |
| 5,725,582 | A | 3/1998 | Bevan et al. |
| 5,728,097 | A | 3/1998 | Mathews |
| 5,735,899 | A | 4/1998 | Schwartz et al. |
| 5,749,873 | A | 5/1998 | Fairley |
| 5,755,796 | A | 5/1998 | Ibo et al. |
| 5,772,661 | A | 6/1998 | Michelson |
| 5,797,909 | A | 8/1998 | Michelson |
| 5,814,046 | A | 9/1998 | Hopf |
| 5,824,093 | A | 10/1998 | Ray et al. |
| 5,824,094 | A | 10/1998 | Serhan et al. |
| 5,836,948 | A | 11/1998 | Zucherman et al. |
| 5,860,977 | A | 1/1999 | Zucherman et al. |
| 5,865,846 | A | 2/1999 | Bryan et al. |
| 5,868,745 | A | 2/1999 | Alleyne |
| 5,876,404 | A | 3/1999 | Zucherman et al. |
| 5,888,223 | A | 3/1999 | Bray, Jr. |
| 5,893,889 | A | 4/1999 | Harrington |
| RE36,221 | E | 6/1999 | Breard et al. |
| 5,916,267 | A | 6/1999 | Tienboon |
| 5,951,555 | A | 9/1999 | Rehak et al. |
| 5,961,516 | A | 10/1999 | Graf |
| 5,986,169 | A | 11/1999 | Gjunter |
| 6,001,130 | A | 12/1999 | Bryan et al. |
| 6,004,322 | A | 12/1999 | Bernstein |
| 6,014,588 | A | 1/2000 | Fitz |
| 6,019,759 | A | 2/2000 | Rogozinski |
| 6,019,792 | A | 2/2000 | Cauthen |
| 6,039,761 | A | 3/2000 | Li et al. |
| 6,039,763 | A | 3/2000 | Shelokov |
| 6,048,342 | A | 4/2000 | Zucherman et al. |
| 6,063,088 | A | 5/2000 | Winslow |
| 6,063,121 | A | 5/2000 | Xavier et al. |
| 6,066,325 | A | 5/2000 | Wallace et al. |
| 6,068,630 | A | 5/2000 | Zucherman et al. |
| RE36,758 | E | 6/2000 | Fitz |
| 6,074,390 | A | 6/2000 | Zucherman et al. |
| 6,080,157 | A | 6/2000 | Cathro et al. |
| 6,090,112 | A | 7/2000 | Zucherman et al. |
| 6,093,205 | A | 7/2000 | McLeod et al. |
| 6,113,637 | A | 9/2000 | Gill et al. |
| 6,113,639 | A | 9/2000 | Ray et al. |
| 6,132,464 | A * | 10/2000 | Martin ............... 623/17.15 |
| 6,132,465 | A | 10/2000 | Ray et al. |
| 6,146,421 | A | 11/2000 | Gordon et al. |

| Patent Number | Date | Inventor(s) |
|---|---|---|
| 6,149,652 A | 11/2000 | Zucherman et al. |
| 6,151,934 A | 11/2000 | Chong et al. |
| 6,152,926 A | 11/2000 | Zucherman et al. |
| 6,156,038 A | 12/2000 | Zucherman et al. |
| 6,156,067 A | 12/2000 | Bryan et al. |
| 6,176,861 B1 | 1/2001 | Bernstein et al. |
| 6,179,838 B1 | 1/2001 | Fiz |
| 6,183,471 B1 | 2/2001 | Zucherman et al. |
| 6,190,387 B1 | 2/2001 | Zucherman et al. |
| 6,190,414 B1 | 2/2001 | Young et al. |
| 6,206,882 B1 | 3/2001 | Cohen |
| 6,206,922 B1 | 3/2001 | Zdeblick et al. |
| 6,228,118 B1 | 5/2001 | Gordon |
| 6,235,030 B1 | 5/2001 | Zucherman et al. |
| 6,238,397 B1 | 5/2001 | Zucherman et al. |
| 6,241,730 B1 | 6/2001 | Alby |
| 6,264,655 B1 | 7/2001 | Pisharodi |
| 6,267,764 B1 | 7/2001 | Elberg |
| 6,280,444 B1 | 8/2001 | Zucherman et al. |
| 6,290,700 B1 | 9/2001 | Schmotzer |
| 6,293,949 B1 | 9/2001 | Justis et al. |
| 6,312,469 B1 | 11/2001 | Gielen et al. |
| 6,314,325 B1 | 11/2001 | Fitz |
| 6,332,882 B1 | 12/2001 | Zucherman et al. |
| 6,332,883 B1 | 12/2001 | Zucherman et al. |
| 6,379,355 B1 | 4/2002 | Zucherman et al. |
| 6,402,750 B1 | 6/2002 | Atkinson et al. |
| 6,413,259 B1 | 7/2002 | Lyons et al. |
| 6,419,676 B1 | 7/2002 | Zucherman et al. |
| 6,419,677 B2 | 7/2002 | Zucherman et al. |
| 6,419,703 B1 | 7/2002 | Fallin et al. |
| 6,419,704 B1 | 7/2002 | Ferree |
| 6,440,168 B1 * | 8/2002 | Cauthen ............... 623/17.14 |
| 6,440,169 B1 | 8/2002 | Elberg et al. |
| 6,447,546 B1 | 9/2002 | Bramlet et al. |
| 6,451,019 B1 | 9/2002 | Zucherman et al. |
| 6,451,020 B1 | 9/2002 | Zucherman et al. |
| 6,458,131 B1 | 10/2002 | Ray |
| 6,461,359 B1 | 10/2002 | Tribus et al. |
| 6,471,704 B2 | 10/2002 | Gertzbein et al. |
| 6,475,219 B1 | 11/2002 | Shelokov |
| 6,478,796 B2 | 11/2002 | Zucherman et al. |
| 6,481,440 B2 | 11/2002 | Gielen et al. |
| 6,485,518 B1 | 11/2002 | Cornwall et al. |
| 6,500,178 B2 | 12/2002 | Zucherman et al. |
| 6,514,256 B2 | 2/2003 | Zucherman et al. |
| 6,527,806 B2 | 3/2003 | Ralph et al. |
| 6,540,747 B1 | 4/2003 | Marino |
| 6,540,785 B1 * | 4/2003 | Gill et al. ............... 623/17.14 |
| 6,565,605 B2 | 5/2003 | Goble et al. |
| 6,579,319 B2 | 6/2003 | Goble et al. |
| 6,582,433 B2 | 6/2003 | Yun |
| 6,585,769 B2 | 7/2003 | Muhanna et al. |
| 6,610,091 B1 * | 8/2003 | Reiley ............... 623/17.11 |
| 6,616,669 B2 | 9/2003 | Ogilvie et al. |
| 6,626,909 B2 | 9/2003 | Chin |
| 6,626,944 B1 | 9/2003 | Taylor |
| 6,652,527 B2 | 11/2003 | Zucherman et al. |
| 6,652,534 B2 | 11/2003 | Zucherman et al. |
| 6,652,585 B2 | 11/2003 | Lange |
| 6,669,729 B2 | 12/2003 | Chin |
| 6,695,842 B2 | 2/2004 | Zucherman et al. |
| 6,699,246 B2 | 3/2004 | Zucherman et al. |
| 6,699,247 B2 | 3/2004 | Zucherman et al. |
| 6,733,534 B2 | 5/2004 | Sherman |
| 6,761,719 B2 | 7/2004 | Justis et al. |
| 6,761,720 B1 | 7/2004 | Senegas |
| 6,783,527 B2 | 8/2004 | Drewry et al. |
| 6,796,983 B1 | 9/2004 | Zucherman et al. |
| 6,811,567 B2 | 11/2004 | Reiley |
| 6,835,205 B2 | 12/2004 | Atkinson et al. |
| 6,835,207 B2 | 12/2004 | Zacouto et al. |
| 7,090,698 B2 * | 8/2006 | Goble et al. ............... 623/17.11 |
| 7,445,635 B2 * | 11/2008 | Fallin et al. ............... 623/17.11 |
| 2001/0007073 A1 | 7/2001 | Zucherman et al. |
| 2001/0012938 A1 | 8/2001 | Zucherman et al. |
| 2001/0016743 A1 | 8/2001 | Zucherman et al. |
| 2001/0021850 A1 | 9/2001 | Zucherman et al. |
| 2001/0031965 A1 | 10/2001 | Zucherman et al. |
| 2001/0039452 A1 | 11/2001 | Zucherman et al. |
| 2002/0029039 A1 | 3/2002 | Zucherman et al. |
| 2002/0065557 A1 | 5/2002 | Goble et al. |
| 2002/0072800 A1 | 6/2002 | Goble et al. |
| 2002/0091446 A1 | 7/2002 | Zucherman et al. |
| 2002/0099384 A1 | 7/2002 | Scribner et al. |
| 2002/0116000 A1 | 8/2002 | Zucherman et al. |
| 2002/0123806 A1 | 9/2002 | Reiley |
| 2002/0143331 A1 | 10/2002 | Zucherman et al. |
| 2002/0151895 A1 | 10/2002 | Soboleski et al. |
| 2002/0183746 A1 | 12/2002 | Zucherman et al. |
| 2003/0004572 A1 | 1/2003 | Goble et al. |
| 2003/0009226 A1 | 1/2003 | Graf |
| 2003/0028250 A1 | 2/2003 | Reiley et al. |
| 2003/0040797 A1 | 2/2003 | Fallin et al. |
| 2003/0055427 A1 | 3/2003 | Graf |
| 2003/0065330 A1 | 4/2003 | Zucherman et al. |
| 2003/0073998 A1 | 4/2003 | Pagliuca et al. |
| 2003/0109880 A1 | 6/2003 | Shirado et al. |
| 2003/0153912 A1 | 8/2003 | Graf |
| 2003/0191470 A1 | 10/2003 | Ritland |
| 2003/0220642 A1 | 11/2003 | Freudiger |
| 2003/0220643 A1 | 11/2003 | Ferree |
| 2004/0006341 A1 | 1/2004 | Shaolian et al. |
| 2004/0006391 A1 | 1/2004 | Reiley |
| 2004/0024458 A1 | 2/2004 | Senegas et al. |
| 2004/0049189 A1 | 3/2004 | Le Couedic et al. |
| 2004/0049190 A1 | 3/2004 | Biedermann et al. |
| 2004/0049272 A1 | 3/2004 | Reiley |
| 2004/0049273 A1 | 3/2004 | Reiley |
| 2004/0049274 A1 | 3/2004 | Reiley |
| 2004/0049275 A1 | 3/2004 | Reiley |
| 2004/0049276 A1 | 3/2004 | Reiley |
| 2004/0049277 A1 | 3/2004 | Reiley |
| 2004/0049278 A1 | 3/2004 | Reiley |
| 2004/0049281 A1 | 3/2004 | Reiley |
| 2004/0073215 A1 | 4/2004 | Carli |
| 2004/0078082 A1 | 4/2004 | Lange |
| 2004/0082954 A1 | 4/2004 | Teitelbaum et al. |
| 2004/0087950 A1 | 5/2004 | Teitelbaum |
| 2004/0106995 A1 | 6/2004 | Le Couedic et al. |
| 2004/0111154 A1 | 6/2004 | Reiley |
| 2004/0116927 A1 | 6/2004 | Graf |
| 2004/0117017 A1 | 6/2004 | Pasquet et al. |
| 2004/0127989 A1 | 7/2004 | Dooris et al. |
| 2004/0143264 A1 | 7/2004 | McAfee |
| 2004/0147928 A1 | 7/2004 | Landry et al. |
| 2004/0153071 A1 | 8/2004 | Zucherman et al. |
| 2004/0158245 A1 | 8/2004 | Chin |
| 2004/0167520 A1 | 8/2004 | Zucherman et al. |
| 2004/0172025 A1 | 9/2004 | Drewry et al. |
| 2004/0181282 A1 | 9/2004 | Zucherman et al. |
| 2004/0181285 A1 | 9/2004 | Simonson |
| 2004/0186475 A1 | 9/2004 | Falahee |
| 2004/0220568 A1 | 11/2004 | Zucherman et al. |
| 2004/0225289 A1 | 11/2004 | Biedermann et al. |
| 2004/0230192 A1 | 11/2004 | Graf |
| 2004/0230201 A1 | 11/2004 | Yuan et al. |
| 2004/0230304 A1 | 11/2004 | Yuan et al. |
| 2004/0236327 A1 | 11/2004 | Paul et al. |
| 2004/0236328 A1 | 11/2004 | Paul et al. |
| 2004/0236329 A1 | 11/2004 | Panjabi |
| 2004/0243239 A1 | 12/2004 | Taylor |
| 2005/0010291 A1 | 1/2005 | Stinson et al. |
| 2005/0010293 A1 | 1/2005 | Zucherman et al. |
| 2005/0010298 A1 | 1/2005 | Zucherman et al. |
| 2005/0027361 A1 * | 2/2005 | Reiley |
| 2005/0033434 A1 * | 2/2005 | Berry |
| 2005/0033439 A1 * | 2/2005 | Gordon et al. |
| 2005/0043797 A1 * | 2/2005 | Lee |
| 2005/0043799 A1 * | 2/2005 | Reiley |
| 2005/0113927 A1 | 5/2005 | Malek |
| 2005/0119748 A1 * | 6/2005 | Reiley et al. |
| 2005/0131406 A1 * | 6/2005 | Reiley et al. |
| 2005/0137705 A1 * | 6/2005 | Reiley |
| 2005/0137706 A1 * | 6/2005 | Reiley |
| 2005/0143818 A1 * | 6/2005 | Yuan et al. |
| 2005/0149190 A1 * | 7/2005 | Reiley |
| 2005/0154467 A1 * | 7/2005 | Peterman et al. |

FOREIGN PATENT DOCUMENTS

| | | |
|---|---|---|
| EP | 408489 A1 | 1/1991 |
| EP | 322334 B1 | 2/1992 |
| EP | 667127 A1 | 8/1995 |
| EP | 767637 B1 | 11/1998 |
| EP | 768843 B1 | 2/1999 |
| EP | 669109 B1 | 5/1999 |
| EP | 1239785 B1 | 9/2004 |
| EP | 1343424 B1 | 9/2004 |
| EP | 1399078 B1 | 12/2004 |
| FR | 2721501 B1 | 8/1996 |
| JP | 10179622 A2 | 7/1998 |
| JP | 10277070 A2 | 10/1998 |
| SU | 1468543 A1 | 3/1989 |
| SU | 1517953 A1 | 10/1989 |
| WO | WO8707827 A1 | 12/1987 |
| WO | WO9421185 A1 | 9/1994 |
| WO | WO9505783 A1 | 3/1995 |
| WO | WO9505784 A1 | 3/1995 |
| WO | WO9505785 A1 | 3/1995 |
| WO | WO9505786 A1 | 3/1995 |
| WO | WO9600049 A1 | 1/1996 |
| WO | WO9822033 A1 | 5/1998 |
| WO | WO9848707 A1 | 11/1998 |
| WO | WO9848717 A1 | 11/1998 |
| WO | WO9856301 A1 | 12/1998 |
| WO | WO9905995 A1 | 2/1999 |
| WO | WO9921500 A1 | 5/1999 |
| WO | WO9921501 A1 | 5/1999 |
| WO | WO9923963 A1 | 5/1999 |
| WO | WO9965412 A1 | 12/1999 |
| WO | WO9960957 C2 | 5/2000 |
| WO | WO0038582 | 7/2000 |
| WO | WO0062684 A1 | 10/2000 |
| WO | WO0130248 A1 | 5/2001 |
| WO | WO0145576 A1 | 6/2001 |
| WO | WO0149192 A1 | 7/2001 |
| WO | WO0156489 A1 | 8/2001 |
| WO | WO0164142 A1 | 9/2001 |
| WO | WO0164144 A2 | 9/2001 |
| WO | WO0191657 A1 | 12/2001 |
| WO | WO0191658 A1 | 12/2001 |
| WO | WO0197721 A2 | 12/2001 |
| WO | WO0200124 A1 | 1/2002 |
| WO | WO0203882 A2 | 1/2002 |
| WO | WO0207621 A1 | 1/2002 |
| WO | WO0207622 A1 | 1/2002 |
| WO | WO0207623 A1 | 1/2002 |
| WO | WO0213732 A3 | 2/2002 |
| WO | WO0230336 A2 | 4/2002 |
| WO | WO0234120 A2 | 5/2002 |
| WO | WO0243603 A1 | 6/2002 |
| WO | WO02067792 A2 | 9/2002 |
| WO | WO02067793 A2 | 9/2002 |
| WO | WO02089712 A1 | 11/2002 |
| WO | WO02102259 A2 | 12/2002 |
| WO | WO03009737 A1 | 2/2003 |
| WO | WO03011147 A1 | 2/2003 |
| WO | WO03015646 A2 | 2/2003 |
| WO | WO03045262 A2 | 6/2003 |
| WO | WO03077806 A1 | 9/2003 |
| WO | WO2004017817 A2 | 3/2004 |
| WO | WO2004019762 A2 | 3/2004 |
| WO | WO2004024010 A1 | 3/2004 |
| WO | WO2004032794 A2 | 4/2004 |
| WO | WO2004039239 A2 | 5/2004 |
| WO | WO2004039243 A2 | 5/2004 |
| WO | WO2004041066 A2 | 5/2004 |
| WO | WO2004073533 A1 | 9/2004 |
| WO | WO2004098423 A1 | 11/2004 |
| WO | WO2004098452 A2 | 11/2004 |
| WO | WO2004105577 A2 | 12/2004 |
| WO | WO2004105580 A2 | 12/2004 |
| WO | WO2005013864 | 2/2005 |
| WO | WO2005037149 | 4/2005 |
| WO | WO2005044152 A1 | 5/2005 |

OTHER PUBLICATIONS

Head WC, Wagner surface replacement arthroplasty of the hip. Analysis of fourteen failures in forty-one hips:, J Bone Joint Surg. [Am], Mar. 1981 63:3, PubMed Abstract.

Kotani Y, et al., "The effects of spinal fixation and destabilization on the biomechanical and histologic properties of spinal ligaments. An in vivo study.", Spine Mar. 15, 1998 23:6, PubMed abstract.

Lemaire JP, et al., "Intervertebral Disc Prothesis: Results and Prospects for the Year 2000", Clinical Orthopaedics and Related Research, PubMed abstract.

Nagata H, et al., "The effects of immobilization of long segments of the spine on the adjacent and distal facet force and lumbrosacral motion", Spine, Dec. 1993 18:16. PubMed abstract.

Nibu K, et al., Multidirectional stabilizing potential of BAK interbody spinal fusion system for anterior surgery, J Spinal Discord, Aug. 1997 10:4, PubMed abstract.

Tsantrizos A, et al., "Segmental stability and compressive strength of posterior lumbar interbody fusion implants", Spine, Aug. 1, 2000 25:15, PubMed abstract.

Todd Anres; *Facet Joint Arthroplasty: A Glimpse of the Future of Spine Technology*, Othopaedic Product News, Sep./Oct. 2005 p. 38-40.

\* cited by examiner

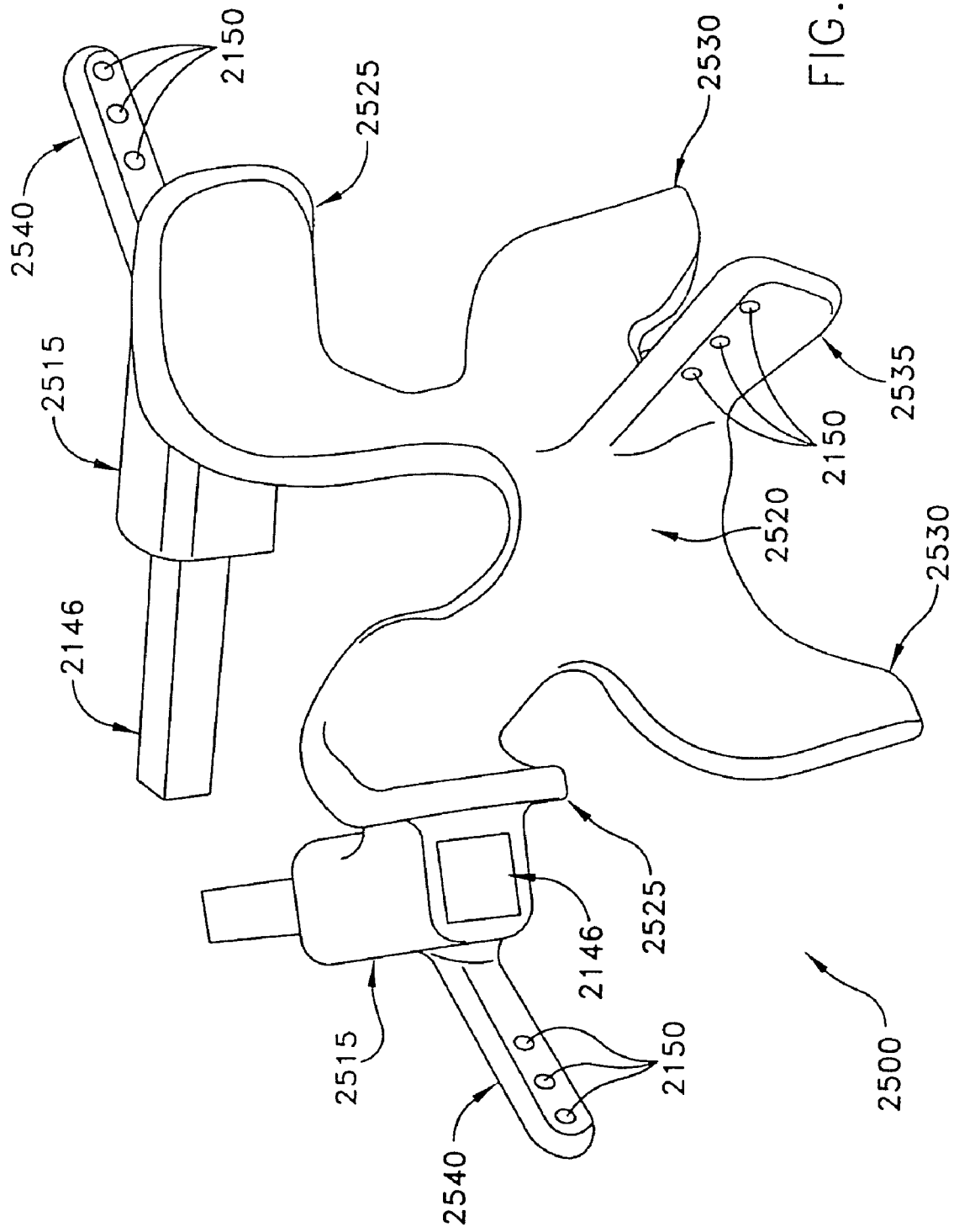

METHOD AND APPARATUS FOR SPINE JOINT REPLACEMENT

CROSS-REFERENCE TO RELATED APPLICATIONS

This application is a continuation of:

U.S. application Ser. No. 11/151,140, filed Jun. 13, 2005 and entitled METHOD AND APPARATUS FOR SPINE JOINT REPLACEMENT, issued U.S. Pat. No. 7,445,635, Which is a continuation of:

U.S. application Ser. No. 10/090,293, filed Mar. 4, 2002 and entitled METHOD AND APPARATUS FOR SPINE JOINT REPLACEMENT, issued U.S. Pat. No. 7,090,698, Which claims the benefit of:

U.S. Application Ser. No. 60/273,031, filed Mar. 2, 2001 and entitled TOTAL SPINE JOINT REPLACEMENT;

The disclosures listed above are incorporated herein by reference.

BACKGROUND OF THE INVENTION

The Field of the Invention

Traumatic, inflammatory, metabolic, synovial, neoplastic and degenerative disorders of the spine can produce debilitating pain that can have severe socioeconomic and psychological effects.

One of the most common surgical interventions today is arthrodesis, or spine fusion, in which two or more adjacent vertebral bodies are fused together in order to alleviate pain associated with the disc(s) located between those vertebral bodies. Approximately 300,000 such procedures are performed annually in the United States alone. Clinical success varies considerably, depending upon technique and indications, and consideration must be given to the concomitant risks and complications.

For example, while spine fusion generally helps to eliminate certain types of pain, it has also been shown to decrease function by limiting the range of motion for patients in flexion, extension, axial rotation and lateral bending. Furthermore, it is believed that spine fusion creates increased stresses on (and, therefore, accelerated degeneration of) adjacent non-fused motion segments. Additionally, pseudoarthrosis, resulting from an incomplete or ineffective fusion, may reduce or even totally eliminate the desired pain relief for the patient. Also, the fusion device(s) used to effect fusion, whether artificial or biological, may migrate out of the fusion site, thereby creating significant new problems for the patient.

Recently, attempts have been made to recreate the natural biomechanics of the spine through the use of an artificial disc. Artificial discs are intended to restore articulation between vertebral bodies so as to recreate the full range of motion normally allowed by the elastic properties of the natural disc, which directly connects two opposing vertebral bodies. Various artificial discs are described by Stefee et al. in U.S. Pat. No. 5,071,437; Gill et al. in U.S. Pat. No. 6,113,637; Bryan et al. in U.S. Pat. No. 6,001,130; Hedman et al. in U.S. Pat. No. 4,759,769; Ray in U.S. Pat. No. 5,527,312; Ray et al. in U.S. Pat. No. 5,824,093; Buttner-Janz in U.S. Pat. No. 5,401,269; and Serhan et al. in U.S. Pat. No. 5,824,094; all of which documents are hereby incorporated herein by reference. Still other artificial discs are known in the art.

Unfortunately, however, artificial discs alone do not adequately address all of the mechanics of the motion of the spinal column.

In addition to the intervertebral disc, posterior elements called the facet joints help to support axial, torsional and shear loads that act on the spinal column. Furthermore, the facet joints are diarthroidal joints that provide both sliding articulation and load transmission features. However, the facet joints can also be a significant source of spinal disorders and, in many cases, debilitating pain. For example, a patient may suffer from arthritic facet joints, severe facet joint tropism or otherwise deformed facet joints, facet joint injuries, etc. There is currently a lack of good interventions for facet joint disorders. Facetectomy, or the removal of the facet joints, may provide some relief, but it is also believed to produce significant decreases in the stiffness of the spinal column (i.e., hypermobility) in all planes of motion: flexion and extension, lateral bending, and axial rotation. Furthermore, problems with the facet joints can also complicate treatments associated with other portions of the spine. By way of example, contraindications for artificial discs include arthritic facet joints, absent facet joints, severe facet joint tropism or otherwise deformed facet joints.

A superior vertebra with its inferior facets, an inferior vertebra with its superior facets, the intervertebral disc, and seven spinal ligaments together comprise a spinal motion segment or functional spine unit. The spinal motion segment provides complex motion along three orthogonal axes, both in rotation (lateral bending, flexion and extension, and axial rotation) and in translation (anterior-posterior, medial-lateral, and cranial-caudal). Furthermore, the spinal motion segment provides physiological limits and stiffnesses in each rotational and translational direction to create a stable and strong column structure to support physiological loads.

As mentioned above, compromised facet joints are a contraindication for disc replacement, due to the inability of the artificial disc (when used with compromised facet joints, or when used with missing facet joints) to properly restore the natural biomechanics of the spinal motion segment. It would therefore be an improvement in the art to provide a spine implant system that facilitates concurrent replacement of the intervertebral disc and facet joints where both have been compromised due to disease or trauma.

U.S. Pat. No. Re. 36,758 (Fitz) discloses an artificial facet joint where the inferior facet, the mating superior facet, or both, are covered with a cap. This cap requires no preparation of the bone or articular surfaces; it covers, and therefore preserves, the bony and articular structure. The capping of the facet has several potential disadvantages, however. If the facet joint is osteoarthritic, a cap will not remove the source of the pain. Additionally, at least in the case of surface replacements for osteoarthritic femoral heads, the capping of articular bone ends has proven to lead to clinical failure by means of mechanical loosening. This clinical failure is hypothesized to be a sequela of disrupting the periosteum and ligamentum teres femoris, both serving a nutrition delivery role to the femoral head, thereby leading to avascular necrosis of the bony support structure for the surface replacement. It is possible that corresponding problems could develop from capping the facet. Another potential disadvantage of facet capping is that in order to accommodate the wide variability in anatomical morphology of the facets, not only between individuals but also between levels within the spinal column, a very wide range of cap sizes and shapes is required.

U.S. Pat. No. 6,132,464 (Martin) discloses a spinal facet joint prosthesis that is supported on the lamina (which is sometimes also referred to as the posterior arch). Extending from this support structure are inferior and/or superior blades that replace the cartilage at the facet joint. Like the design of the aforementioned U.S. Pat. No. Re. 36,758, the prosthesis of U.S. Pat. No. 6,132,464 generally preserves existing bony structures and therefore does not address pathologies which affect the bone of the facets in addition to affecting the associated cartilage. Furthermore, the prosthesis of U.S. Pat. No. 6,132,464 requires a secure mating between the prosthesis and the lamina. However, the lamina is a very complex and highly variable anatomical surface. As a result, in practice, it is very difficult to design a prosthesis that provides reproducible positioning against the lamina so as to correctly locate the cartilage-replacing blades for the facet joints.

Another approach to surgical intervention for spinal facets is disclosed in International Patent Publication No. WO9848717A1 (Villaret et al.). While this publication teaches the replacement of spinal facets, the replacement is interlocked in a manner so as to immobilize the joint.

Thus it will be seen that previous attempts to provide facet joint replacement have proven inadequate.

SUMMARY OF THE INVENTION

One object of the present invention to provide a spine joint reconstruction assembly that replaces the intervertebral disc and one or more of the facet joints in order to restore the natural biomechanics of a spinal motion segment.

Another object of the present invention is to provide a method for reconstructing the spine joint by replacing the intervertebral disc and one or more of the facet joints in order to restore the natural biomechanics of a spinal motion segment.

Still another object of the present invention is to provide a kit for the reconstruction of multiple spine joints to replace intervertebral discs and facet joints in order to restore the natural biomechanics of a spinal motion segment.

In accordance with the present invention, the preferred embodiment, the intervertebral disc is excised and replaced with an artificial disc. This artificial disc may be a device such as is described by Stefee et al. in U.S. Pat. No. 5,071,437; Gill et al. in U.S. Pat. No. 6,113,637; Bryan No. 5,527,312; Ray et al. in U.S. Pat. No. 5,824,093; Buttner-Janz in U.S. Pat. No. 5,401,269; and Serhan et al. in U.S. Pat. No. 5,824,094; all which documents are hereby incorporated herein by reference. Alternatively, the artificial disc may be some other artificial disc of the sort known in the art.

In addition to replacing the intervertebral disc, at least one of the facet joints is replaced in accordance with the apparatus and methods described hereinafter. Alternatively, the facet joints may be replaced as described by Fitz in U.S. Pat. No. Re. 36,758; Martin in U.S. Pat. No. 6,132,464; and/or Villaret et al. in International Patent Publication No. WO 9848717A1, which documents are hereby incorporated herein by reference. Or one or more of the facet joints may be replaced by other apparatus and methods known in the art.

The present invention has several advantages over the prior art. For one thing, the present invention can provide a complete replacement of all of the articulation surfaces of a spine motion segment: the intervertebral disc and the facet joints. Proper disc height is restored while degenerated facet joints and the underlying painful bone is replaced. The prosthetic disc and prosthetic facet joints work together to reproduce the desired physiological range of motion and to provide low friction articulations, so that adjacent motion segments are returned to physiological levels of stress and strain. Furthermore, osteophytic growth can be concurrently removed, and the artificial disc and facet joint prosthesis together reestablish intervertebral and central foraminal spaces to ensure decompression of any nerve structure. Thus, all sources of pain, such as pain associated with osteoarthritis, instability, and nerve compression, are removed while restoring full function of the spine motion segment.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like parts and further wherein:

FIG. 53 is a perspective view showing an alternative arrangement for mounting the prosthesis of FIG. 45 to a vertebra.

DETAILED DESCRIPTION OF THE PREFERRED EMBODIMENTS

Disc Prosthesis and Single Facet Prosthesis

Figure 3:
FIG. 3 is a lateral view of a spine joint reconstructed in accordance with one aspect of the present invention.

Referring now to FIG. 3, in accordance with one aspect of the present invention, the intervertebral disc 2 has been replaced by an artificial disc AD. Artificial disc AD comprises opposing end plates 2900, 2901 and an articulating structure 2902 disposed between the end plates 2900, 2901. The articulating structure 2902 comprises a rounded recess 2903 in end plate 2900 and a rounded protrusion 2904 extending from end plate 2901. The artificial disc AD is described in further detail in U.S. Pat. No. 4,759,769. This artificial disc AD may be a device such as is described by Stefee et al. in U.S. Pat. No. 5,071,437; Gill et al. in U.S. Pat. No. 6,113,637; Bryan et al. in U.S. Pat. No. 6,001,130; Hedman et al. in U.S. Pat. No. 4,759,769; Ray in U.S. Pat. No. 5,527,312; Ray et al. in U.S. Pat. No. 5,824,093; Buttner-Janz in U.S. Pat. No. 5,401,269; and Serhan et al. in U.S. Pat. No. 5,824,094; all which documents are hereby incorporated herein by reference. Alternatively, the artificial disc may be some other artificial disc of the sort known in the art.

Referring now to FIG. 3, in accordance with one aspect of the present invention, the intervertebral disc 2 has been replaced by an artificial disc AD. This artificial disc AD may be a device such as is described by Stefee et al. in U.S. Pat. No. 5,071,437; Gill et al. in U.S. Pat. No. 6,113,637; Bryan et al. in U.S. Pat. No. 6,001,130; Hedman et al. in U.S. Pat. No. 4,759,769; Ray in U.S. Pat. No. 5,527,312; Ray et al. in U.S. Pat. No. 5,824,093; Buttner-Janz in U.S. Pat. No. 5,401,269; and Serhan et al. in U.S. Pat. No. 5,824,094; all which documents are hereby incorporated herein by reference. Alternatively, the artificial disc may be some other artificial disc of the sort known in the art.

In addition to the foregoing, the left inferior facet 6 of vertebra 1 has been resected and an inferior facet prosthesis 4 has been attached to vertebra 1. Similarly, the left superior facet 7 of vertebra 3 has been resected and a superior facet prosthesis 5 has been attached to vertebra 3.

Figure 4:
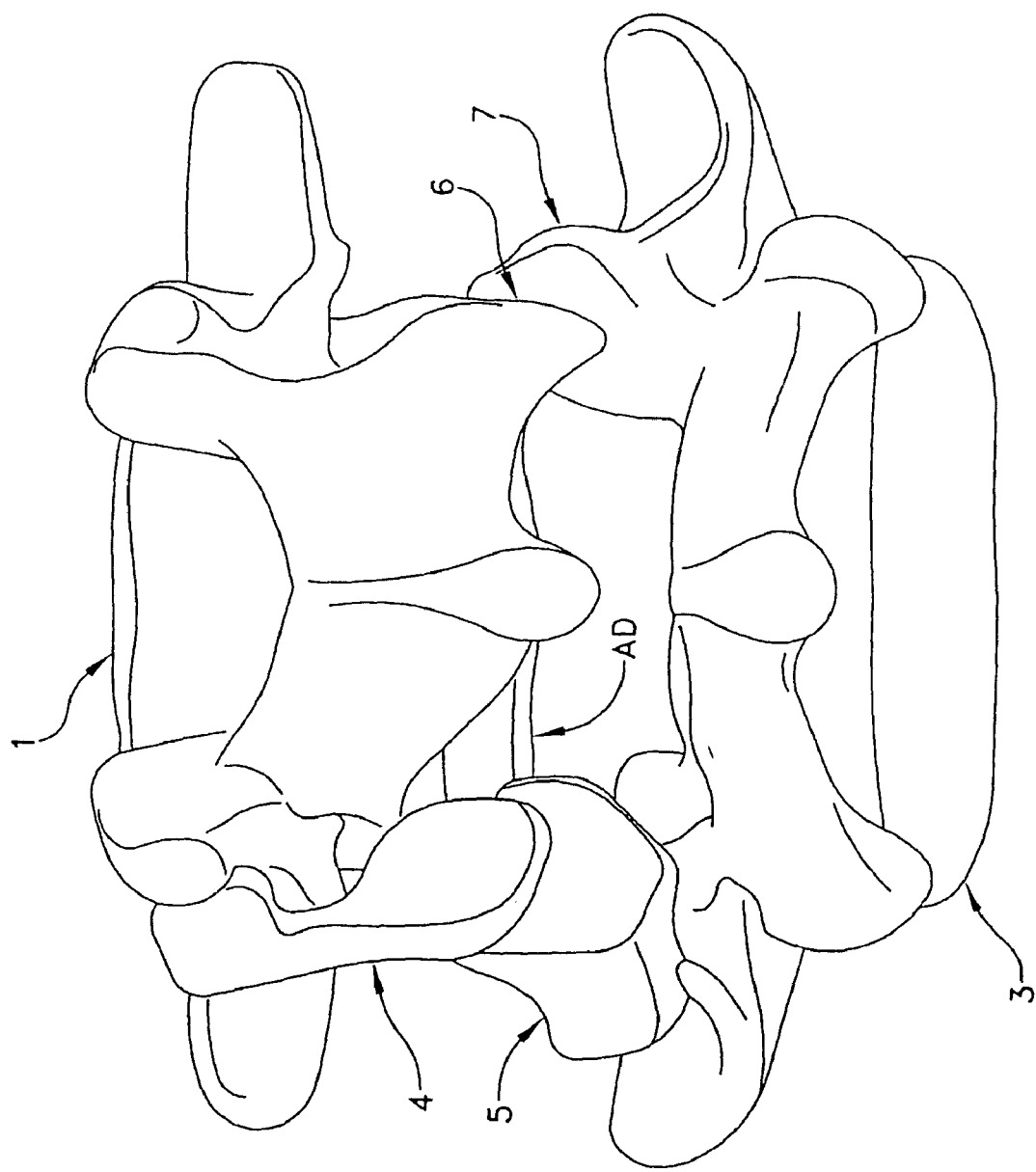
FIG. 4 is a dorsal view of the facet joint shown in FIG. 3.

FIG. 4 illustrates a dorsal view of the elements shown in FIG. 3. It can be appreciated that inferior facet prosthesis 4 replicates the natural anatomy when compared to the contralateral inferior facet 6 of vertebra 1. Similarly, it can be appreciated that superior facet prosthesis 5 replicates the natural anatomy when compared to the contralateral superior facet 7 of vertebra 3.

Figure 5:
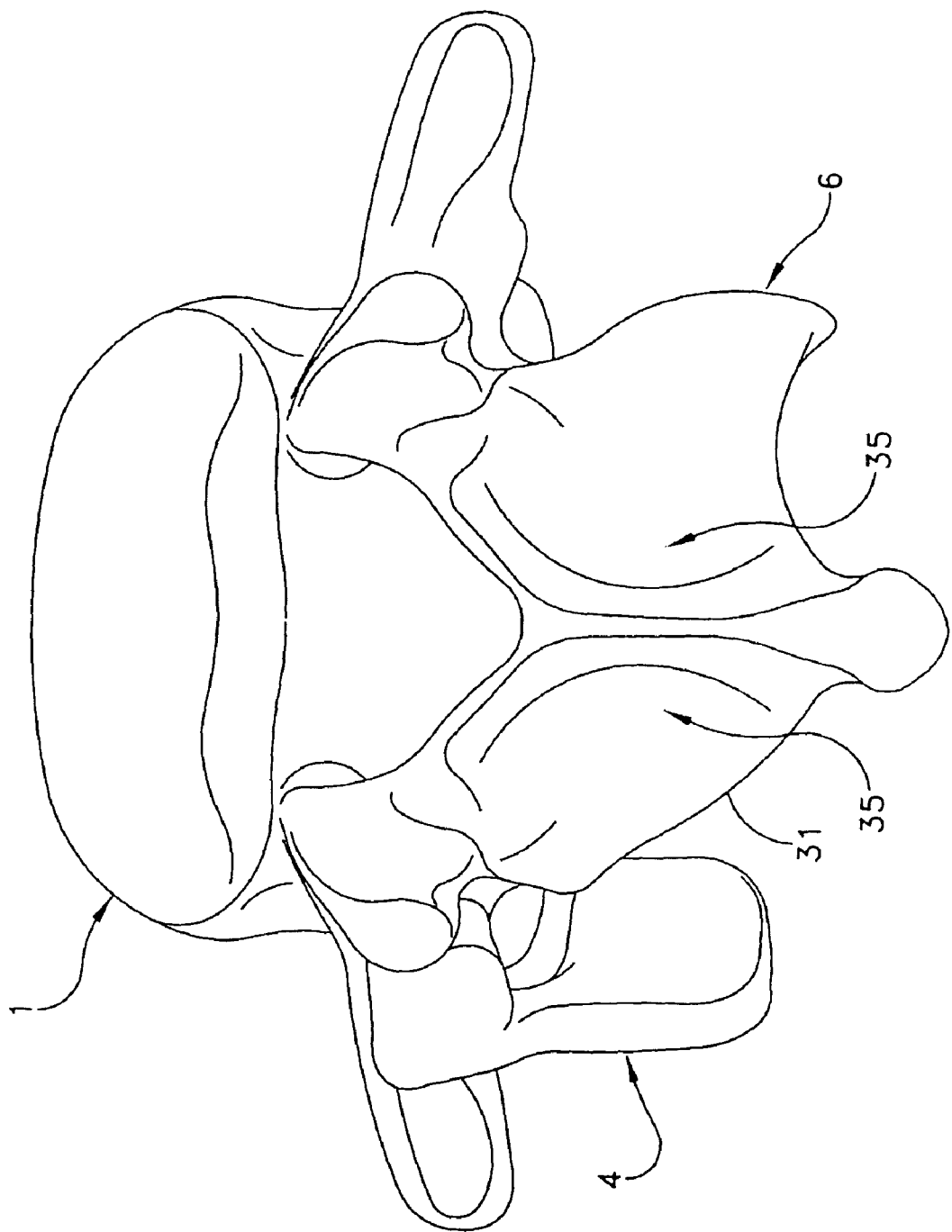
FIG. 5 is a perspective view of the implanted left inferior facet prosthesis shown in FIGS. 3 and 4.

Turning now to FIG. 5, a perspective view of vertebra 1 with implanted inferior facet prosthesis 4 is provided. Resection at 31 has removed the natural inferior facet 6 at the bony junction between the inferior facet 6 and the posterior arch 35. In this manner, bone pain associated with a disease, such as osteoarthritis, or trauma may be eliminated as the involved bony tissue has been osteotomized.

Figure 1:
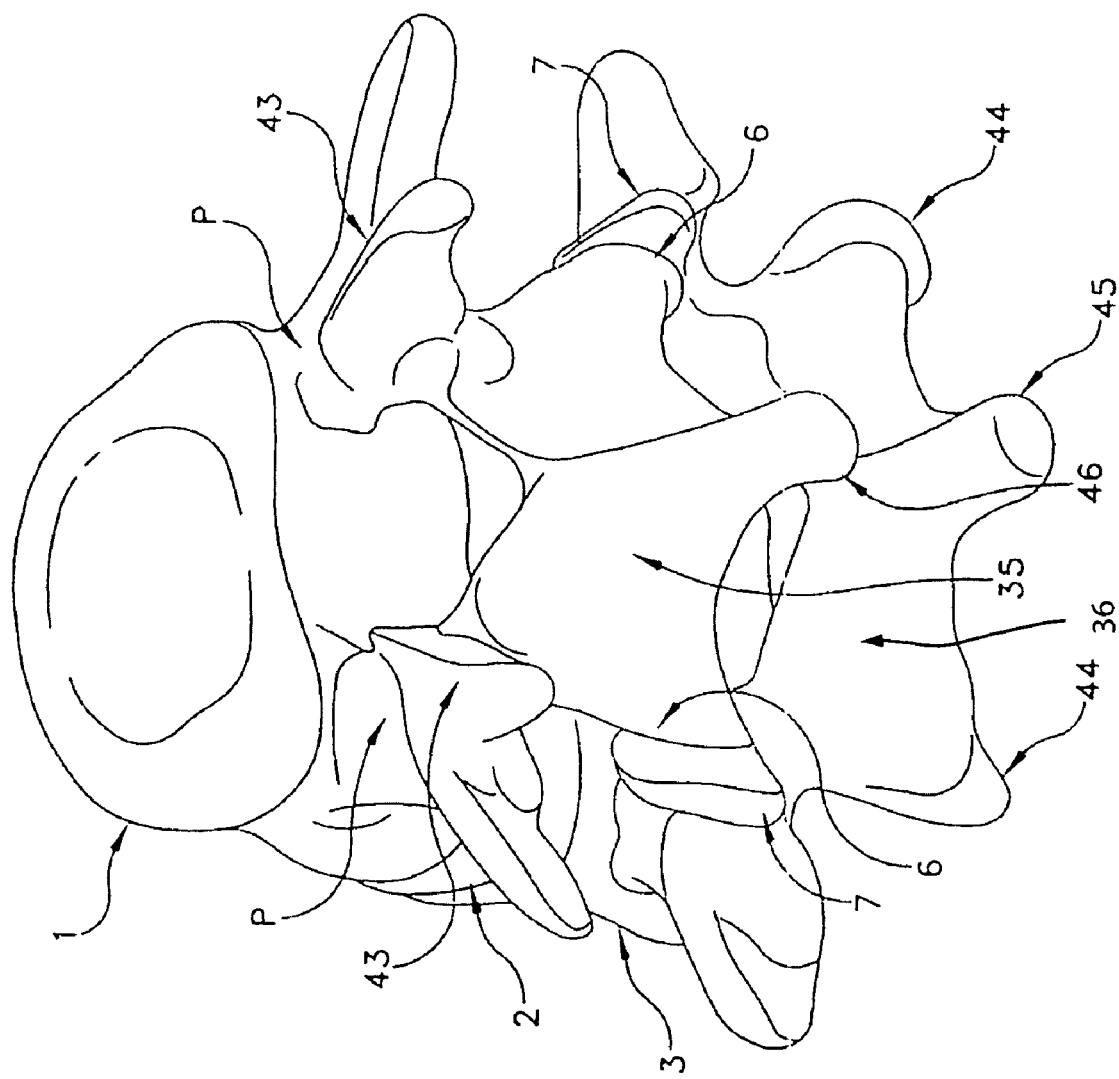
FIG. 1 is a perspective view of a portion of the spine.
Figure 2:
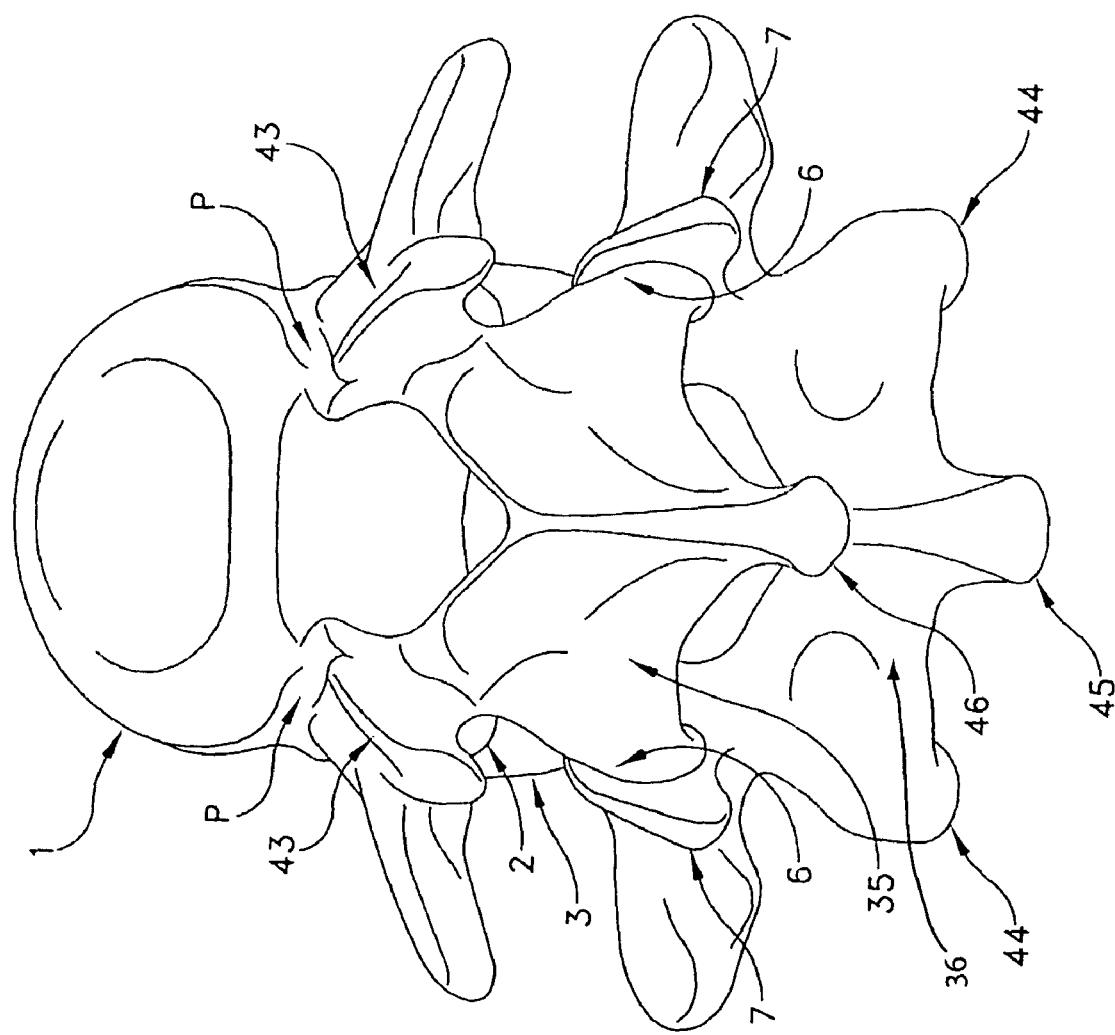
FIG. 2 is a dorsal view of the portion of the spine shown in FIG. 1.
Figure 6:
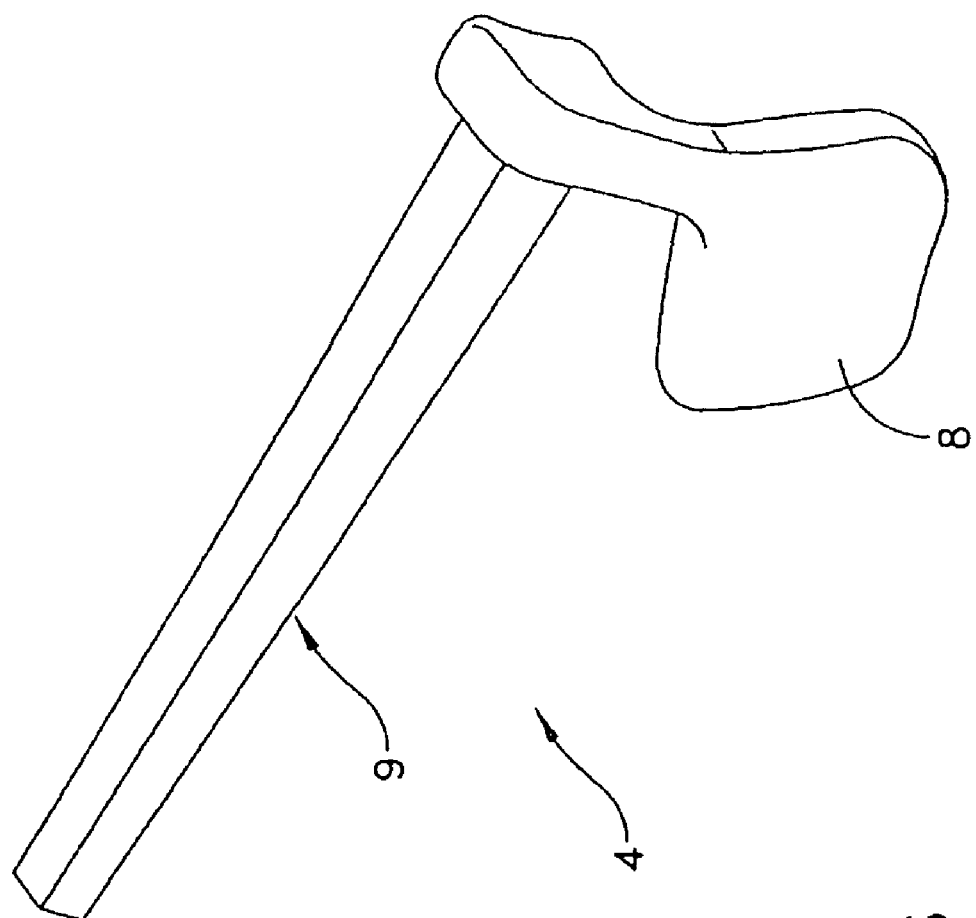
FIG. 6 is a perspective view of the left inferior facet prosthesis shown in FIGS. 3 and 4.

FIG. 6 illustrates a perspective view of inferior facet prosthesis 4. Surface 8 replicates the natural articular surface of the replaced inferior facet 6. Post 9 provides a means to affix inferior facet prosthesis 4 to vertebra 1. Post 9 is implanted into the interior bone space of the left pedicle P (FIG. 1) on vertebra 1 and may or may not extend into the vertebral body of vertebra 1 to provide additional stability.

Figure 7:
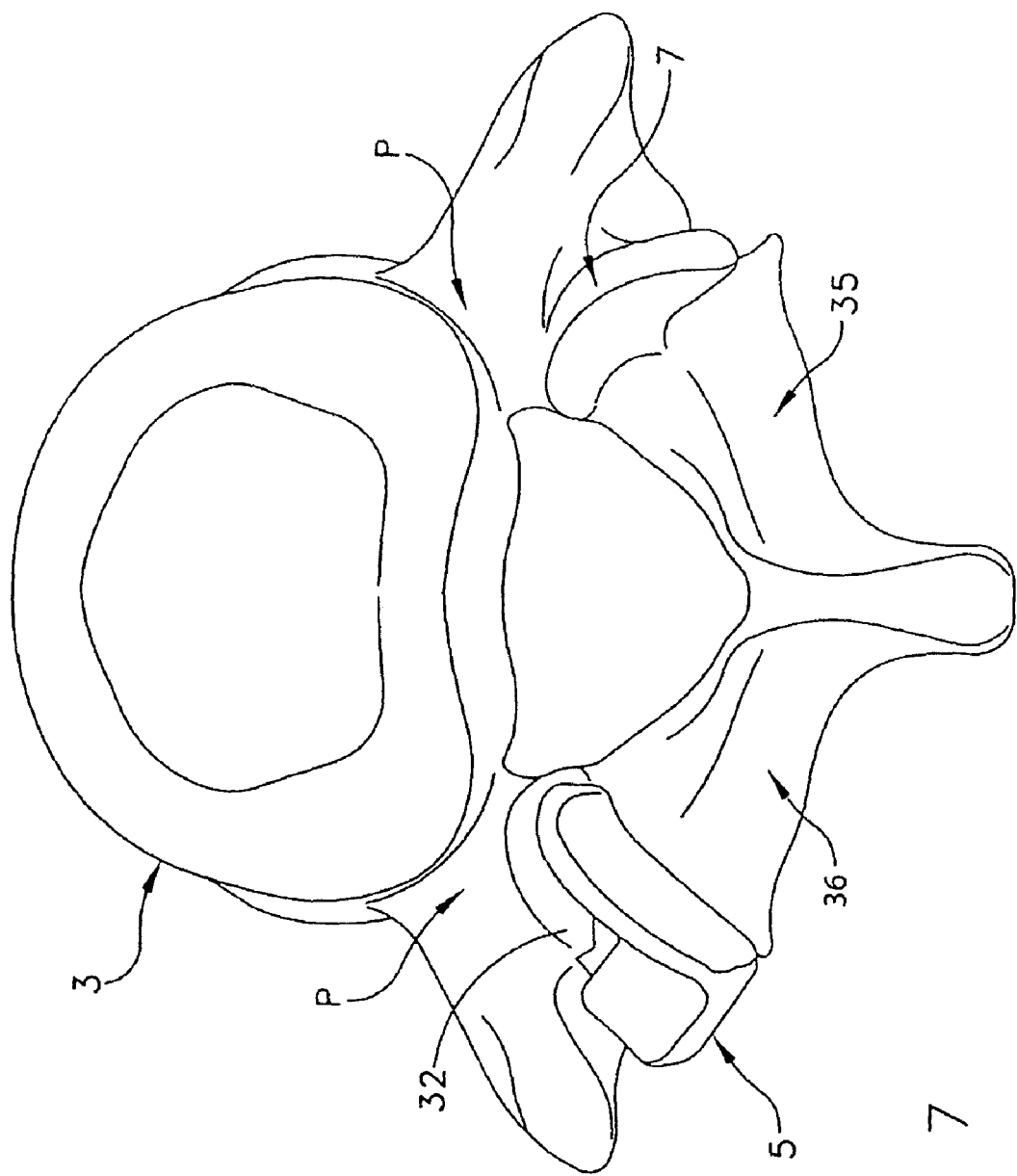
FIG. 7 is a cranial view of the implanted left superior facet prosthesis shown in FIGS. 3 and 4.

FIG. 7 illustrates a cranial view of vertebra 3 with implanted superior facet prosthesis 5. Resection surface 32 represents the bony junction between the natural superior facet 7 and the posterior arch 36.

Figure 8:
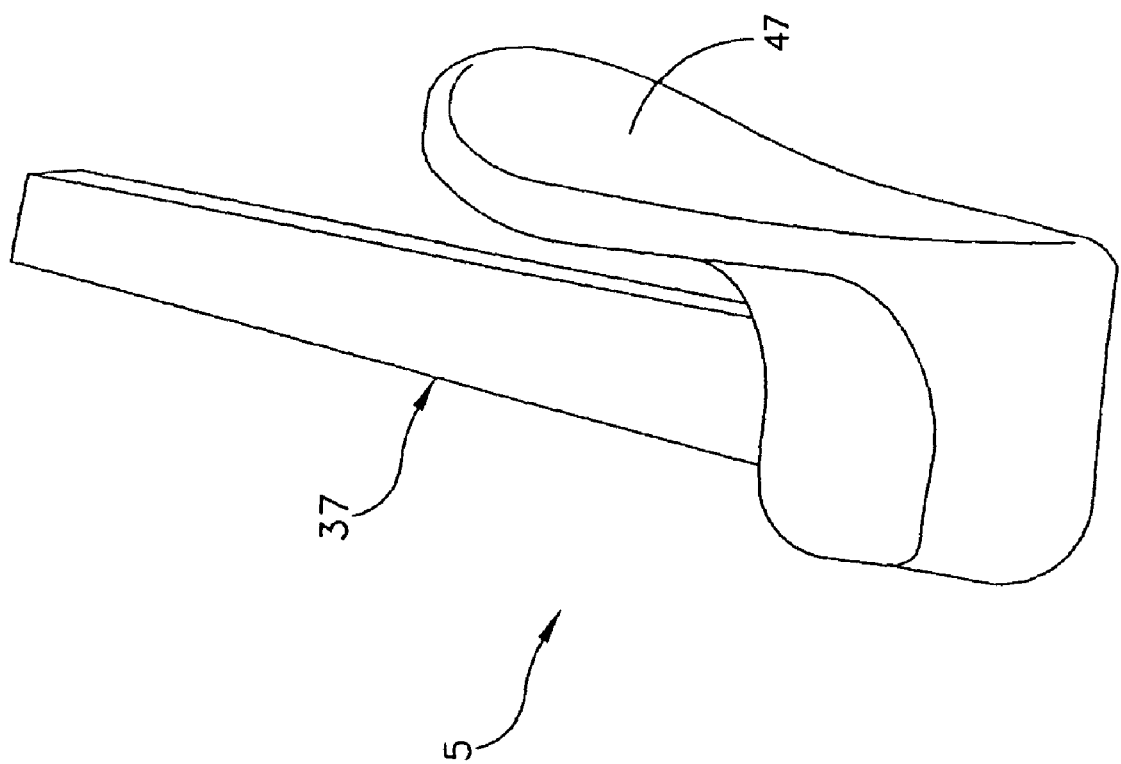
FIG. 8 is a perspective view of the left superior facet prosthesis shown in FIGS. 3 and 4.

FIG. 8 illustrates a perspective view of superior facet prosthesis 5. Surface 47 replicates the natural articular surface of the replaced superior facet 7. Post 37 provides a means for affixing superior facet prosthesis 5 to vertebra 3. Post 37 is implanted into the interior bone space of the left pedicle P (FIG. 7) on vertebra 3 and may or may not extend into the vertebral body of vertebra 3 to provide additional stability.

When the total facet joint is replaced, as shown in FIGS. 3 and 4, then surface 8 (FIG. 6) articulates with surface 47 (FIG. 8) to recreate the natural biomechanics of the spine motion segment made up of vertebra 1, vertebra 3, and artificial disc AD.

Figure 9:
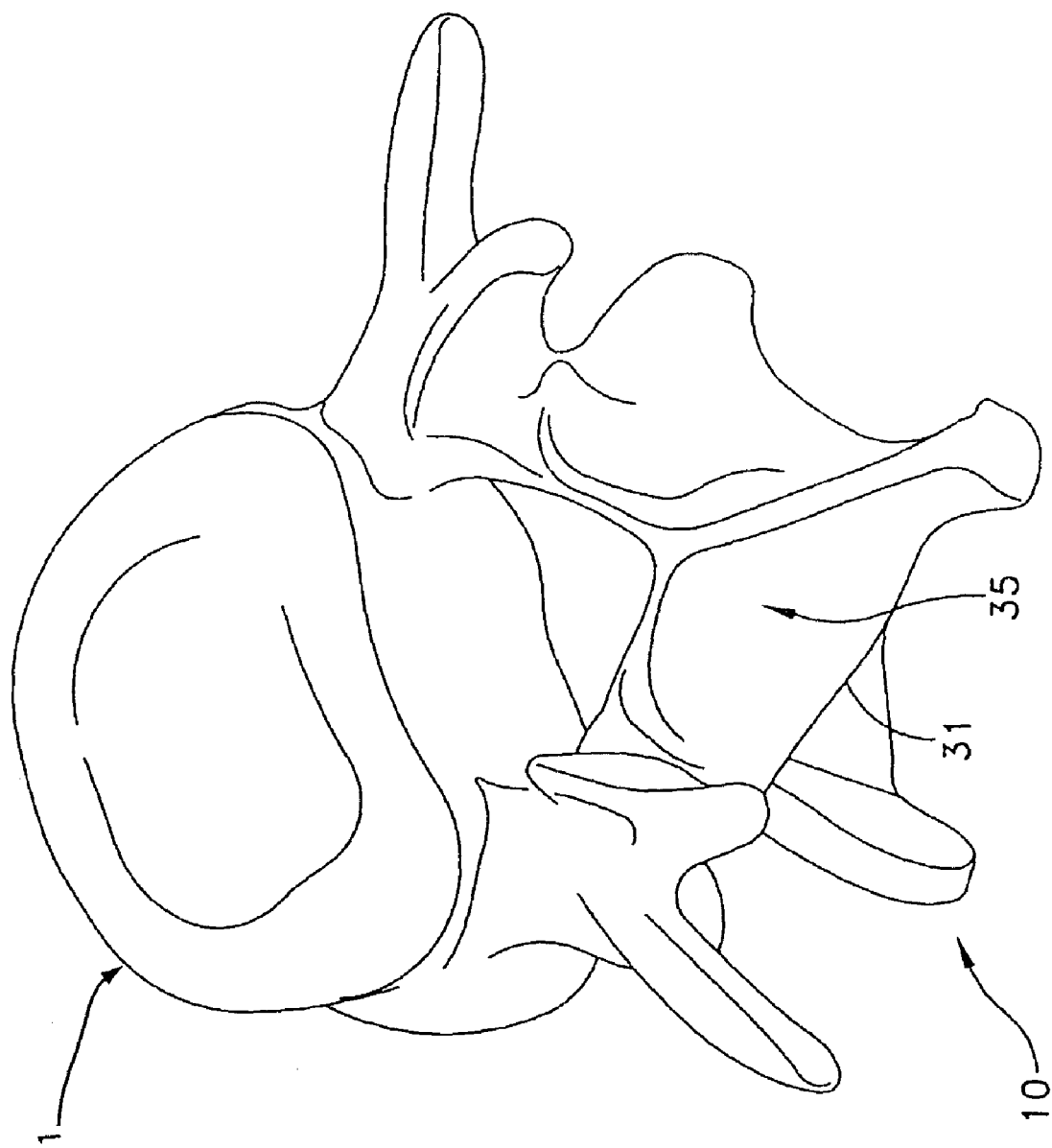
FIG. 9 is a perspective view of an alternate implanted left inferior facet prosthesis.

FIG. 9 illustrates an alternative inferior facet prosthesis 10 which is implanted into the interior bone space of posterior arch 35. The interior bone space is accessed from the resection 31.

Figure 10:
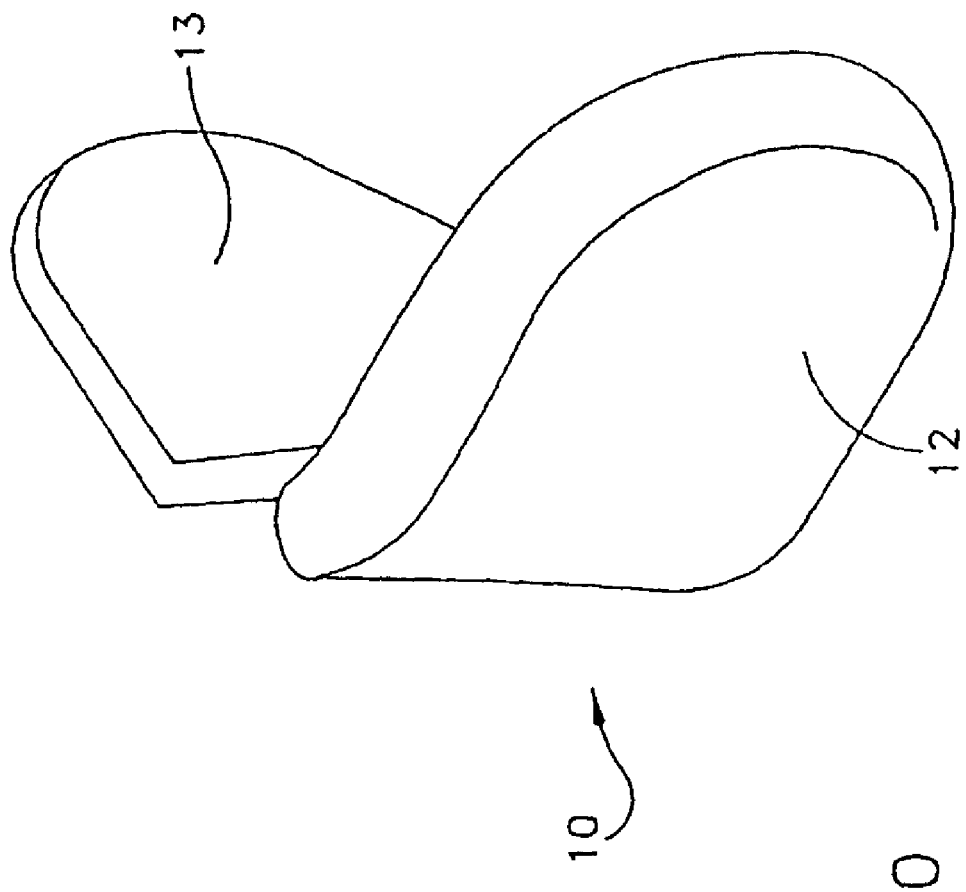
FIG. 10 is a perspective view of an alternate left inferior facet prosthesis.

FIG. 10 shows details of alternative inferior facet prosthesis 10, including the fin 13 that extends into the interior bone space of posterior arch 35. Surface 12 replicates the natural articular surface of the replaced facet.

If desired, a corresponding fin construction can be used to form a prosthetic superior facet.

The surfaces of post 9 (FIG. 6), post 37 (FIG. 8) and fin 13 (FIG. 10) may or may not include porous coatings to facilitate bone ingrowth to enhance the long term fixation of the implant. Furthermore, such porous coatings may or may not include osteoinductive or osteoconductive substances to further enhance the bone remodeling into the porous coating.

Figure 11:
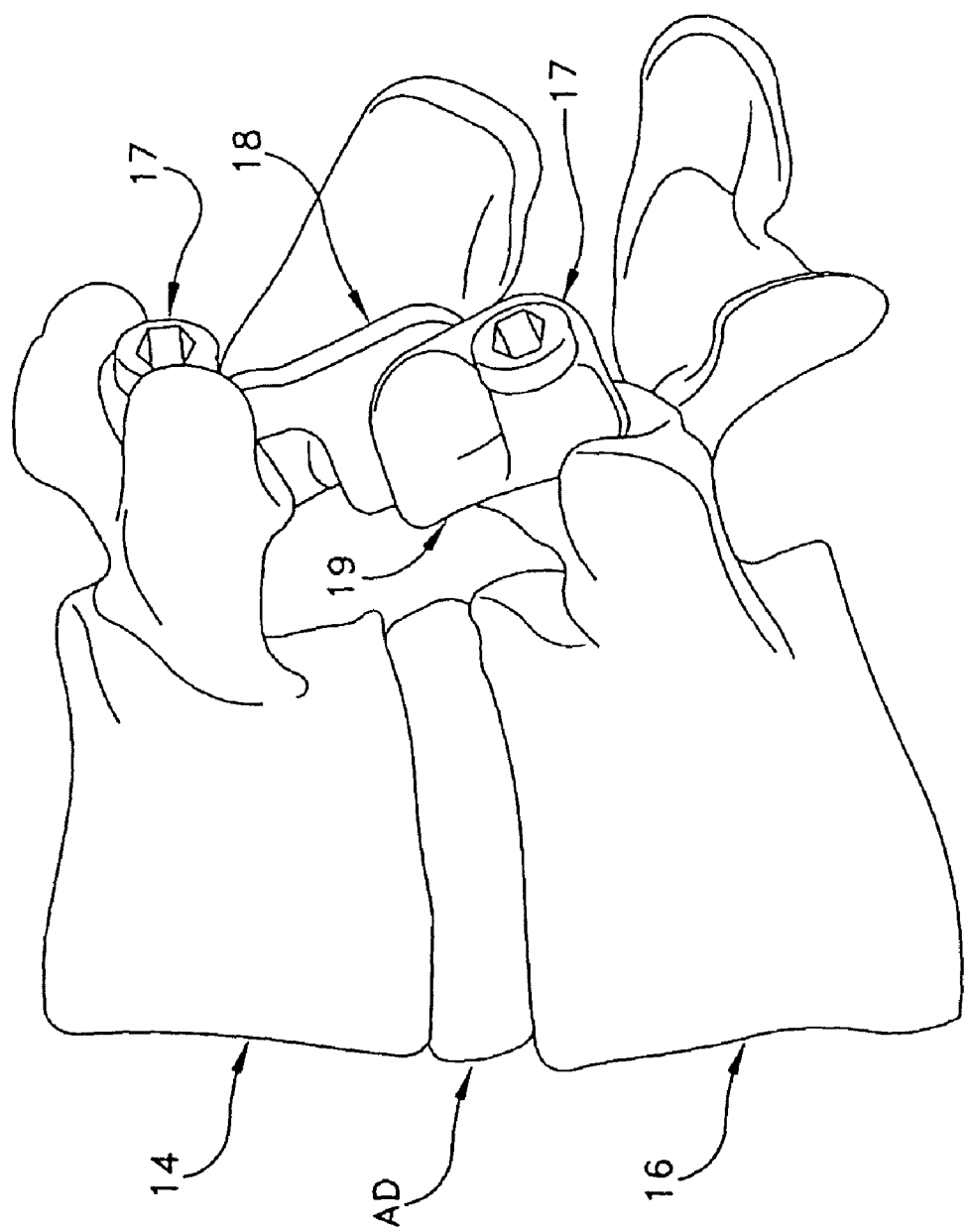
FIG. 11 is a lateral view of an alternative reconstructed spine joint.

Referring now to FIG. 11, there is shown a lateral view of a superior vertebra 14 and an inferior vertebra 16, with an artificial disc AD located in between as shown. The left inferior facet of vertebra 14 has been resected and an inferior facet prosthesis 18 has been attached to vertebra 14 by means of a screw fastener 17. Similarly, the left superior facet of vertebra 16 has been resected and a superior facet prosthesis 19 has been attached to vertebra 16 by means of a screw fastener 17.

Figure 12:
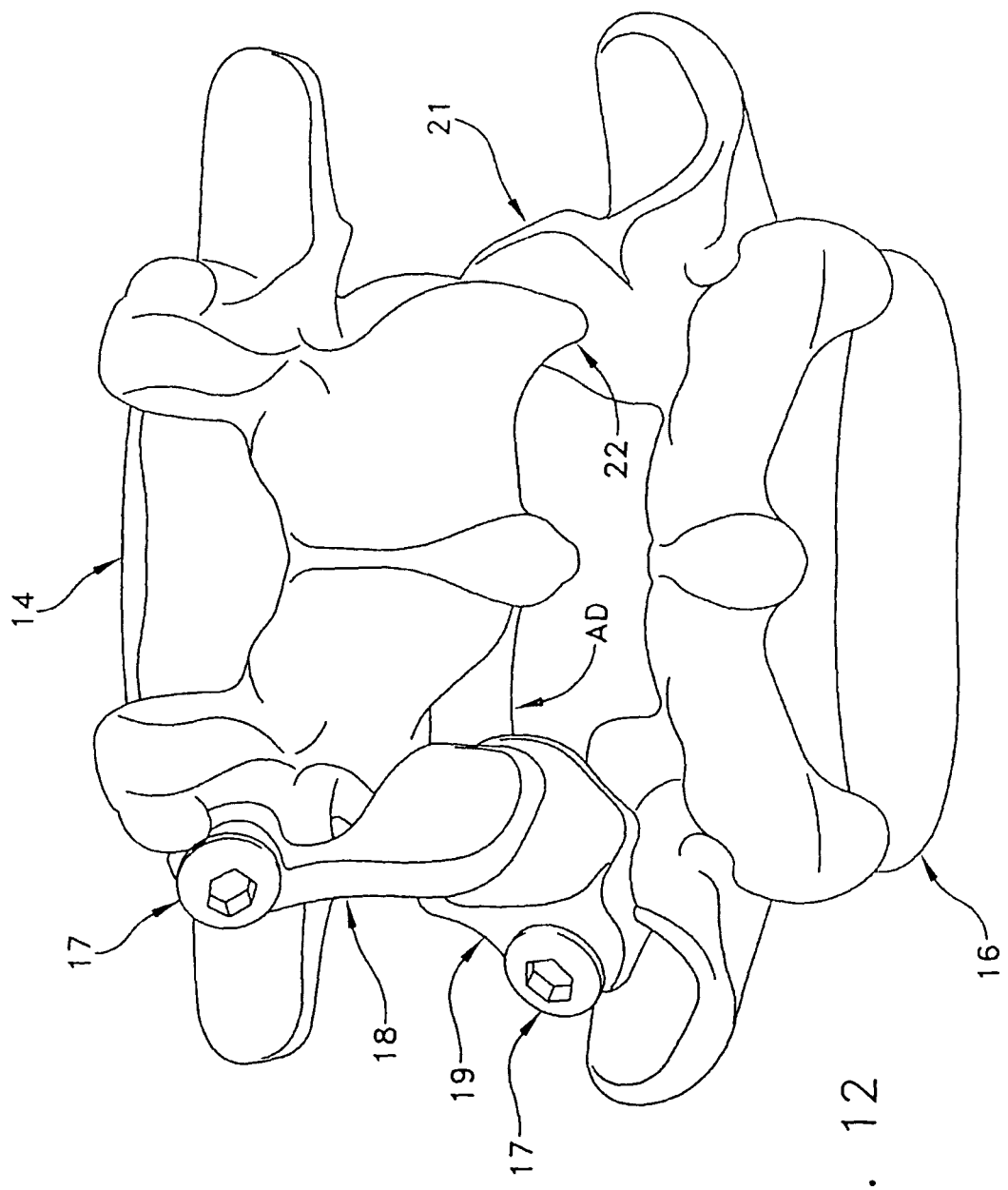
FIG. 12 is a dorsal view of an alternative reconstructed spine joint.

FIG. 12 illustrates a dorsal view of the elements of FIG. 11. It can be appreciated that inferior facet prosthesis 18 replicates the natural anatomy when compared to the contralateral inferior facet 22 of vertebra 14. Similarly, it can be appreciated that superior facet prosthesis 19 replicates the natural anatomy when compared to the contralateral superior facet 21 of vertebra 16.

Figure 13:
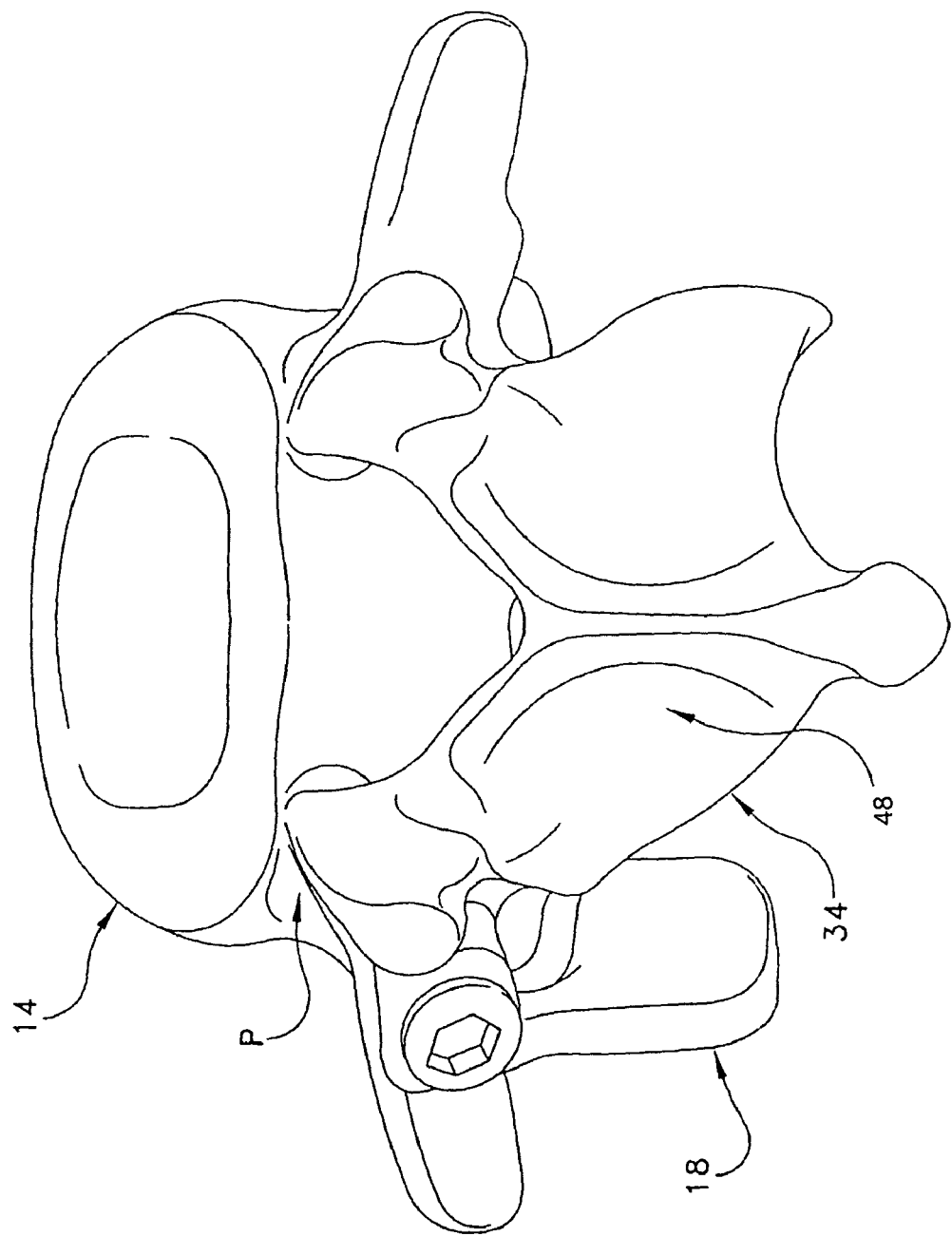
FIG. 13 is a perspective view of the implanted left inferior facet prosthesis shown in FIGS. 11 and 12.

Turning now to FIG. 13, there is provided a perspective view of vertebra 14 with implanted inferior facet prosthesis 18. Resection 34 has removed the natural inferior facet at the bony junction between the inferior facet and the posterior arch 48. In this manner, bone pain associated with a disease, such as osteoarthritis, or trauma may be eliminated inasmuch as the involved bony tissue has been osteotomized.

Figure 14:
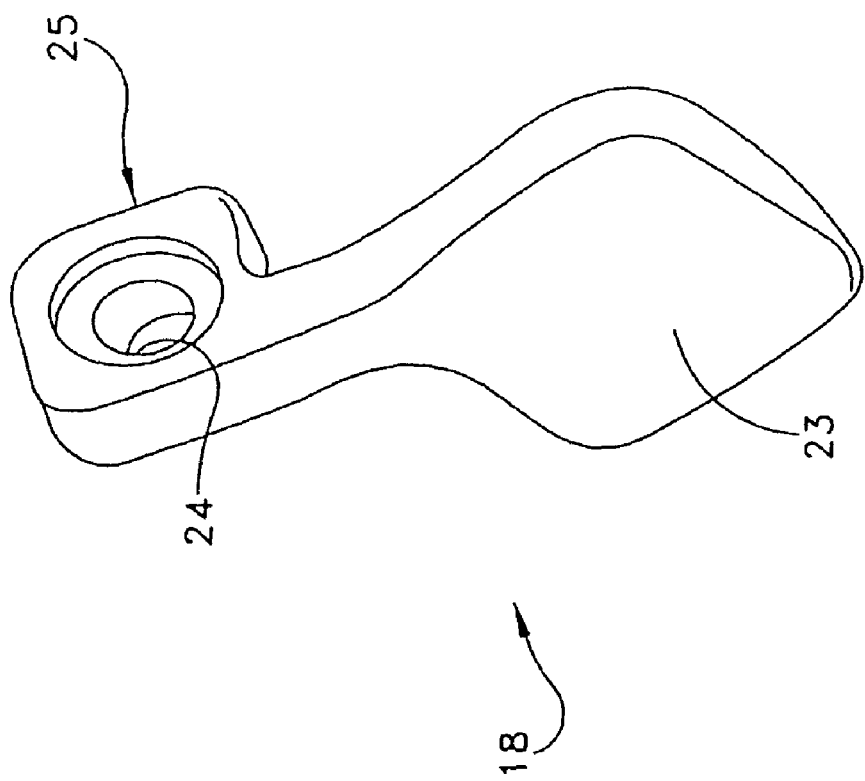
FIG. 14 is a perspective view of the alternative left inferior facet prosthesis shown in FIGS. 11 and 12.

FIG. 14 illustrates a perspective view of inferior facet prosthesis 18. Surface 23 m replicates the natural articular surface of the replaced facet. Flange 25 contacts the pedicle and hole 24 receives a fastener to attach inferior facet prosthesis 18 to vertebra 14.

Figure 15:
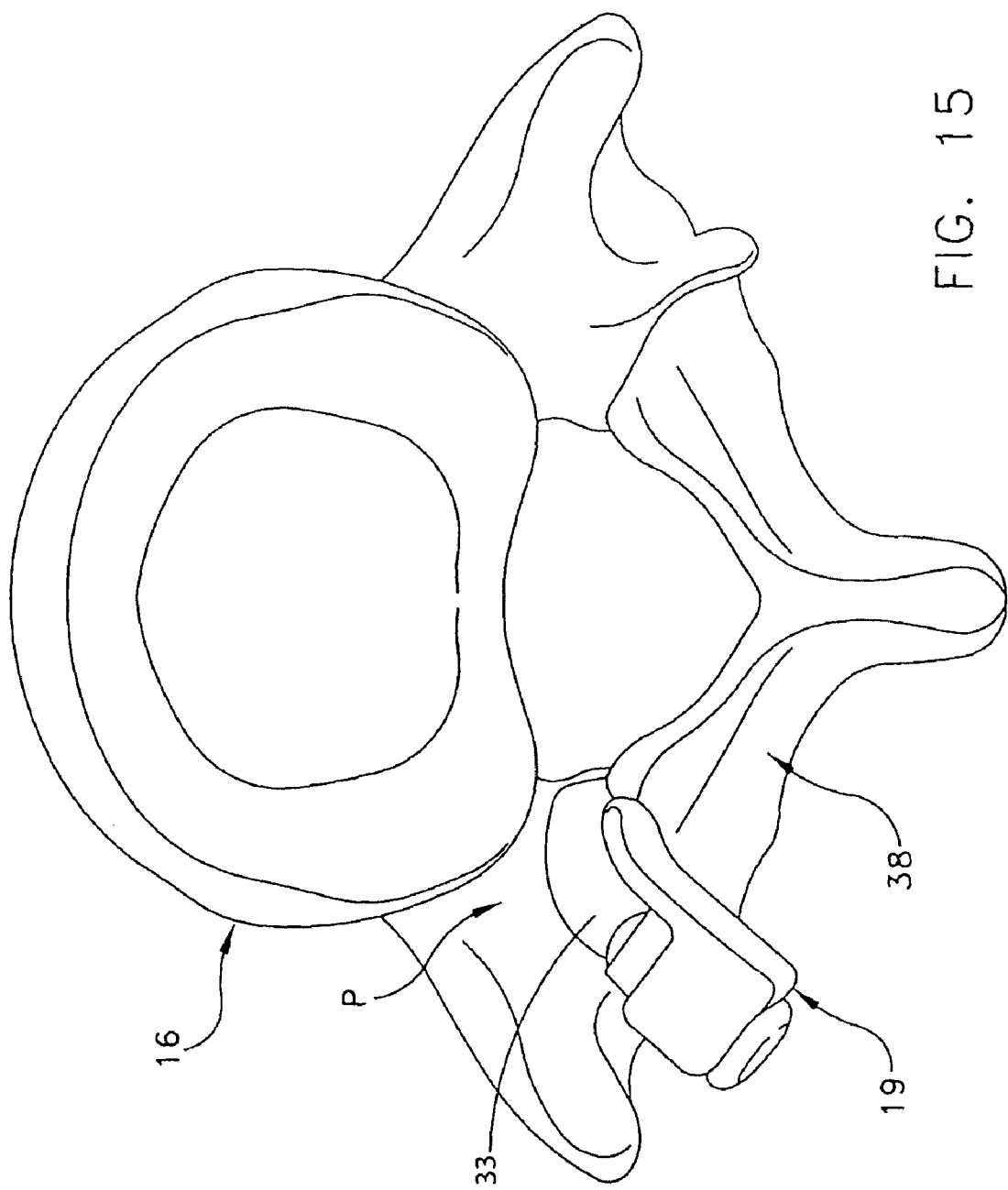
FIG. 15 is a cranial view of the alternative implanted left superior facet prosthesis shown in FIGS. 11 and 12.

FIG. 15 illustrates a cranial view of vertebra 16 with implanted superior facet prosthesis 19. Resection surface 33 represents the bony junction between the natural superior facet and the posterior arch 38.

Figure 16:
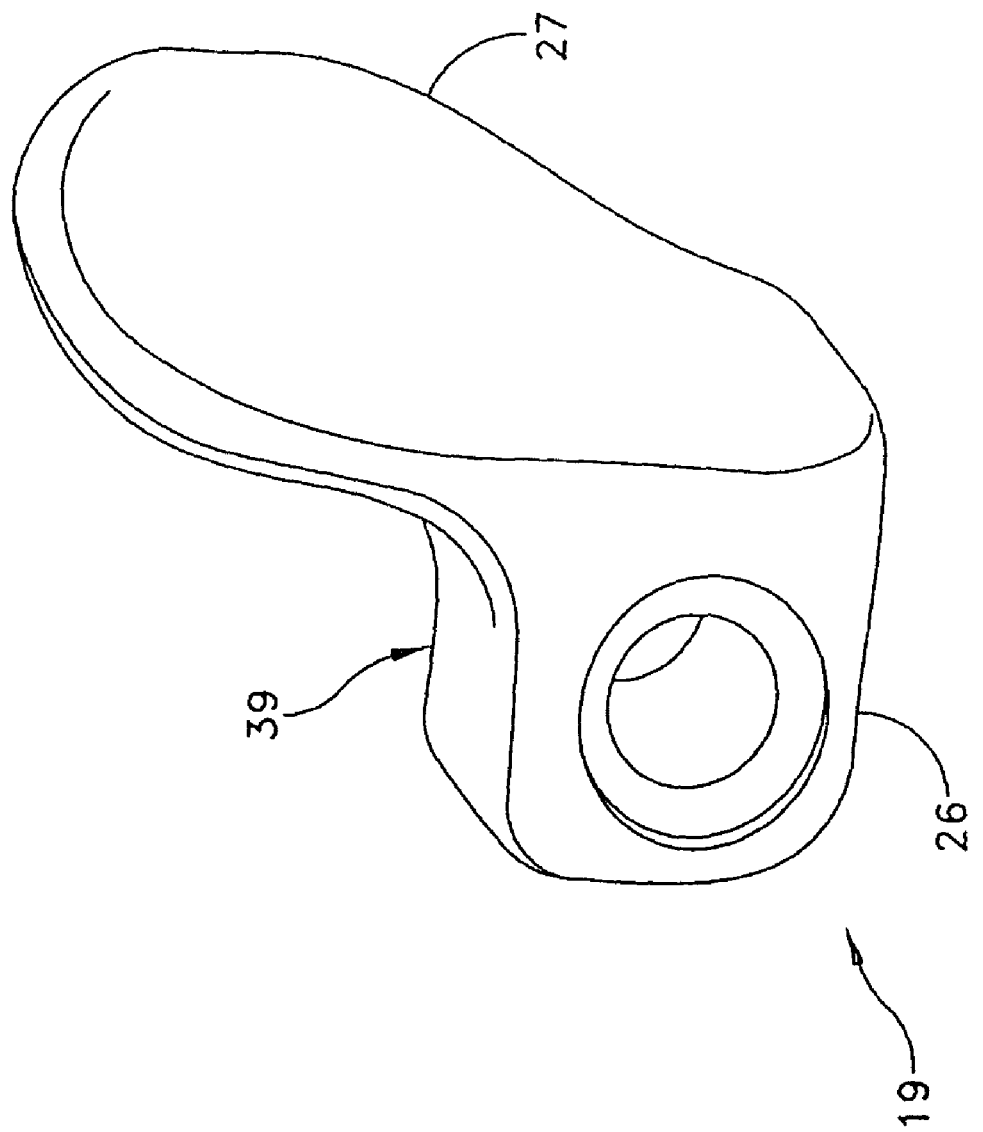
FIG. 16 is a perspective view of the alternative left superior facet prosthesis shown in FIGS. 11 and 12.

FIG. 16 illustrates a perspective view of superior facet prosthesis 19. Surface 27 replicates the natural articular surface of the replaced facet. Flange 39 contacts the pedicle and hole 26 receives a fastener to attach inferior facet prosthesis 19 to vertebra 16.

Figure 17:
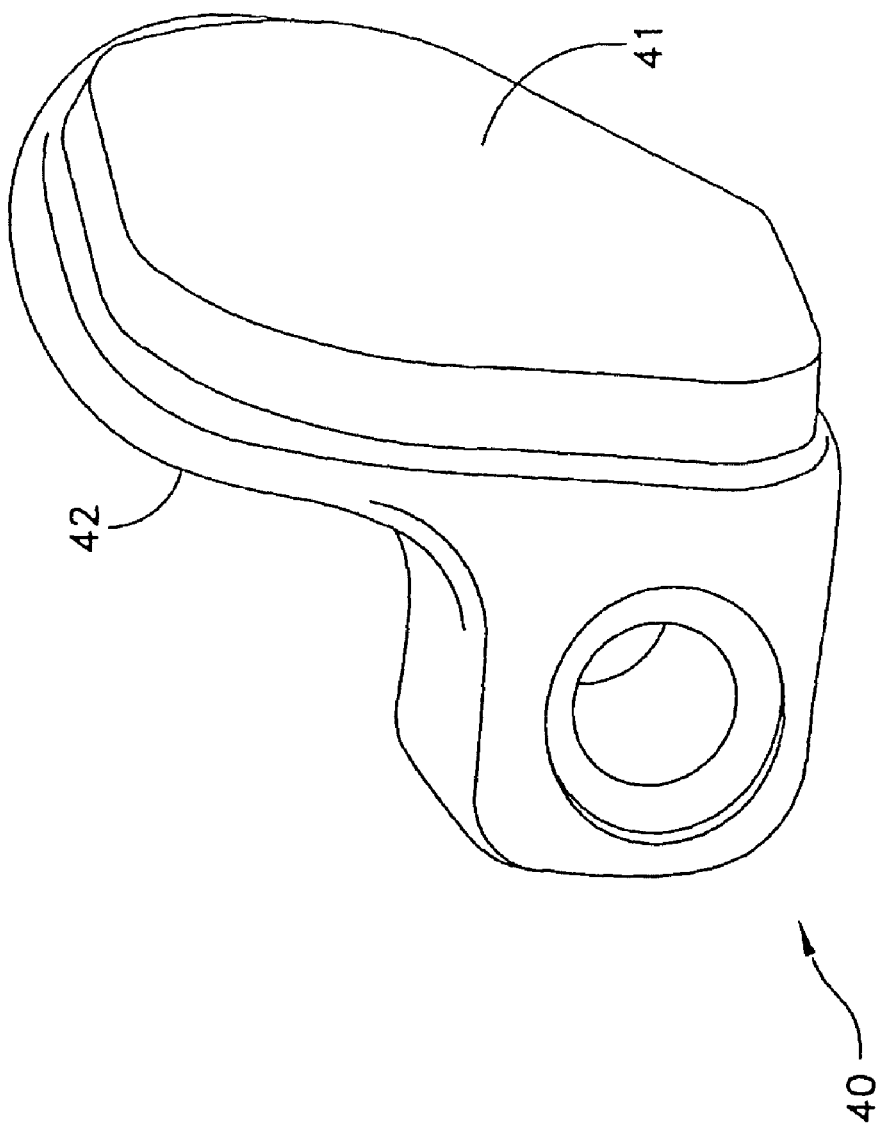
FIG. 17 is a perspective view of an alternate bearing surface for the superior facet prosthesis shown in FIG. 16.

FIG. 17 illustrates an alternative superior facet prosthesis 40 with an bearing surface 41 that mounts to substrate 42. The bearing surface 41 is a biocompatible polymeric material, such as ultra high molecular weight polyethylene. Alternately, the bearing surface can be ceramic, such as zirconia or alumina, or metal. The substrate is a biocompatible metal alloy, such as an alloy of titanium, cobalt, or iron.

Disc Prosthesis and Double Facet Prosthesis

Figure 19:
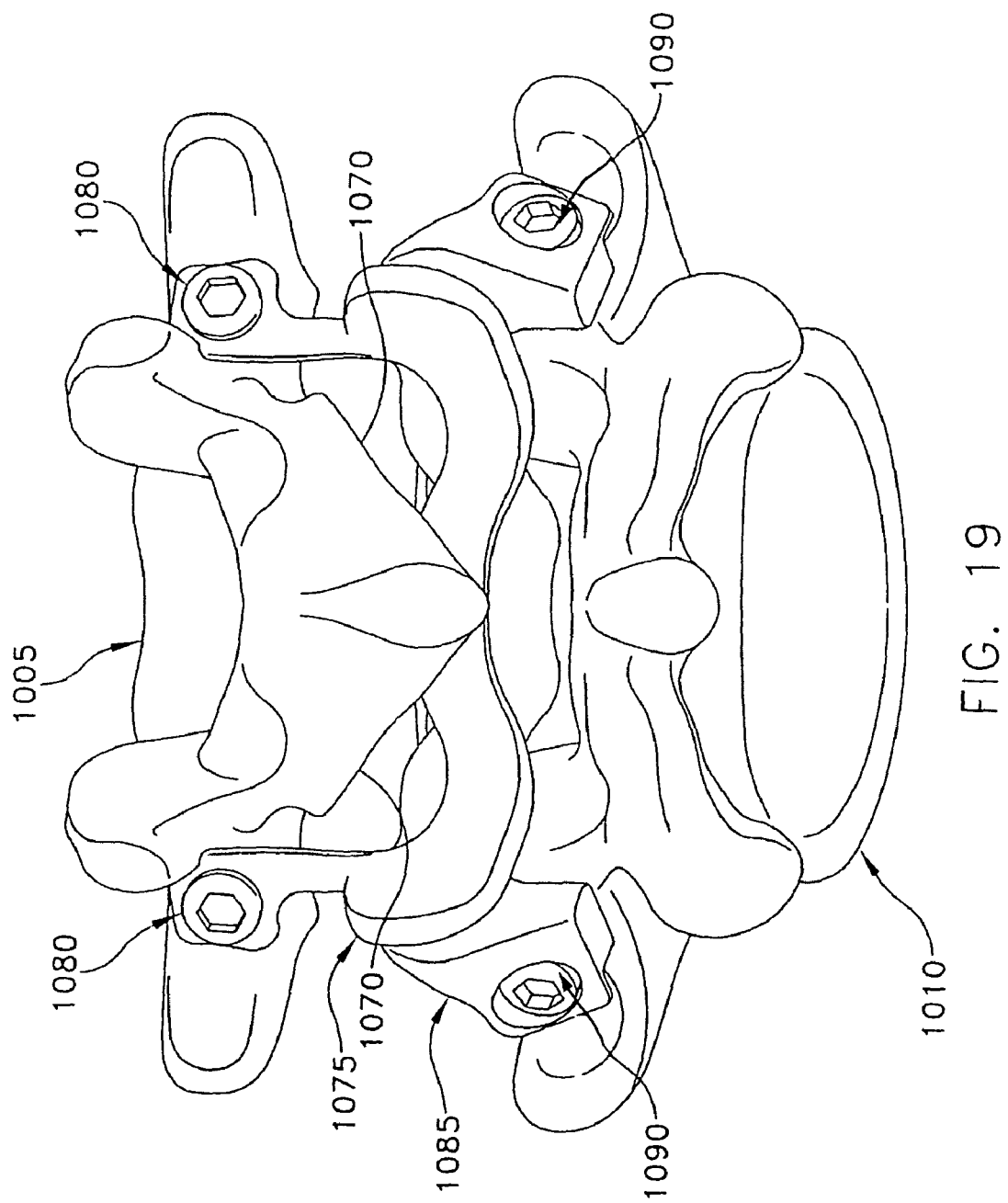
FIG. 19 is a dorsal view of a bilateral facet joint reconstructed in accordance with the present invention.
Figure 20:
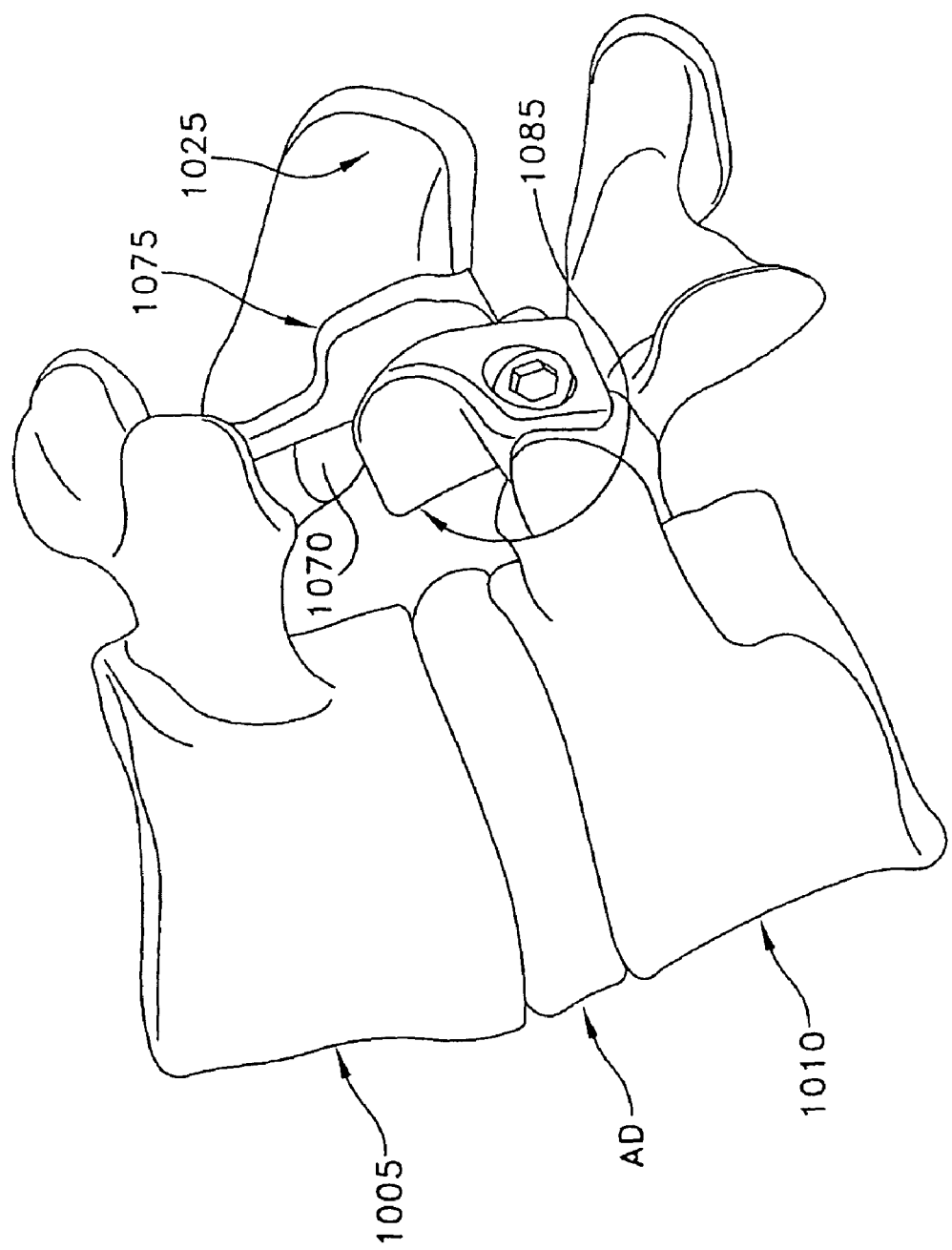
FIG. 20 is a lateral view of the bilateral facet joint prosthesis shown in FIG. 19.

Referring now to FIGS. 19 and 20, in accordance with another aspect of the invention, intervertebral disc 1015 has been replaced by an artificial disc AD'. Artificial disc AD' comprises opposing end plates 2905, 2906 and a deformable structure 2907 disposed between the end plates 2905, 2906. The deformable structure 2907 may be an elastomeric body 2908 or a polymer body. The artificial disc AD' is described in further detail in U.S. Pat. No. 5,071,437. This artificial disc AD' may be a device such as is described by Stefee et al. in U.S. Pat. No. 5,071,437; Gill et al. in U.S. Pat. No. 6,113,637; Bryan et al. in U.S. Pat. No. 6,001,130; Hedman et al. in U.S. Pat. No. 4,759,769; Ray in U.S. Pat. No. 5,527,312; Ray et al. in U.S. Pat. No. 5,824,093; Buttner-Janz in U.S. Pat. No. 5,401,269; and Serhan et al. in U.S. Pat. No. 5,824,094; all which documents are hereby incorporated herein by reference. Alternatively, the artificial disc may be some other artificial disc of the sort known in the art.

Referring now to FIGS. 19 and 20, in accordance with another aspect of the invention, intervertebral disc 1015 has been replaced by an artificial disc AD. This artificial disc AD may be a device such as is described by Stefee et al. in U.S. Pat. No. 5,071,437; Gill et al. in U.S. Pat. No. 6,113,637; Bryan et al. in U.S. Pat. No. 6,001,130; Hedman et al. in U.S. Pat. No. 4,759,769; Ray in U.S. Pat. No. 5,527,312; Ray et al. in U.S. Pat. No. 5,824,093; Buttner-Janz in U.S. Pat. No. 5,401,269; and Serhan et al. in U.S. Pat. No. 5,824,094; all which documents are hereby incorporated herein by reference. Alternatively, the artificial disc may be some other artificial disc of the sort known in the art.

In addition to the foregoing, the left and right inferior facets 1025 of vertebra 1005 have been resected at 1070 and a bilateral inferior facet prosthesis 1075 has been attached to vertebra 1005 using screw fasteners 1080. Similarly, the left and right superior facets 1045 of vertebra 1010 have been resected at 1082 (FIG. 24) and a bilateral superior facet prosthesis 1085 has been attached to vertebra 1010 using screw fasteners 1090.

Figure 18:
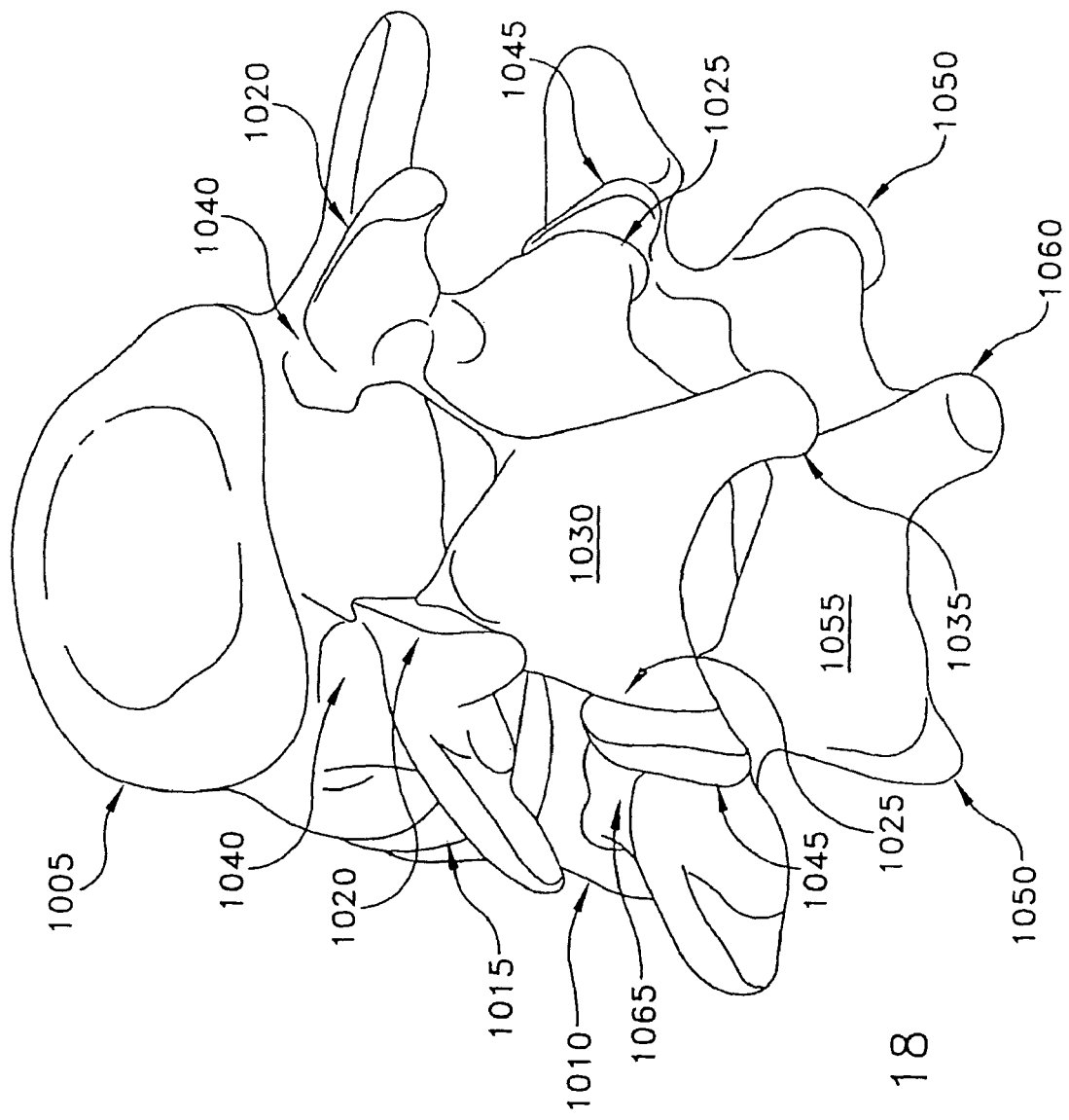
FIG. 18 is a perspective view of a spine motion segment.

In FIG. 20 it can be appreciated that bilateral inferior facet prosthesis 1075 replicates the natural anatomy when compared to the intact inferior facets 1025 of vertebra 1005 (FIG. 18). Furthermore, bilateral facet prosthesis 1075 extends from its attachment point in a manner that does not require contact with, or mating to, the complex geometry of the lamina (or posterior arch) 1030. Resection surfaces 1070 provide adequate clearance for bilateral inferior facet prosthesis 1075 and provide complete removal of the diseased or traumatized natural inferior facets 1025.

Figure 21:
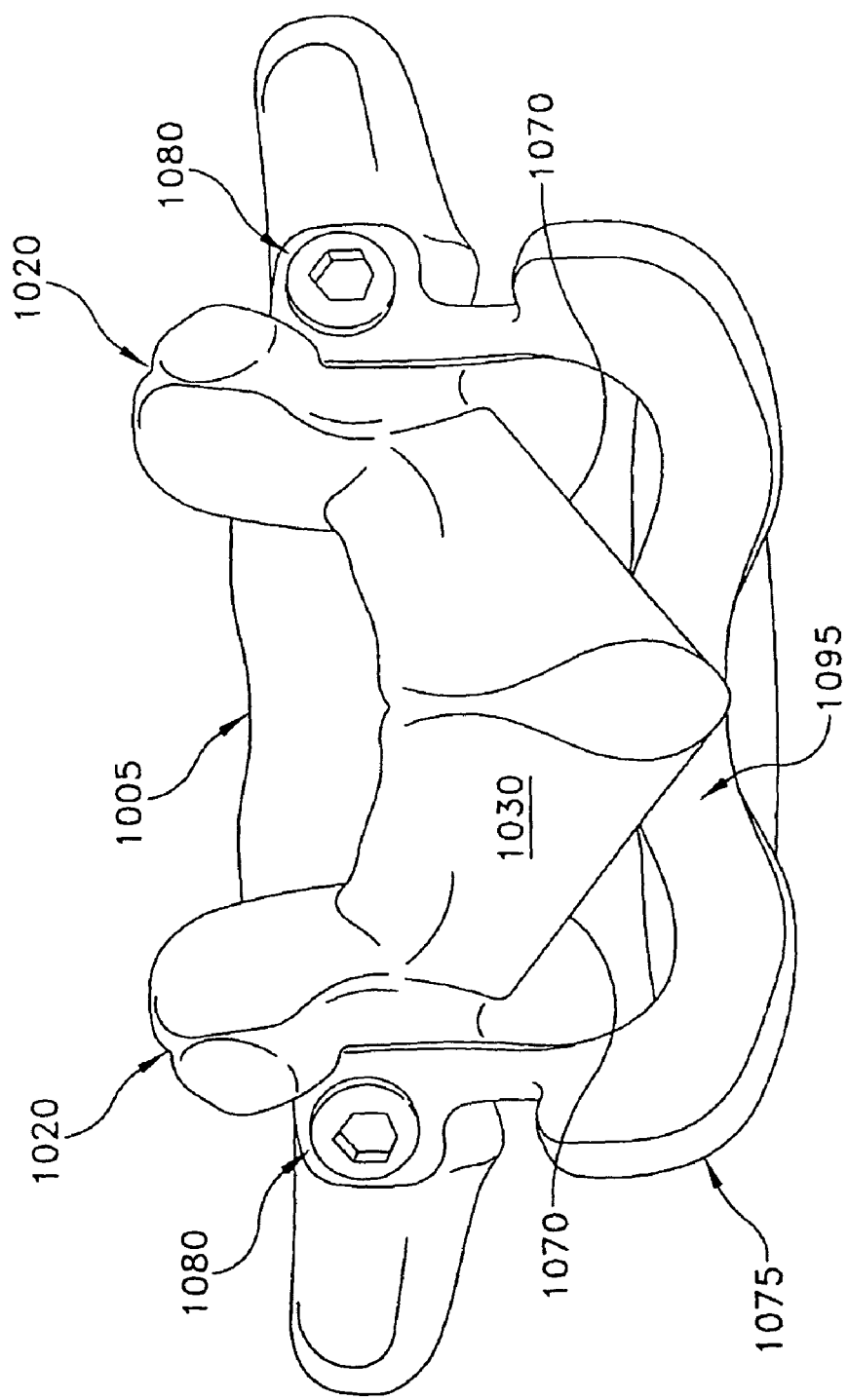
FIG. 21 is a dorsal view of the implanted inferior bilateral facet prosthesis shown in FIGS. 19 and 20.
Figure 22:
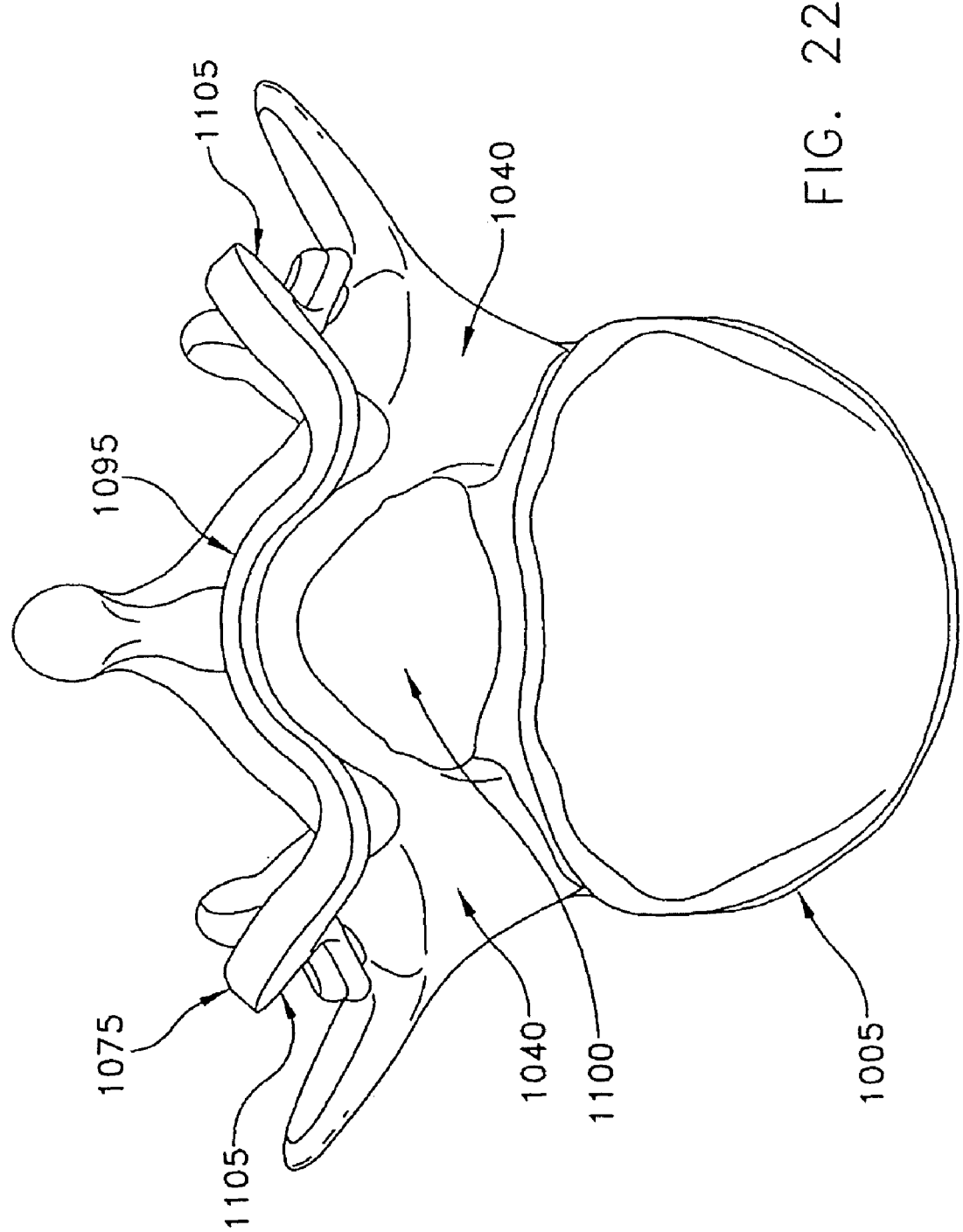
FIG. 22 is an inferior view of the implanted inferior bilateral facet prosthesis shown in FIGS. 19 and 20.

FIGS. 21 and 22 illustrate how the geometry of the bridge 1095 of bilateral inferior facet prosthesis 1075 matches that of the posterior arch 1030 of vertebra 1005 in order to provide adequate clearance for the central foramen 1100. Articular surfaces 1105 articulate with the opposing superior facets 1045 (or their prosthetic replacements) of the vertebra 1010.

Figure 23:
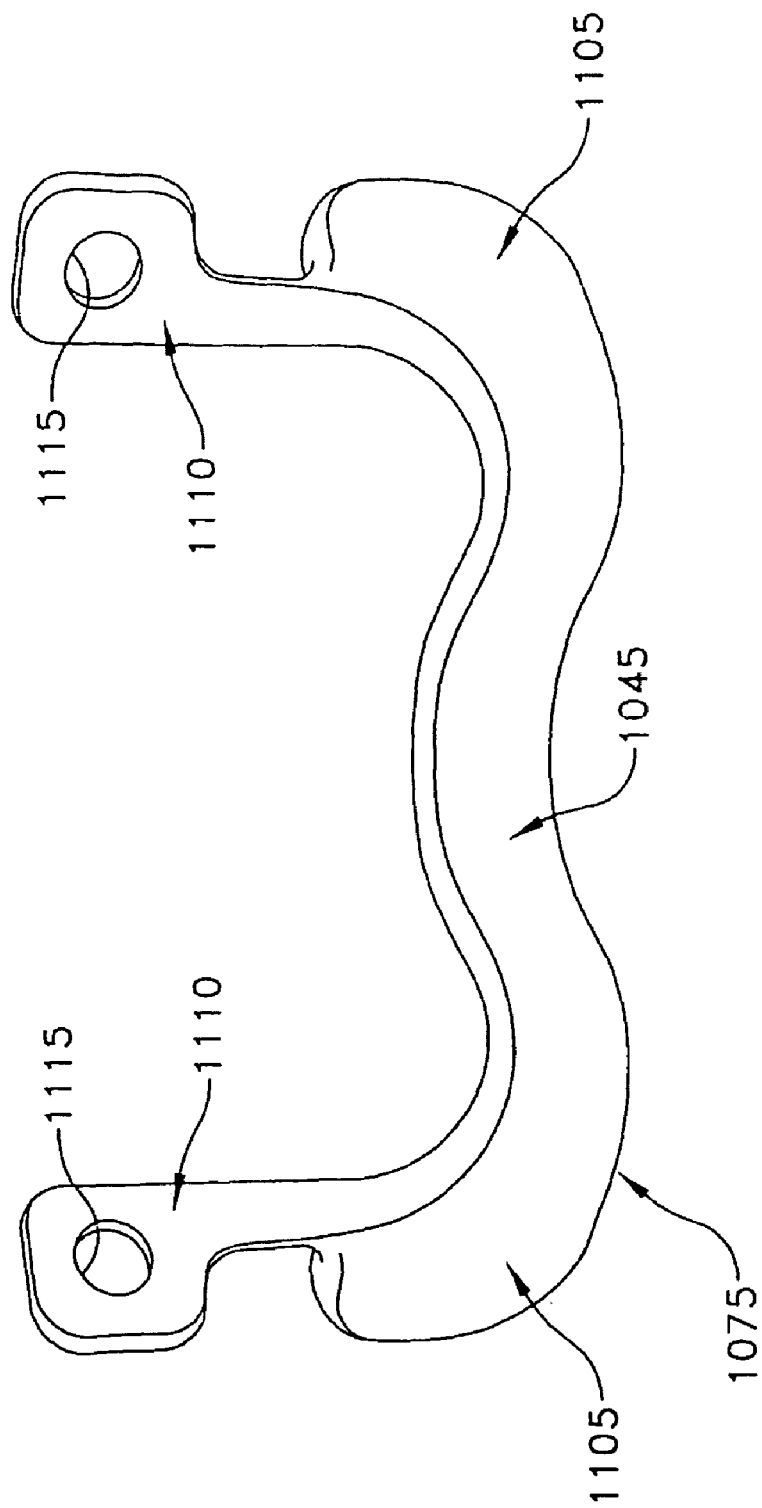
FIG. 23 is a ventral view of the inferior bilateral facet prosthesis shown in FIGS. 21 and 22.

FIG. 23 illustrates the bilateral inferior facet prosthesis 1075 with flanges 1110 that about against the pedicles 1040 of vertebra 1005. Bridge 1095 connects the articular surfaces 1105. Holes 1115 allow the attachment of bilateral inferior facet prosthesis 1075 to vertebra 1005 by means of screw fasteners 1080. Alternatively, screw fasteners 1080 could be replaced with staples, pins, tacks, anchors, modular fixation posts, or the like. These alternative fasteners could further include porous coatings to further enhance bony fixation, and could also include osteoconductive or osteoinductive substances.

Figure 24:
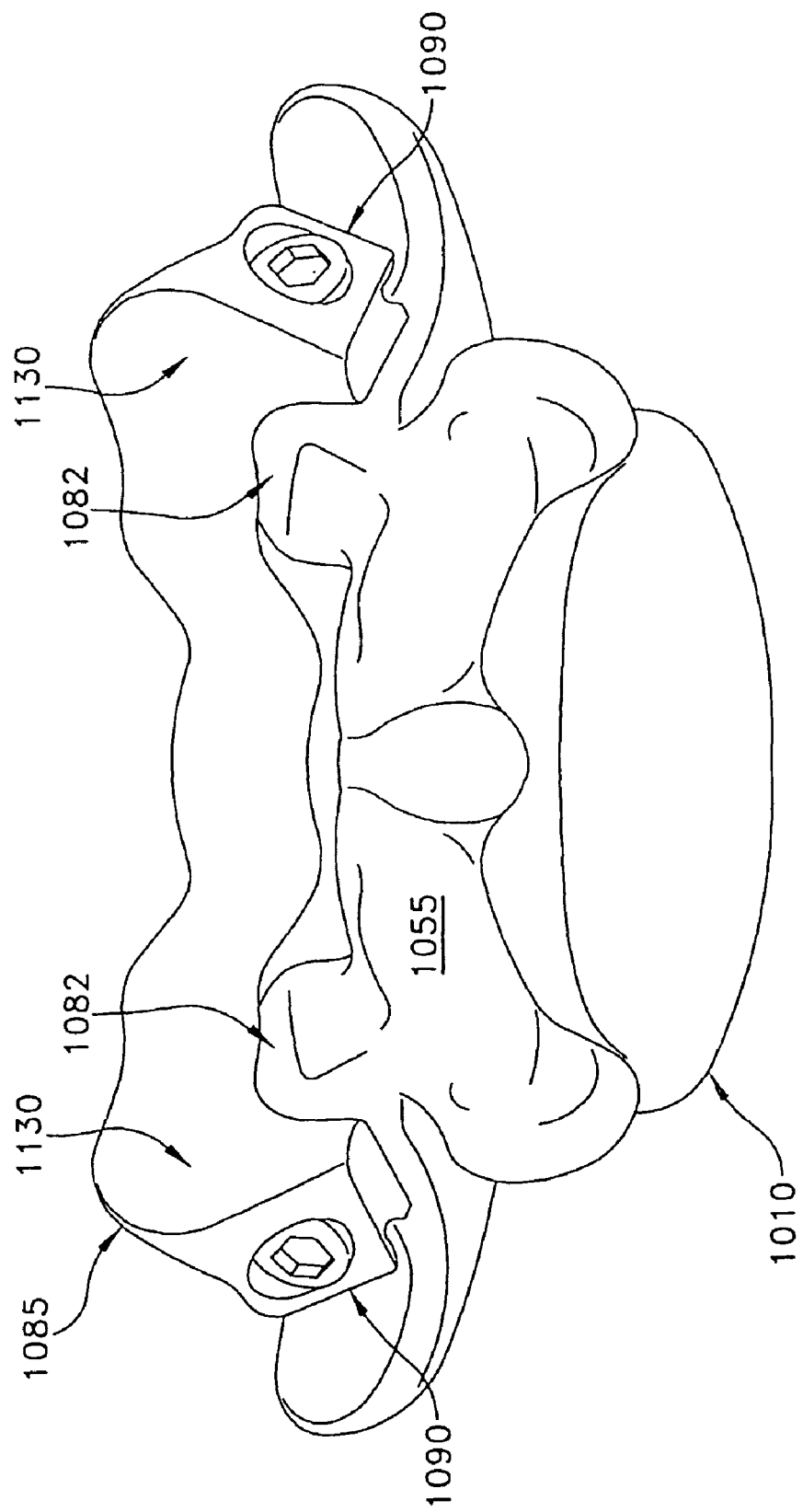
FIG. 24 is a dorsal view of the implanted superior bilateral facet prosthesis shown in FIGS. 19 and 20.

In FIG. 24 it can be appreciated that bilateral superior facet prosthesis 1085 replicates the natural anatomy when compared to the intact superior facets 1045 of vertebra 1010. Furthermore, bilateral facet prosthesis 1085 extends from its attachment point in a manner that does not require contact with, or mating to, the complex geometry of the lamina (or posterior arch) 1055. Resection surfaces 1082 provide adequate clearance for bilateral superior facet prosthesis 1085 and provide complete removal of the diseased or traumatized natural superior facets 1045.

Figure 25:
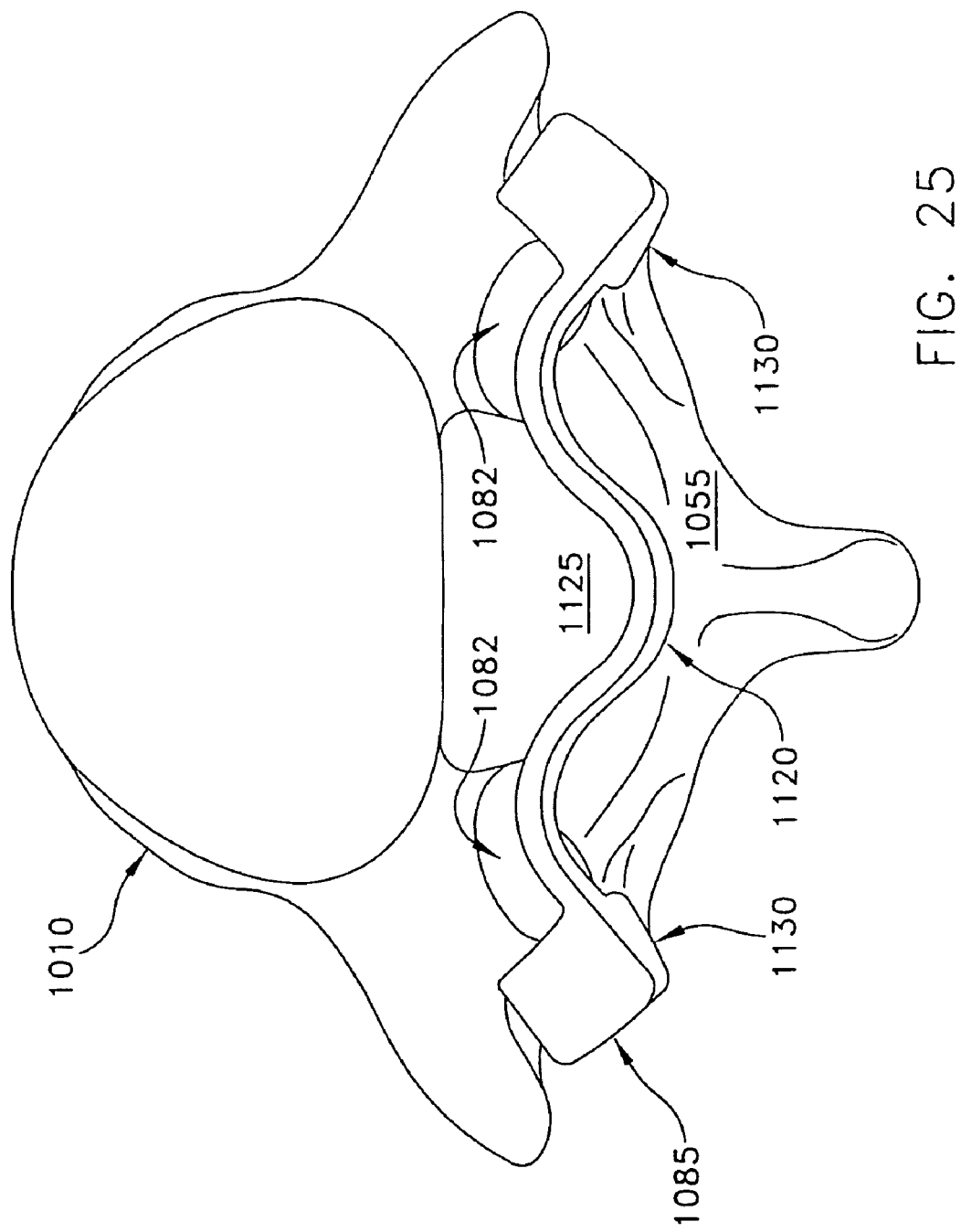
FIG. 25 is a superior view of the implanted superior bilateral facet prosthesis shown in FIGS. 19 and 20

FIG. 25 illustrates how the geometry of the bridge 1120 of bilateral superior facet prosthesis 1085 matches that of the posterior arch 1055 of vertebra 1010 in order to provide adequate clearance for the central foramen 1125. Articular surfaces 1130 articulate with the opposing inferior facets of the vertebra 1005.

Figure 26:
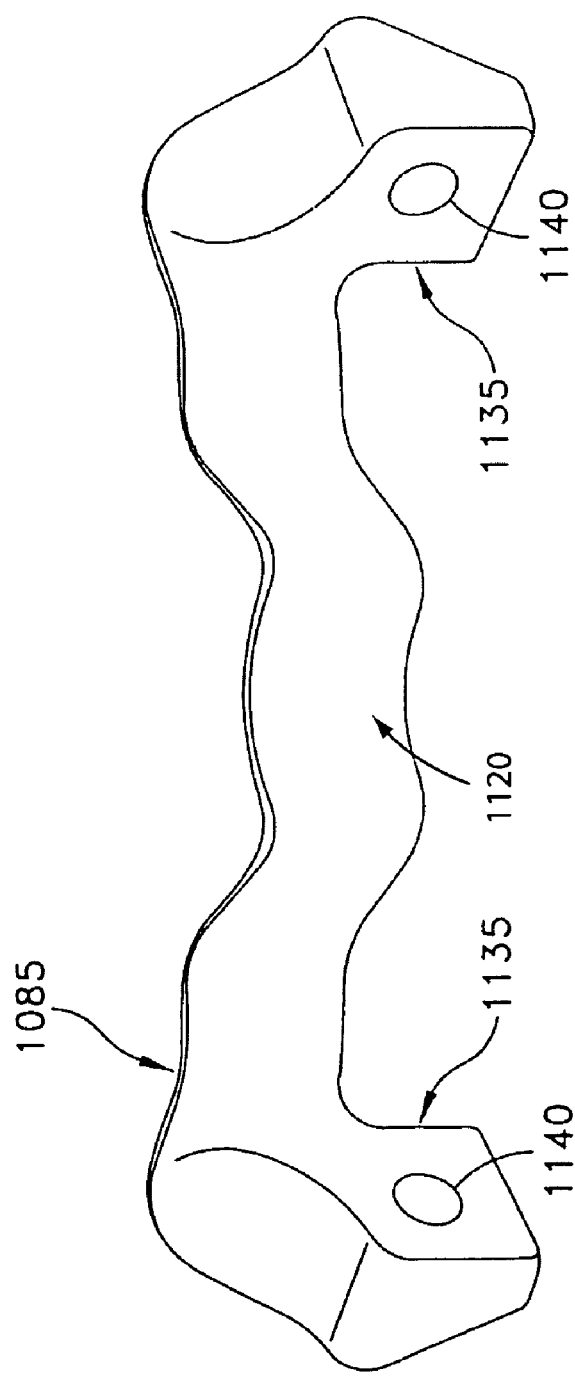
FIG. 26 is a ventral view of the superior bilateral facet prosthesis shown in FIGS. 24 and 25.

FIG. 26 illustrates the bilateral superior facet prosthesis 1085 with flanges 1135 that abut against the pedicles 1065 of vertebra 1010. Bridge 1120 connects the articular surfaces 1130 (seen in FIG. 25 but not seen in FIG. 26). Holes 1140 allow the attachment of bilateral superior facet prosthesis 1085 to vertebra 1010 by means of screw fasteners 1090.

Figure 27:
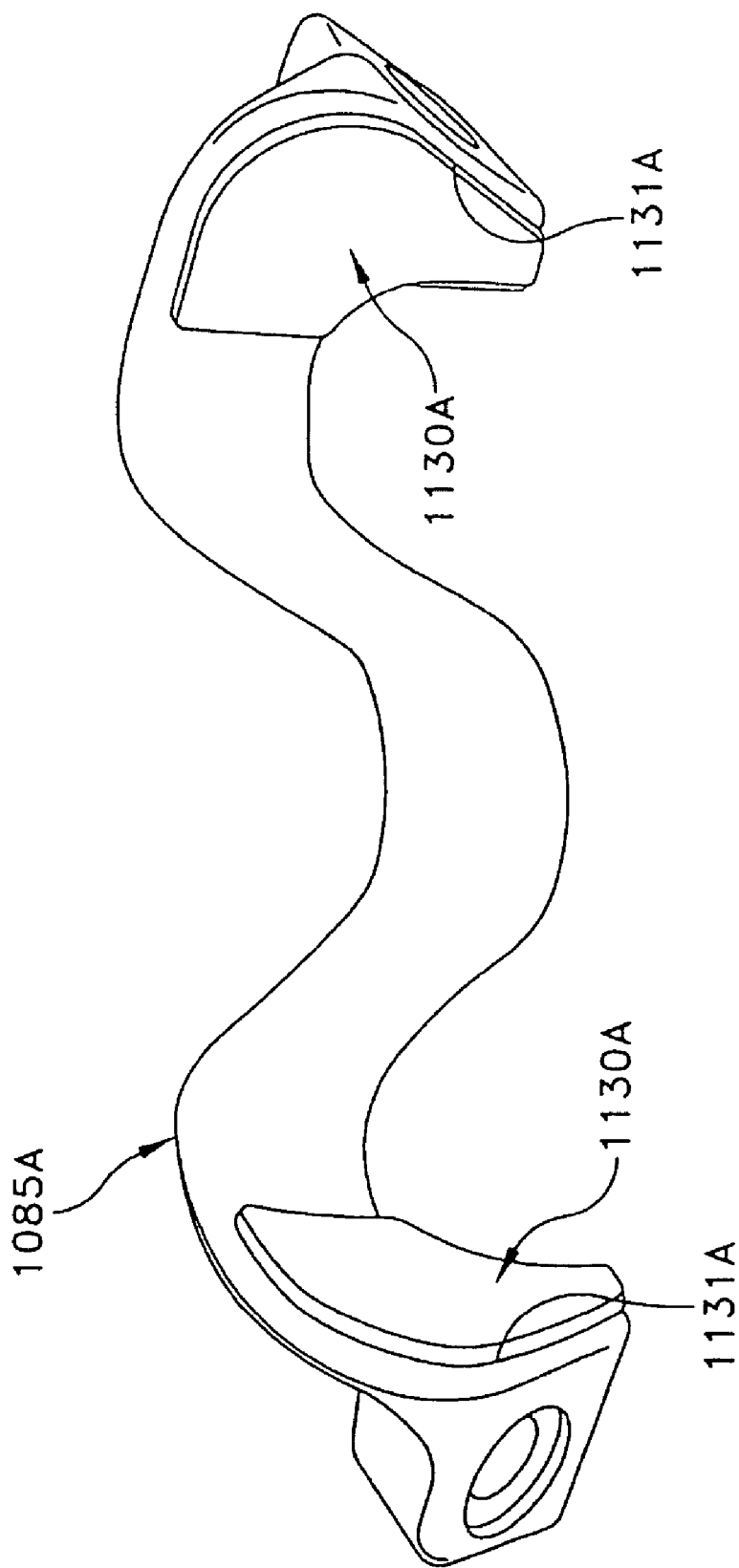
FIG. 27 is a perspective view of an alternative embodiment of the superior bilateral facet prosthesis shown in FIGS. 24 and 25.

FIG. 27 illustrates an alternative superior facet prosthesis 1085A with a bearing surface 1130A that mounts to substrate 1131A. The bearing surface 1130A is preferably a biocompatible polymeric material, such as ultra high molecular weight polyethylene. Alternately, the bearing surface 1130A can be ceramic, such as zirconia or alumina. The substrate 1131A is preferably a biocompatible metal alloy, such as an alloy of titanium, cobalt, or iron.

Figure 28:
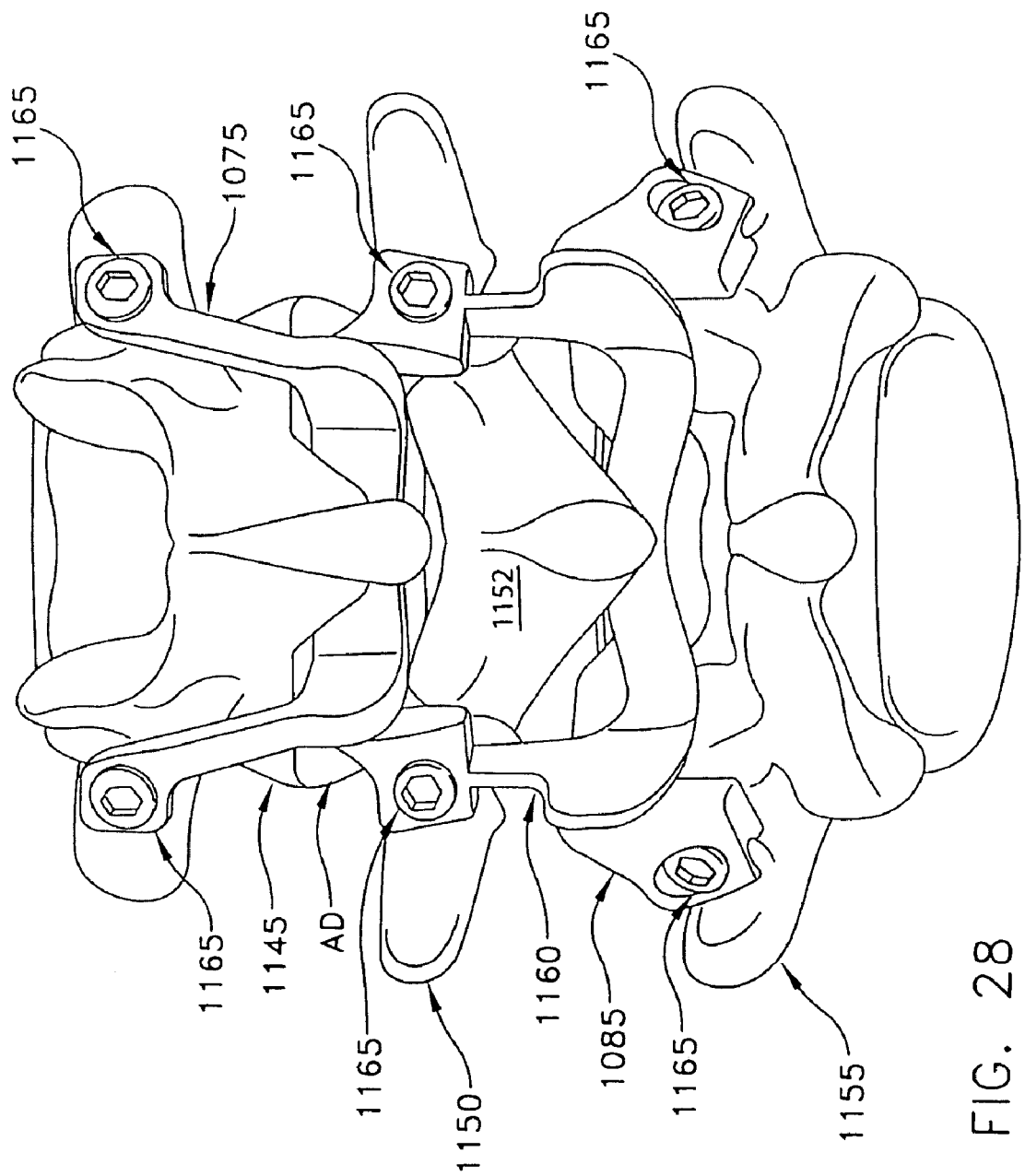
FIG. 28 is a dorsal view of a two level facet joint replacement.

FIG. 28 illustrates a superior vertebra 1145, a middle vertebra 1150, and an inferior vertebra 1155. Superior facet prosthesis 1085 articulates with quad-facet prosthesis 1160 to recreate the natural biomechanics of the replaced facet joints. Inferior facet prosthesis 1075 articulates with quad-facet prosthesis 1160 to recreate the natural biomechanics of the replaced facet joints at the next upper level. Thus, FIG. 28 illustrates a two level reconstruction of facet joints. Superior facet prosthesis 1085, quad-facet prosthesis 1160, and inferior facet prosthesis 1075 are each attached to bone by means of screw fasteners 1165.

Figure 29:
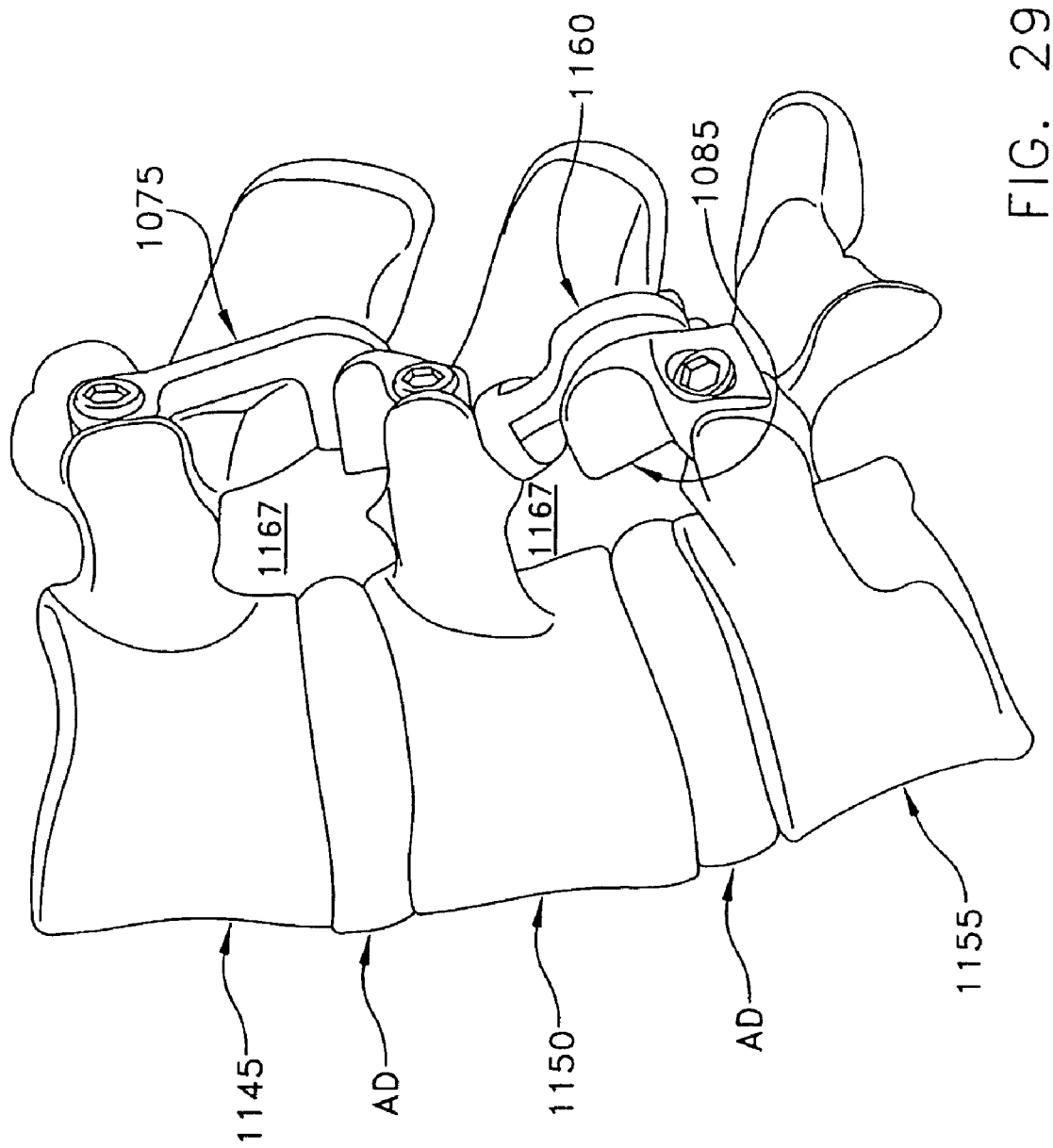
FIG. 29 is a lateral view of the two level facet joint replacement of FIG. 28.

In the lateral view of FIG. 29, it can be appreciated that superior facet prosthesis 1085, quad-facet prosthesis 1160, and inferior facet prosthesis 1075 do not encroach into the intervertebral foraminal spaces 1167 where nerve roots extend laterally from the spinal cord.

Figure 30:
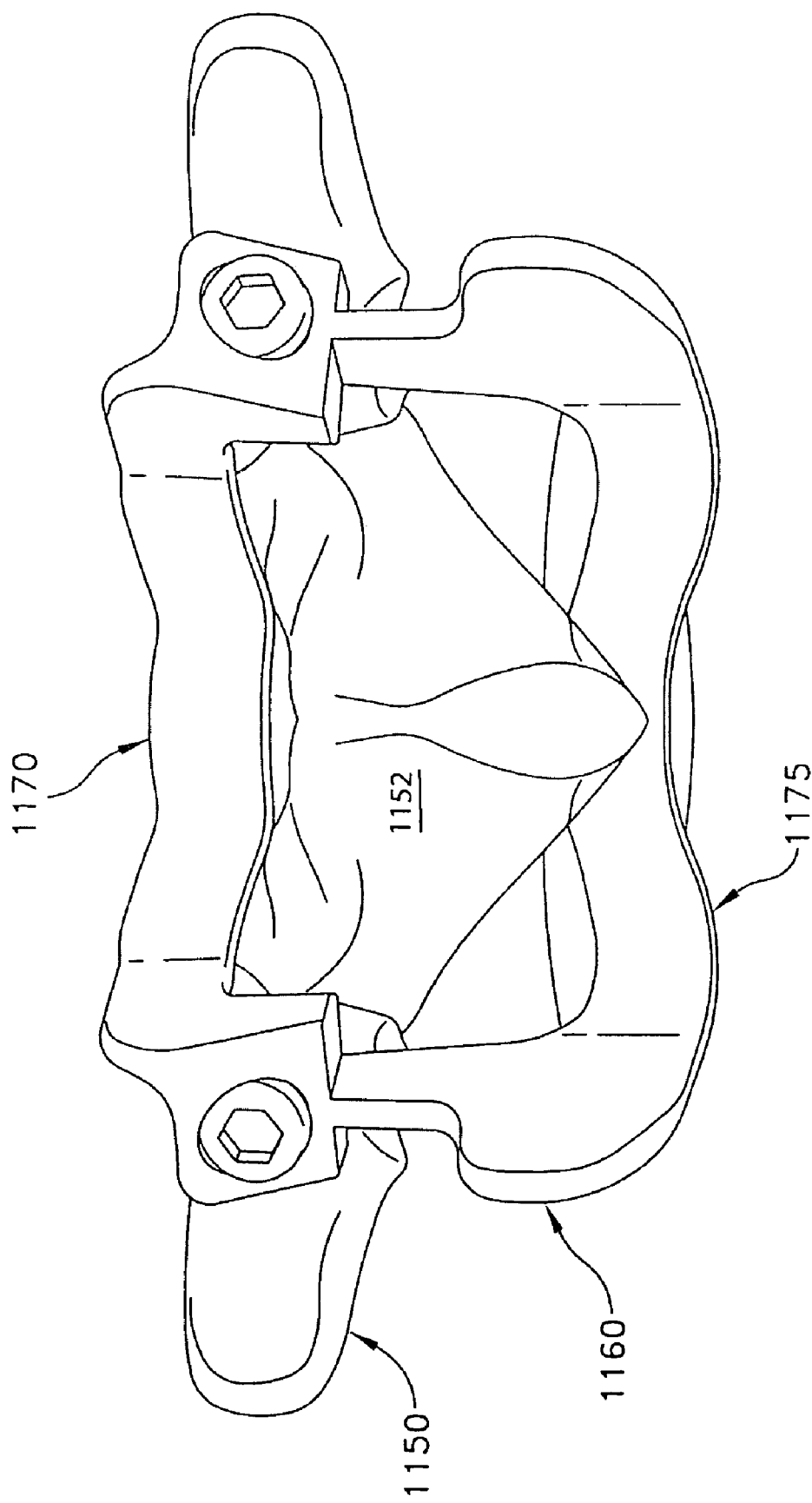
FIG. 30 is a dorsal view of the implanted four facet prosthesis shown in FIGS. 28 and 29.
Figure 31:
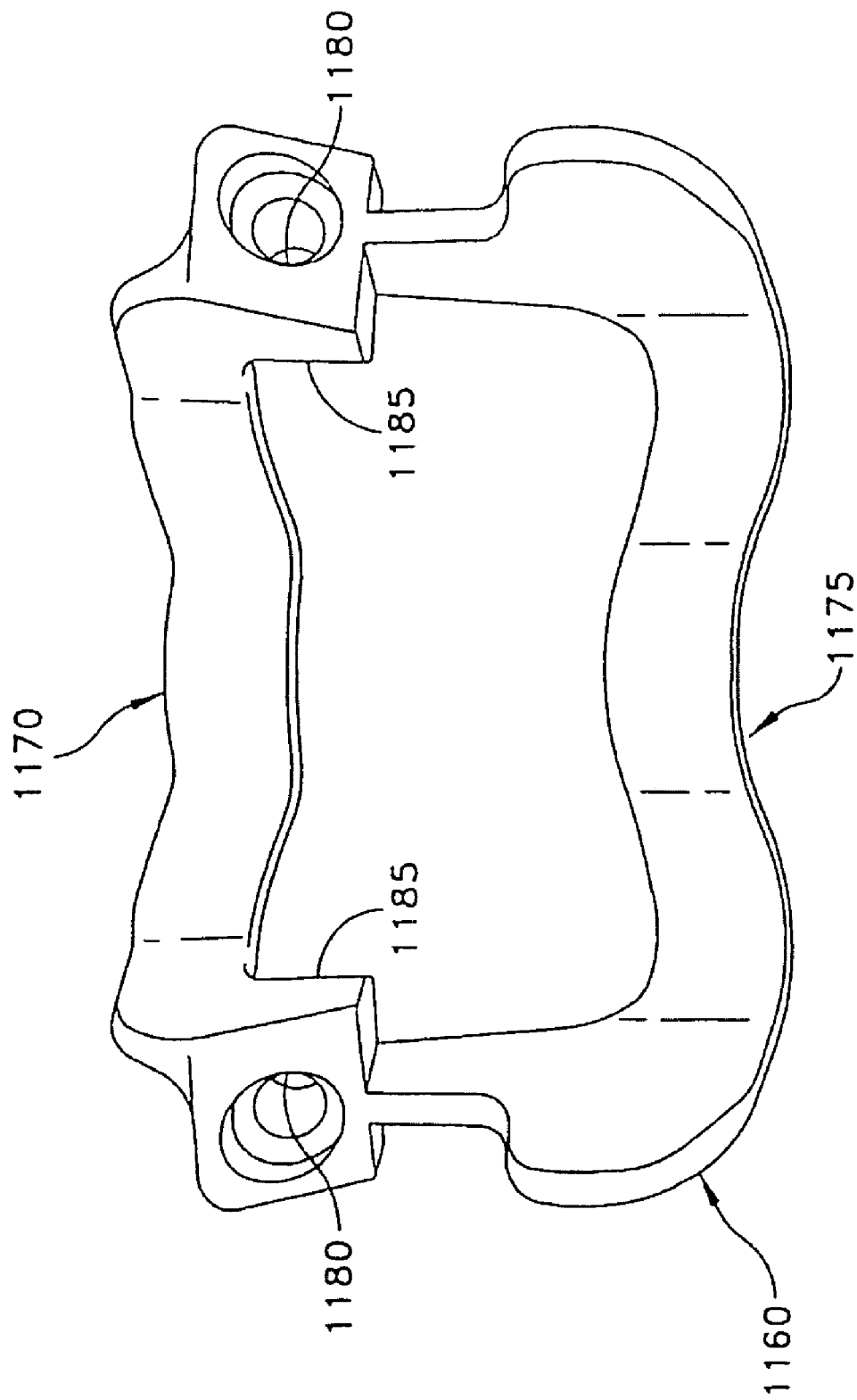
FIG. 31 is a perspective view of the four facet prosthesis shown in FIG. 30.

Referring next to FIG. 30, it should be appreciated that superior bridge 1170 and inferior bridge 1175 of quad-facet prosthesis 1160 do not contact any portion of the lamina 1152 of vertebra 1150. Mounting holes 1180 (shown in FIG. 31) are used to secure the flanges 1185 against the pedicles of vertebra 1150.

Figure 32:
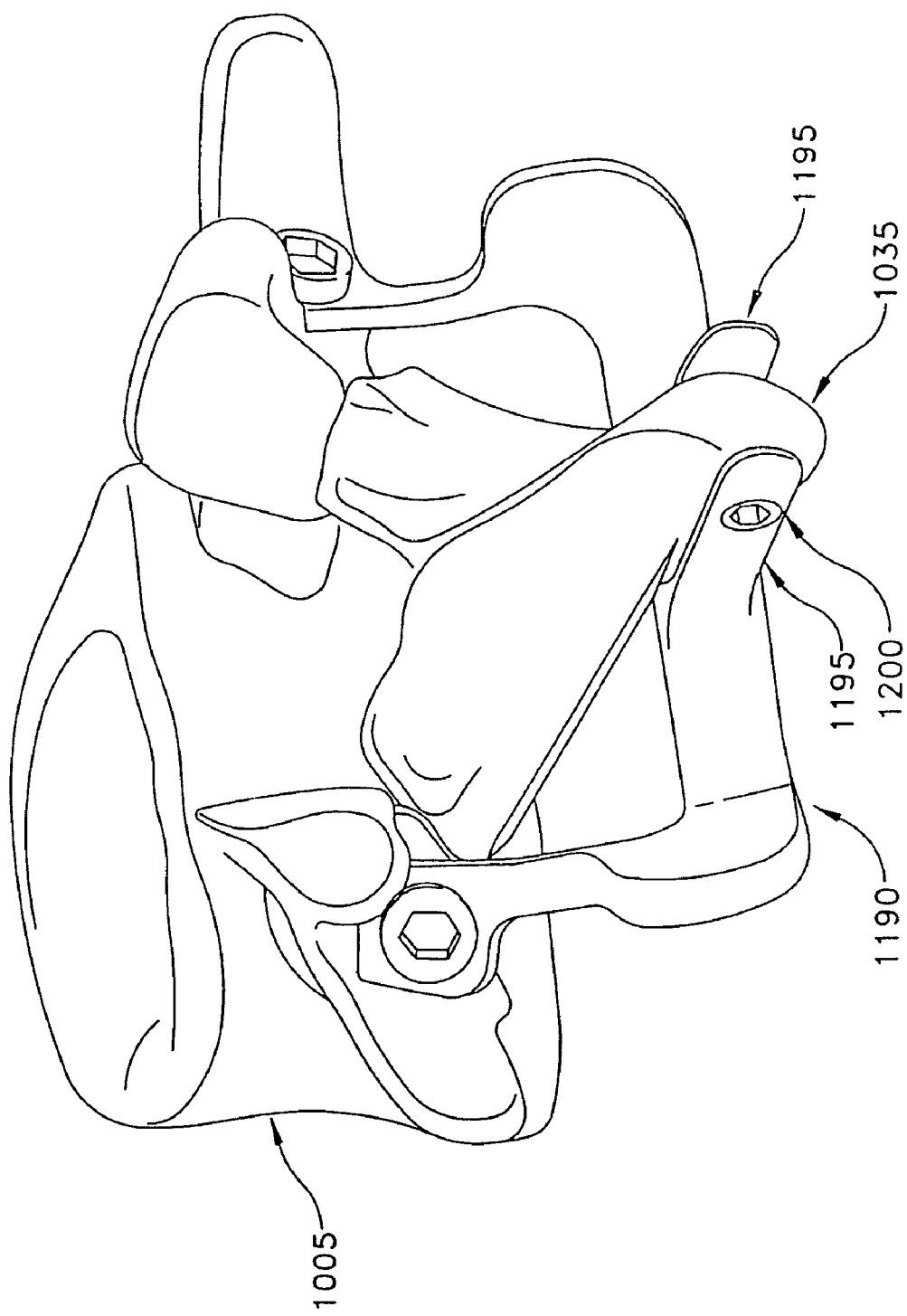
FIG. 32 is a perspective view of an alternative form of inferior bilateral facet prosthesis.

In FIG. 32, an alternative inferior bilateral facet prosthesis 1190 is presented. To further stabilize the implant and to counter moments that act upon the two points of fixation into the pedicles, a set of parallel flanges 1195 extend posteriorly such that the two flanges straddle the spinous process 1035. A bolt 1200 is used to fasten the parallel flanges to the spinous process. Alternatively, other adjunctive structural features could be added to further stabilize the prosthesis. For example, a strut that extends, and attaches, to the transverse process could be used to further stabilize the prosthesis.

Figure 33:
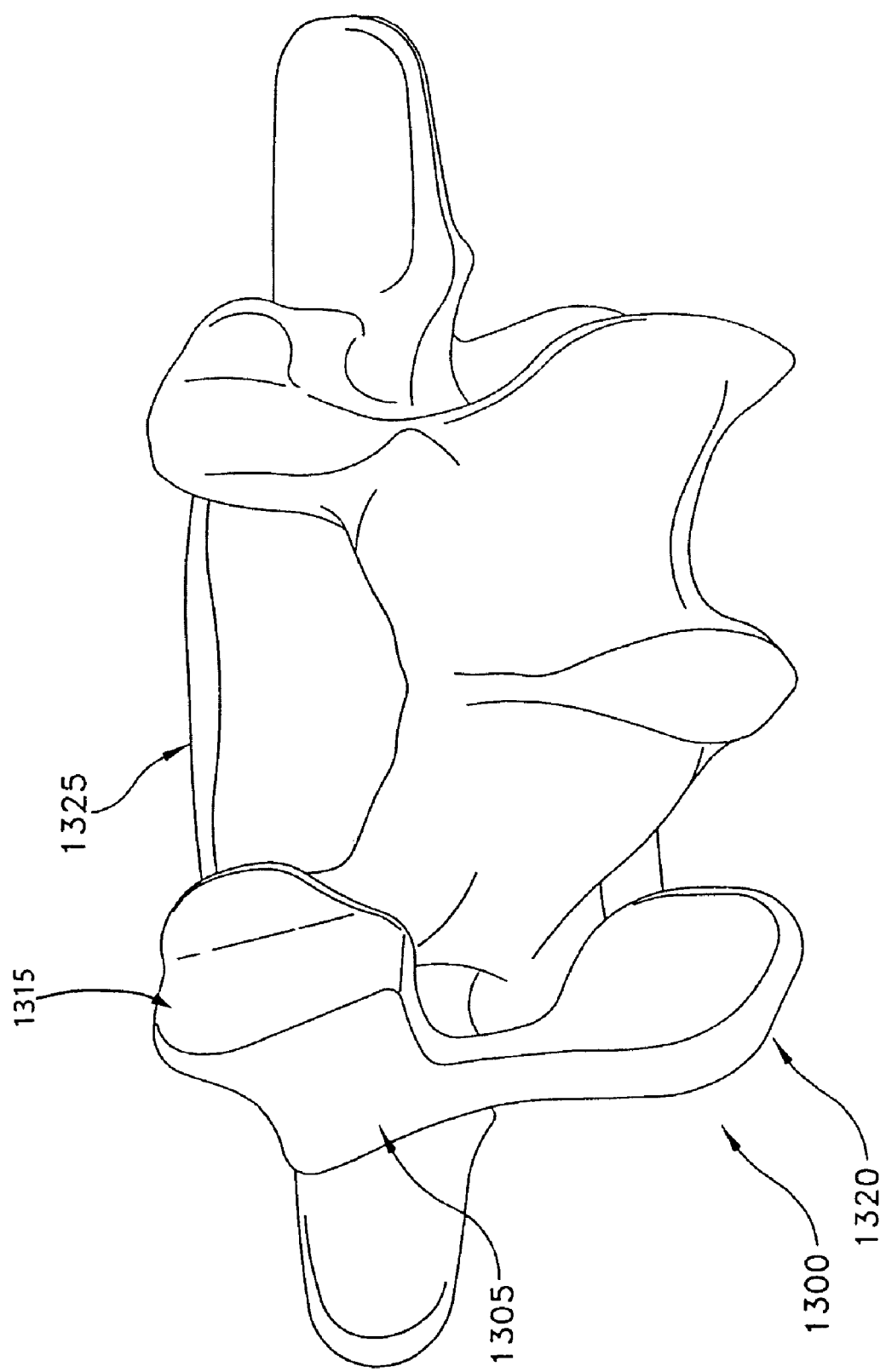
FIG. 33 is a perspective view of an implanted superior and inferior unilateral facet prosthesis.
Figure 34:
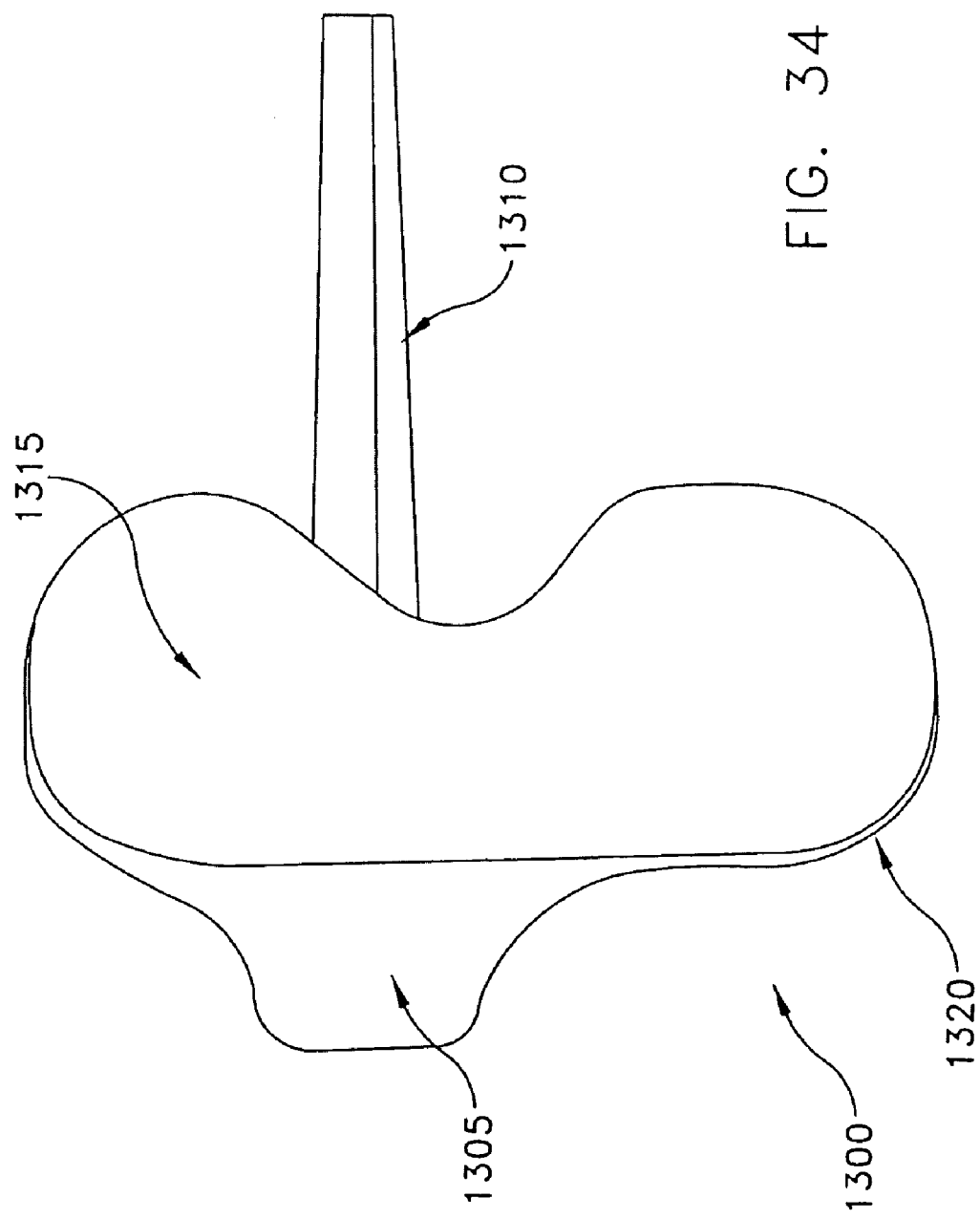
FIG. 34 is a perspective view of the unilateral facet prosthesis shown in FIG. 33.

Looking next at FIGS. 33 and 34, there is shown a superior and inferior unilateral facet prosthesis 1300. Unilateral facet prosthesis 1300 comprises a body 1305 and a stem 1310 extending out of body 1305. A superior element 1315 extends vertically upward from body 1305, and an inferior element 1320 extends vertically downward from body 1305. Unilateral facet prosthesis 1300 is configured so that when its stem 1310 extends into the pedicle of vertebra 1325, superior element 1315 will replace a resected superior facet, and inferior element 1320 will replace a resected inferior facet. If desired, stem 1310 could be replaced with a screw extending through a hole in body 1305 and into the pedicle.

Disc Prosthesis and Quadruple Facet Prosthesis

Figure 35:
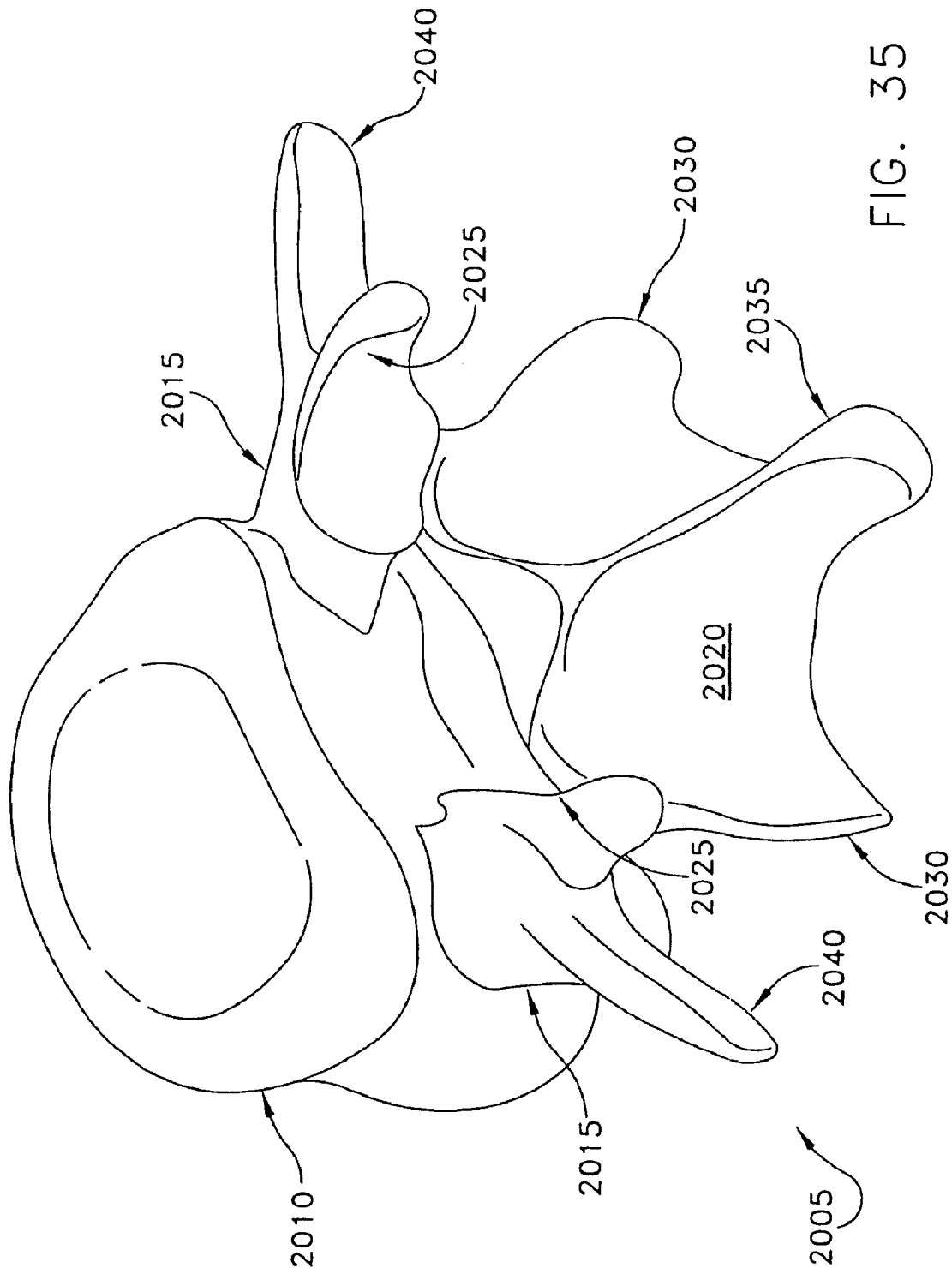
FIG. 35 is a perspective view of a lumbar vertebra.

Referring next to FIG. 35, there is shown a natural lumbar vertebra 2005 comprising a natural vertebral body 2010, a pair of natural pedicles 2015 extending from natural vertebral body 2010, a natural lamina 2020 extending from natural pedicles 2015, a pair of natural superior facets 2025 extending from natural pedicles 2015 and natural lamina 2020, a pair of natural inferior facets 2030 extending from natural lamina 2020, a natural spinous process 2035 extending from natural lamina 2020, and a pair of natural transverse processes 2040 extending from natural pedicles 2015.

In accordance with another aspect of the invention, the intervertebral disc on one side or the other of vertebral body 2010 is replaced by an artificial disc. This artificial disc may be a device such as is described by Stefee et al. in U.S. Pat. No. 5,071,437; Gill et al in U.S. Pat. No. 6,113,637; Bryan et al. in U.S. Pat. No. 6,001,130; Hedman et al. in U.S. Pat. No. 4,759,769; Ray in U.S. Pat. No. 5,527,312; Ray et al. in U.S. Pat. No. 5,824,093; Buttner-Janz in U.S. Pat. No. 5,401,269; and Serhan et al. in U.S. Pat. No. 5,824,094; all which documents are hereby incorporated herein by reference. Alternatively, the artificial disc may be some other artificial disc of the sort known in the art.

Figure 36:
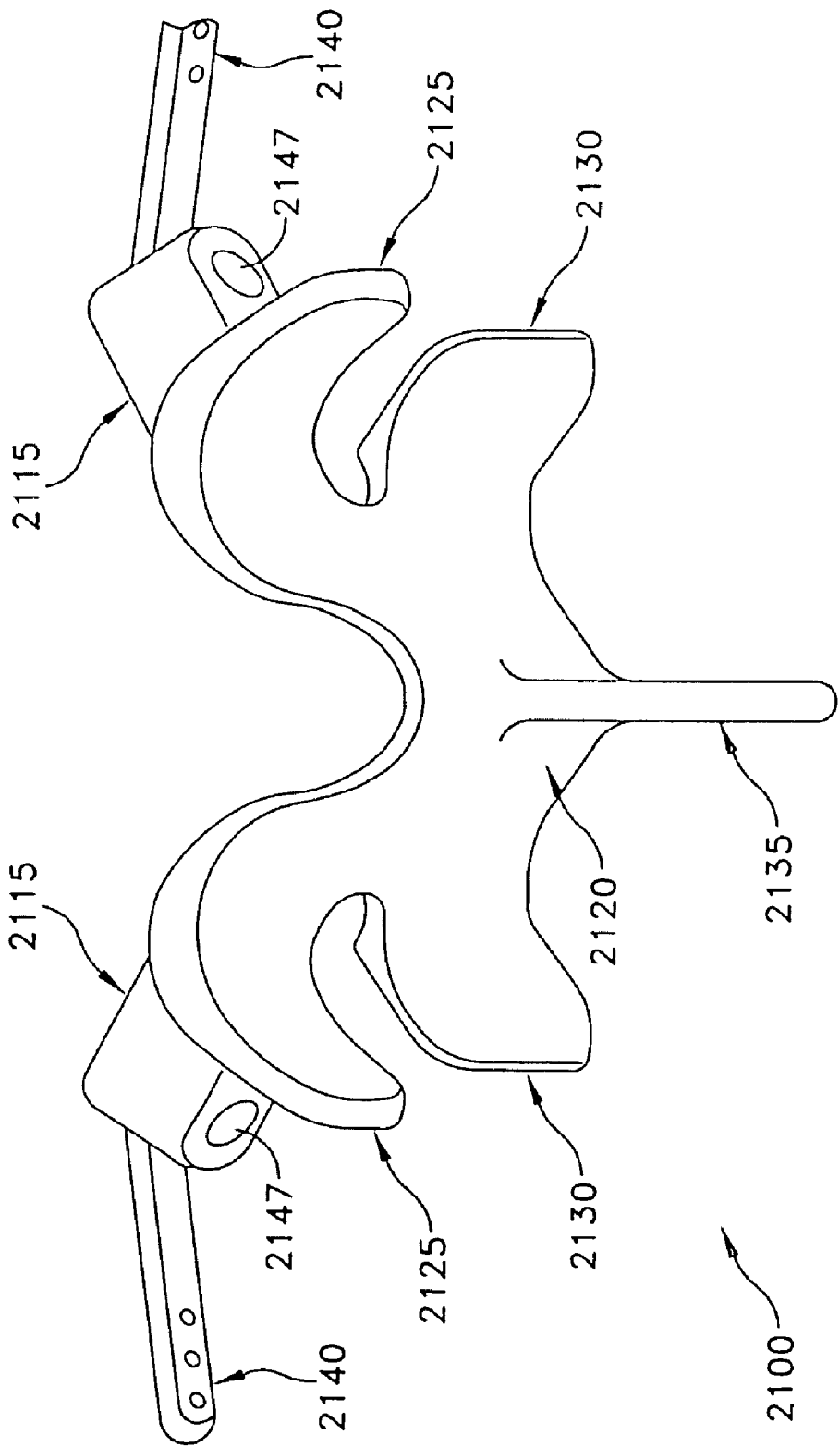
FIG. 36 is a perspective view of a novel prosthesis that replaces the lamina, the four facets, the spinous process and the two transverse processes of a vertebra.
Figure 37:
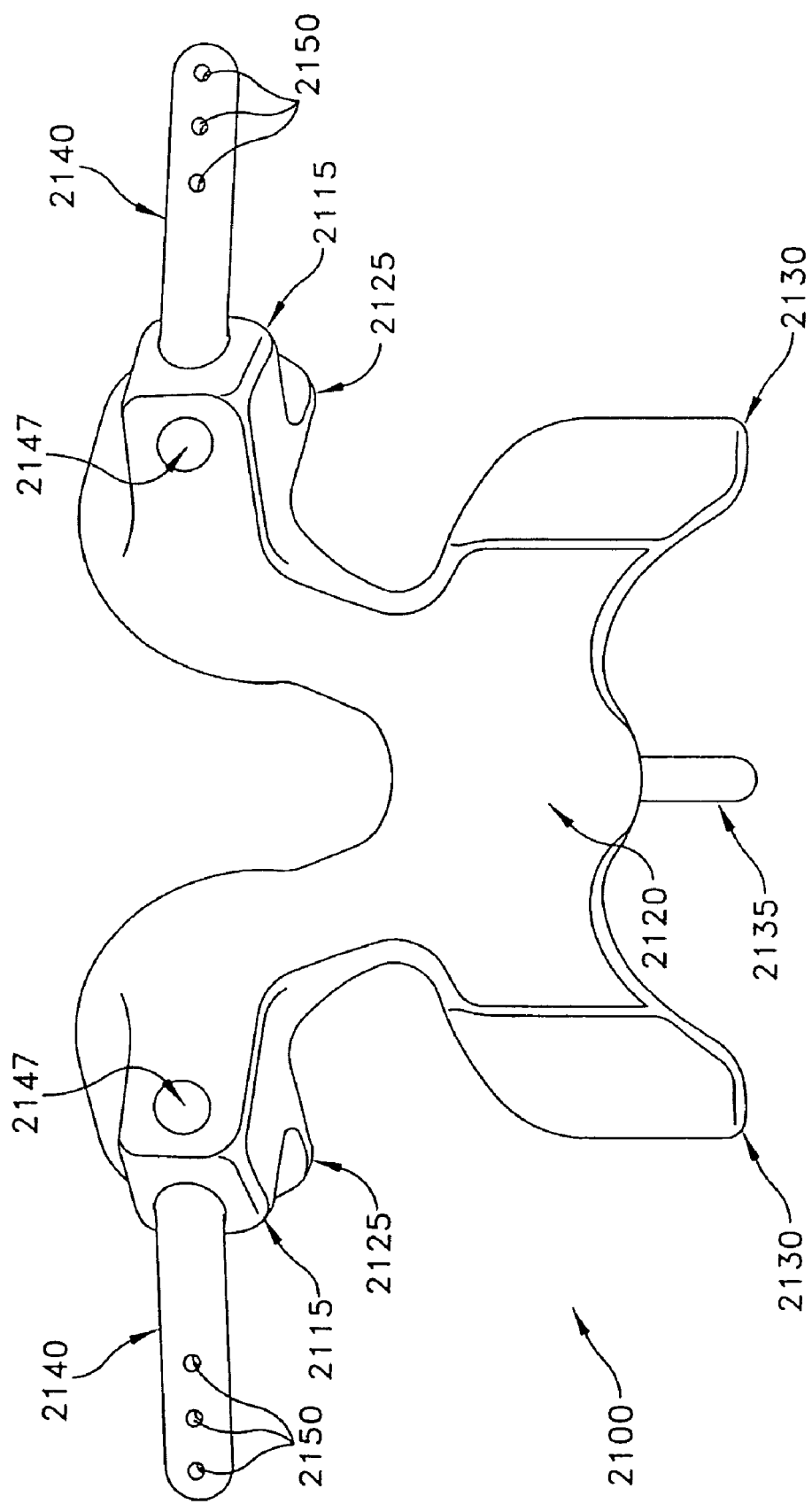
FIG. 37 is an anterior view of the prosthesis shown in FIG. 36.

In addition to the foregoing, and looking next at FIGS. 36 and 37, there is shown a novel prosthesis 2100 which is adapted to replace the natural lamina 2020, the two natural superior facets 2025, the two natural inferior facets 2030, the natural spinous process 2035, and the two natural transverse processes 2040. To this end, prosthesis 2100 comprises a pair of prosthetic mounts 2115, a prosthetic lamina 2120 extending from prosthetic mounts 2115, a pair of prosthetic superior facets 2125 extending from prosthetic mounts 2115 and prosthetic lamina 2120, a pair of prosthetic inferior facets 2130 extending from prosthetic lamina 2120, a prosthetic spinous process 2135 extending from prosthetic lamina 2120, and a pair of prosthetic transverse processes 2140 extending from prosthetic mounts 2115.

Figure 38:
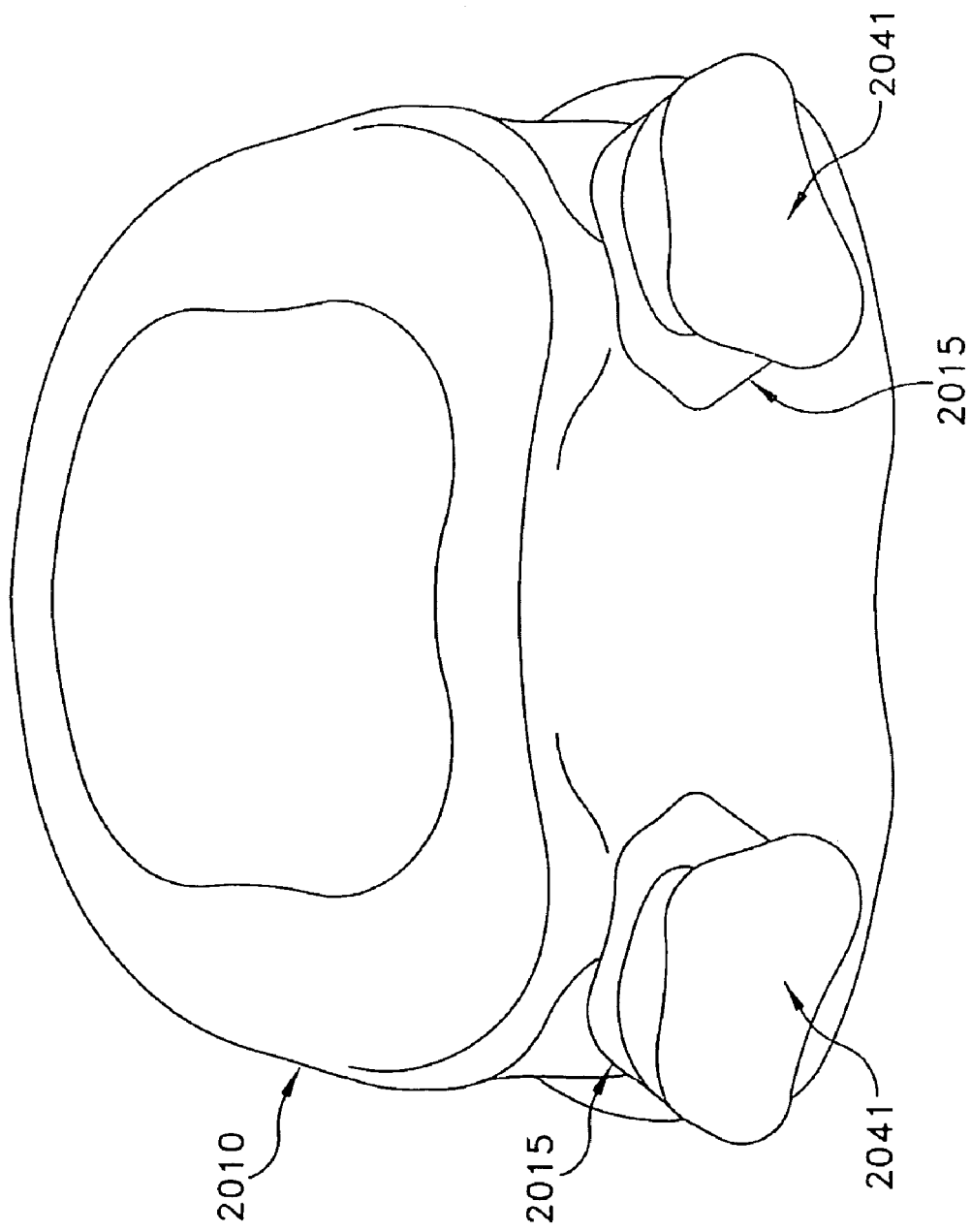
FIG. 38 is a perspective view of a vertebra which has been resected to receive the prosthesis shown in FIG. 36
Figure 39:
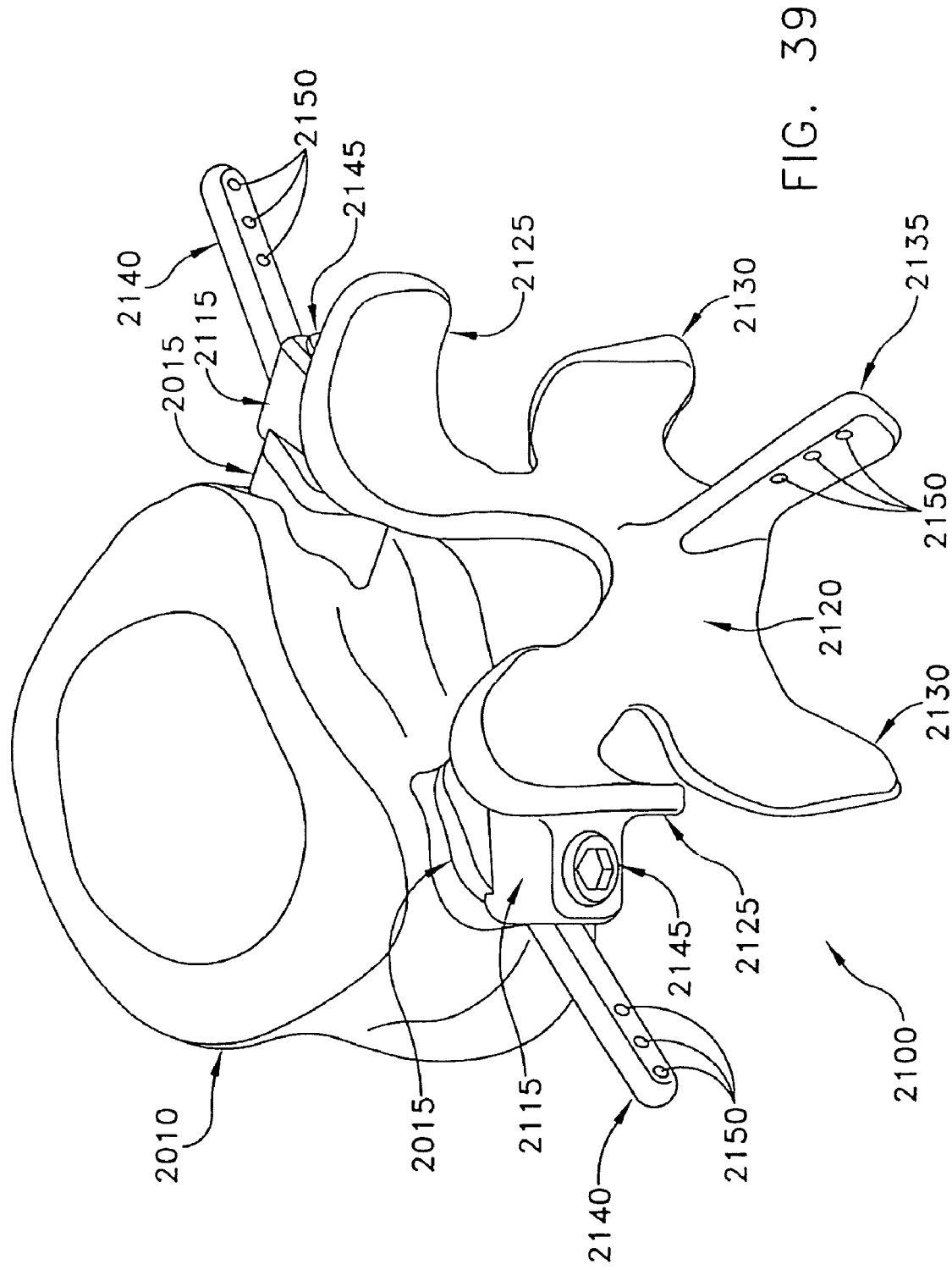
FIG. 39 is a perspective view of the prosthesis shown in FIG. 36 mounted to the resected vertebra shown in FIG. 38.
Figure 40:
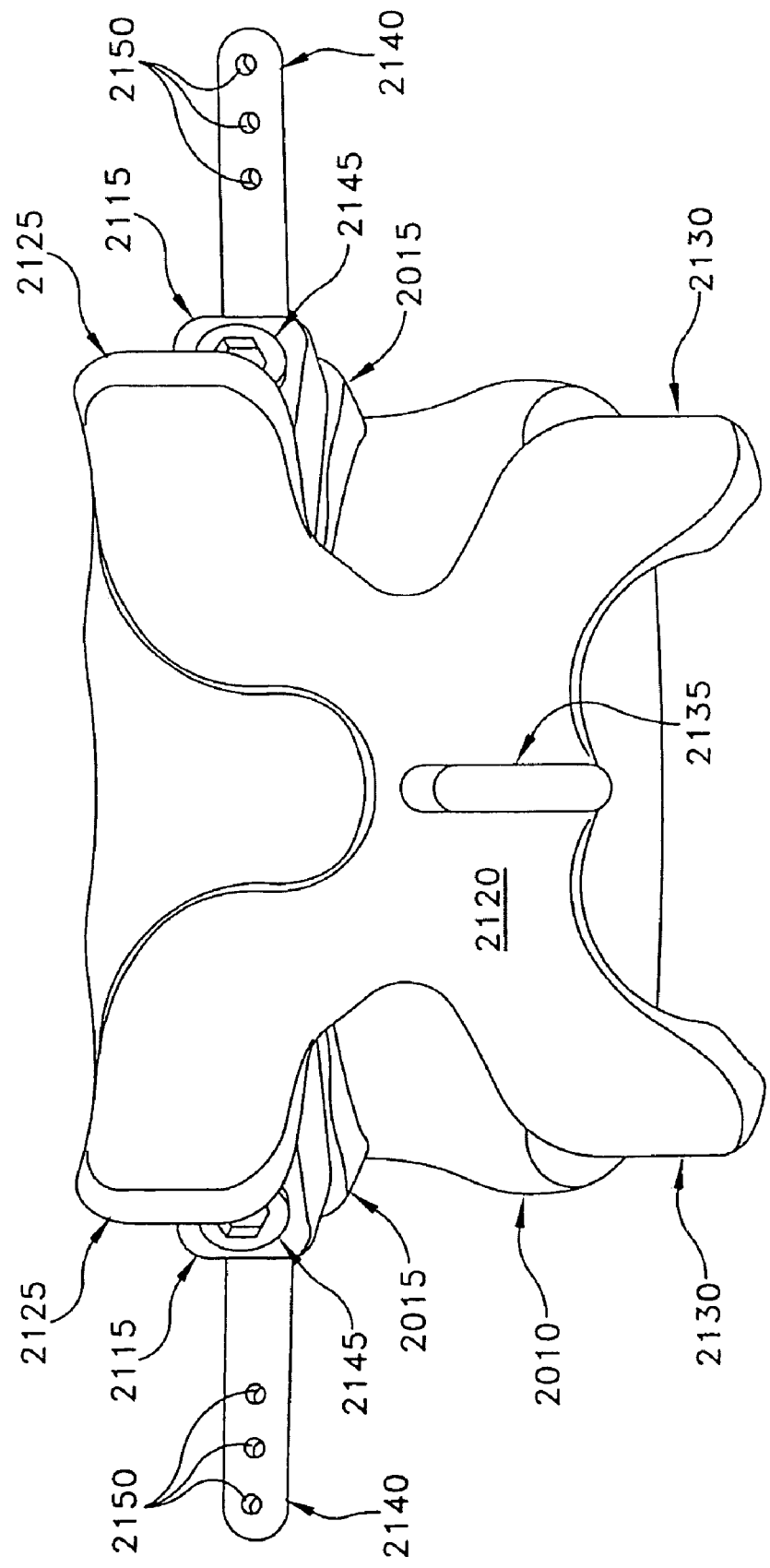
FIG. 40 is a dorsal view of the prosthesis shown in FIG. 36 mounted to the resected H vertebra shown in FIG. 38.
Figure 41:
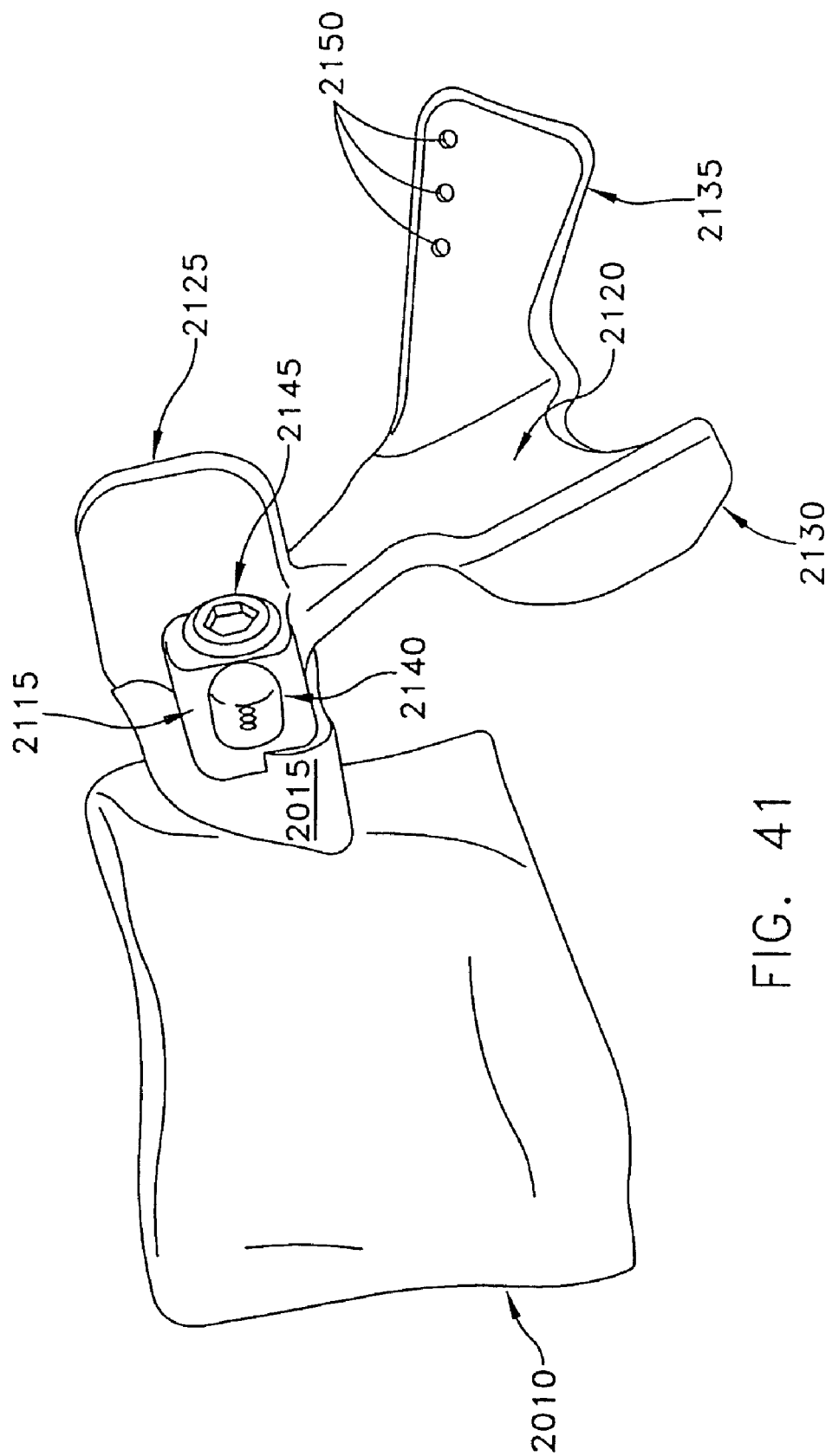
FIG. 41 is a lateral view of the prosthesis shown in FIG. 36 mounted to the resected vertebra shown in FIG. 38.

In the use of prosthesis 2100, natural lumbar vertebra 2005 is resected at its natural pedicles 2015 so as to remove the natural lamina 2020, the two natural superior facets 2025, the two natural inferior facets 2030, the natural spinous process 2035, and the two natural transverse processes 2040, leaving a pair of pedicle end surfaces 2041 (FIG. 38). Then the prosthesis 2100 may be attached to the natural pedicles 2015, e.g., by placing prosthetic mounts 2115 against pedicle surfaces 2041 and then passing screws 2145 through screw holes 2147 and into natural pedicles 2015, as shown in FIGS. 39-41. As seen in the drawings, the relative size, shape and positioning of the prosthetic lamina 2120, the two prosthetic superior facets 2125, the two prosthetic inferior facets 2130, the prosthetic spinous process 2135, and the two prosthetic transverse processes 2140 essentially mimic the relative size, shape and positioning of the natural lamina 2020, the two natural superior facets 2025, the two natural inferior facets 2030, the natural spinous process 2035, and the two natural transverse processes 2040, whereby to effectively restore the vertebra. If desired, holes 2150 may be provided in the prosthetic spinous process 2135 and/or the two prosthetic transverse processes 2140 so as to facilitate re-attaching soft tissue to these structures.

Figure 42:
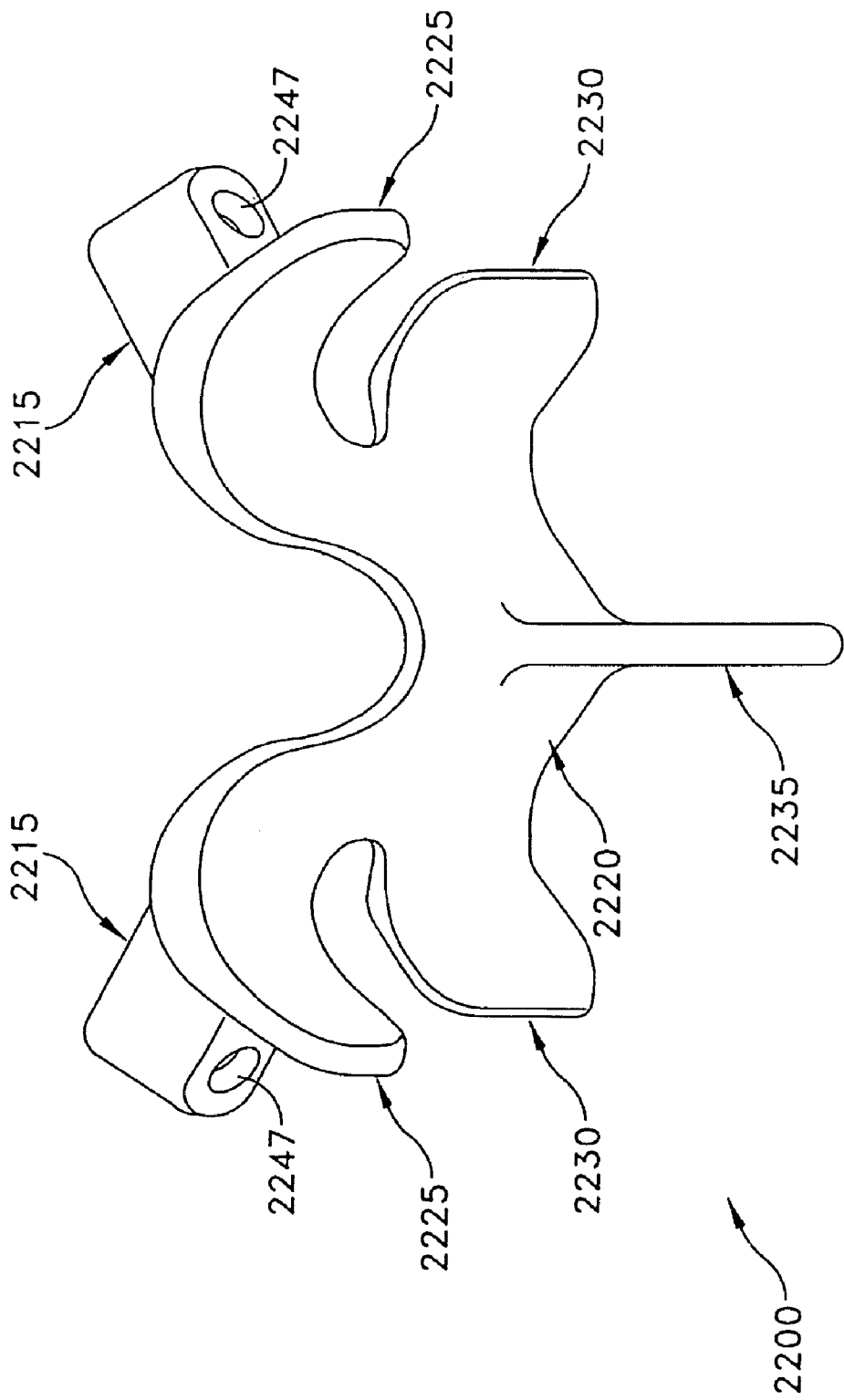
FIG. 42 is a perspective view of a novel prosthesis that replaces the lamina, the four facets and the spinous process of a vertebra.

Looking next at FIG. 42, there is shown a novel prosthesis 2200 which is adapted to replace natural lamina 2020, the two natural superior facets 2025, the two natural inferior facets 2030, and natural spinous process 2035. To this end, prosthesis 2200 comprises a pair of prosthetic mounts 2215, a prosthetic lamina 2220 extending from prosthetic mounts 2215, a pair of prosthetic superior facets 2225 extending from prosthetic mounts 2215 and prosthetic lamina 2220, a pair of prosthetic inferior facets 2230 extending from prosthetic lamina 2220, and a prosthetic spinous process 2235 extending from prosthetic lamina 2220.

In the use of prosthesis 2200, natural lumbar vertebra 2005 is resected at its natural pedicles 2015 so as to remove the natural lamina 2020, the two natural superior facets 2025, the two natural inferior facets 2030, the spinous process 2035 and the two natural transverse processes 2040, leaving a pair of pedicle surfaces 2041 (FIG. 38). Then the prosthesis 2200 may be attached to the natural pedicles 2015, e.g., by placing prosthetic mounts 2215 against pedicle surfaces 2041 and then passing screws 2145 through holes 2247 and into natural pedicles 2015. As seen in the drawing, the relative size, shape and positioning of prosthetic lamina 2220, the two prosthetic superior facets 2225, the two prosthetic inferior facets 2230, and the prosthetic spinous process 2235 essentially mimic the relative size, shape and positioning of the natural lamina 2020, the two natural superior facets 2025, the two natural inferior facets 2030, and the natural spinous process 2035, whereby to effectively restore the vertebra. If desired, holes 2150 may be provided in the prosthetic spinous process 2235 so as to facilitate re-attaching soft tissue to this structure.

Figure 43:
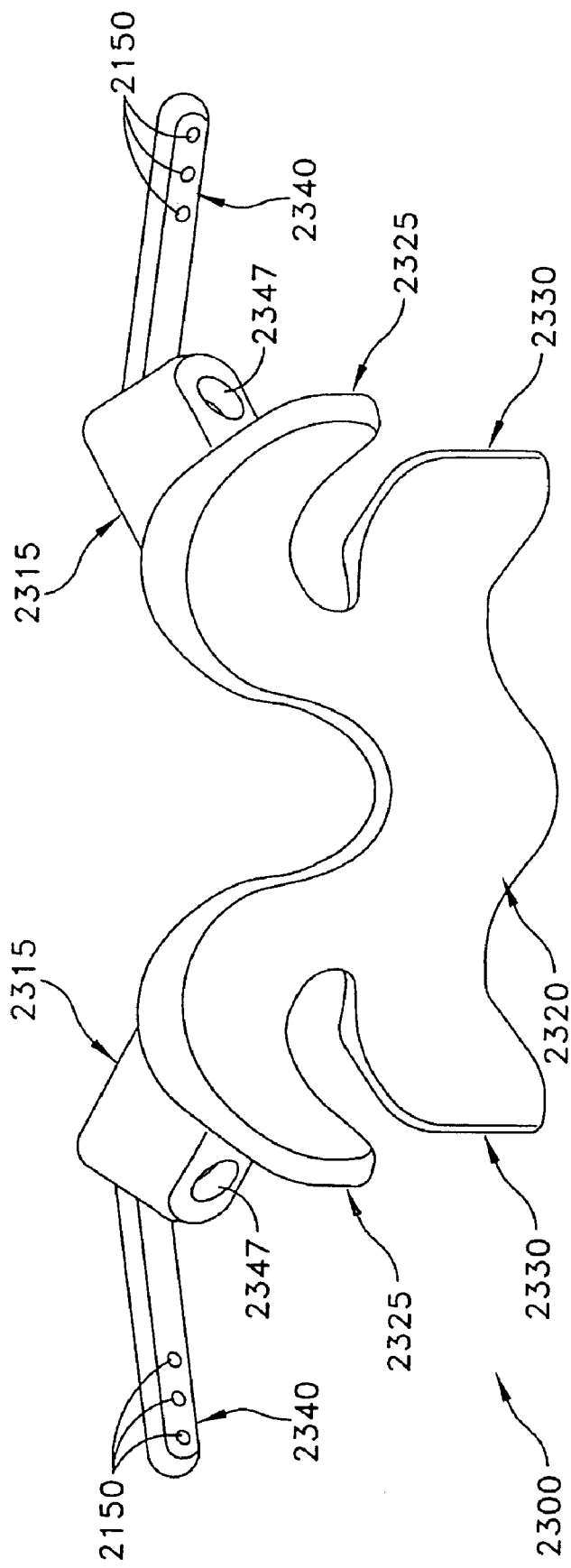
FIG. 43 is a perspective view of a novel prosthesis that replaces the lamina, the four facets and the two transverse processes of a vertebra.

Looking next at FIG. 43, there is shown a novel prosthesis 2300 which is adapted to replace the natural lamina 2020, the two natural superior facets 2025, the two natural inferior facets 2030, and the two natural transverse processes 2040. To this end, prosthesis 2300 comprises a pair of prosthetic mounts 2315, a prosthetic lamina 2320 extending from prosthetic mounts 2315, a pair of prosthetic superior facets 2325 extending from prosthetic mounts 2315 and prosthetic lamina 2320, a pair of prosthetic inferior facets 2330 extending from prosthetic lamina 2320, and a pair of prosthetic transverse processes 2340 extending from prosthetic mounts 2315.

In the use of prosthesis 2300, natural lumbar vertebra 2005 is resected at natural pedicles 2015 so as to remove natural lamina 2020, the two natural superior facets 2025, the two natural inferior facets 2030, the natural spinous process 2035 and the two natural transverse processes 2040, leaving a pair of pedicle surfaces 2041 (FIG. 38). Then the prosthesis 2300 may be attached to the natural pedicles 2015, e.g., by placing prosthetic mounts 2315 against pedicle surfaces 2041 and then passing screws 2145 through holes 2347 and into natural pedicles 2015. As seen in the drawing, the relative size, shape and positioning of the prosthetic lamina 2320, the two prosthetic superior facets 2325, the two prosthetic inferior facets 2330, and the two prosthetic transverse processes 2340 essentially mimic the relative size, shape and positioning of the natural lamina 2020, the two natural superior facets 2025, the two natural inferior facets 2030, and the two natural transverse processes 2040, whereby to effectively restore the vertebra. If desired, holes 2150 may be provided in the two prosthetic transverse processes 2340 so as to facilitate re-attaching soft tissue to these structures.

Figure 44:
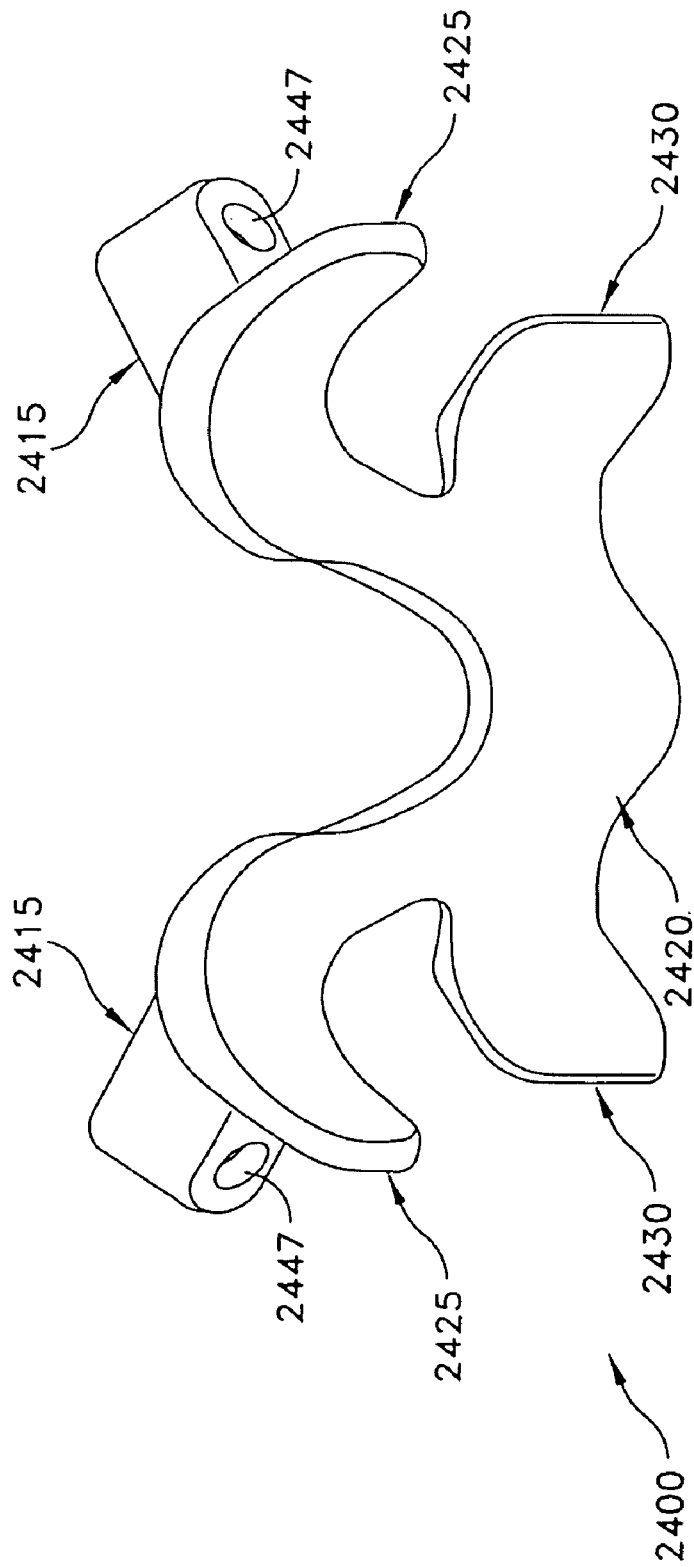
FIG. 44 is a perspective view of a novel prosthesis that replaces the lamina and the four facets of a vertebra.

Looking next at FIG. 44, there is shown a novel prosthesis 2400 which is adapted to replace the natural lamina 2020, the two natural superior facets 2025, and the two natural inferior facets 2030. To this end, prosthesis 2400 comprises a pair of prosthetic mounts 2415, a prosthetic lamina 2420 extending from prosthetic mounts 2415, a pair of prosthetic superior facets 2425 extending from prosthetic mounts 2415 and prosthetic lamina 2420, and a pair of prosthetic inferior facets 2430 extending from prosthetic lamina 2420.

In the use of prosthesis 2400, natural lumbar vertebra 2005 is resected at pedicles 2015 so as to remove the natural lamina 2020, the two natural superior facets 2025, the two natural inferior facets 2030, the natural spinous process 2035, and the two natural transverse processes 2040, leaving a pair of pedicle surfaces 2041 (FIG. 38). Then the prosthesis 2400 may be attached to the natural pedicles 2015, e.g., by placing prosthetic mounts 2415 against pedicle surfaces 2041 and then passing screws 2145 through holes 2447 and into natural pedicles 2015. As seen in the drawing, the relative size, shape and positioning of prosthetic lamina 2420, the two prosthetic superior facets 2425, and the two prosthetic inferior facets 2430 essentially mimic the relative size, shape and positioning of the natural lamina 2020, the two natural superior facets 2025 and the two natural inferior facets 2030, whereby to effectively restore the vertebra.

Figure 45:
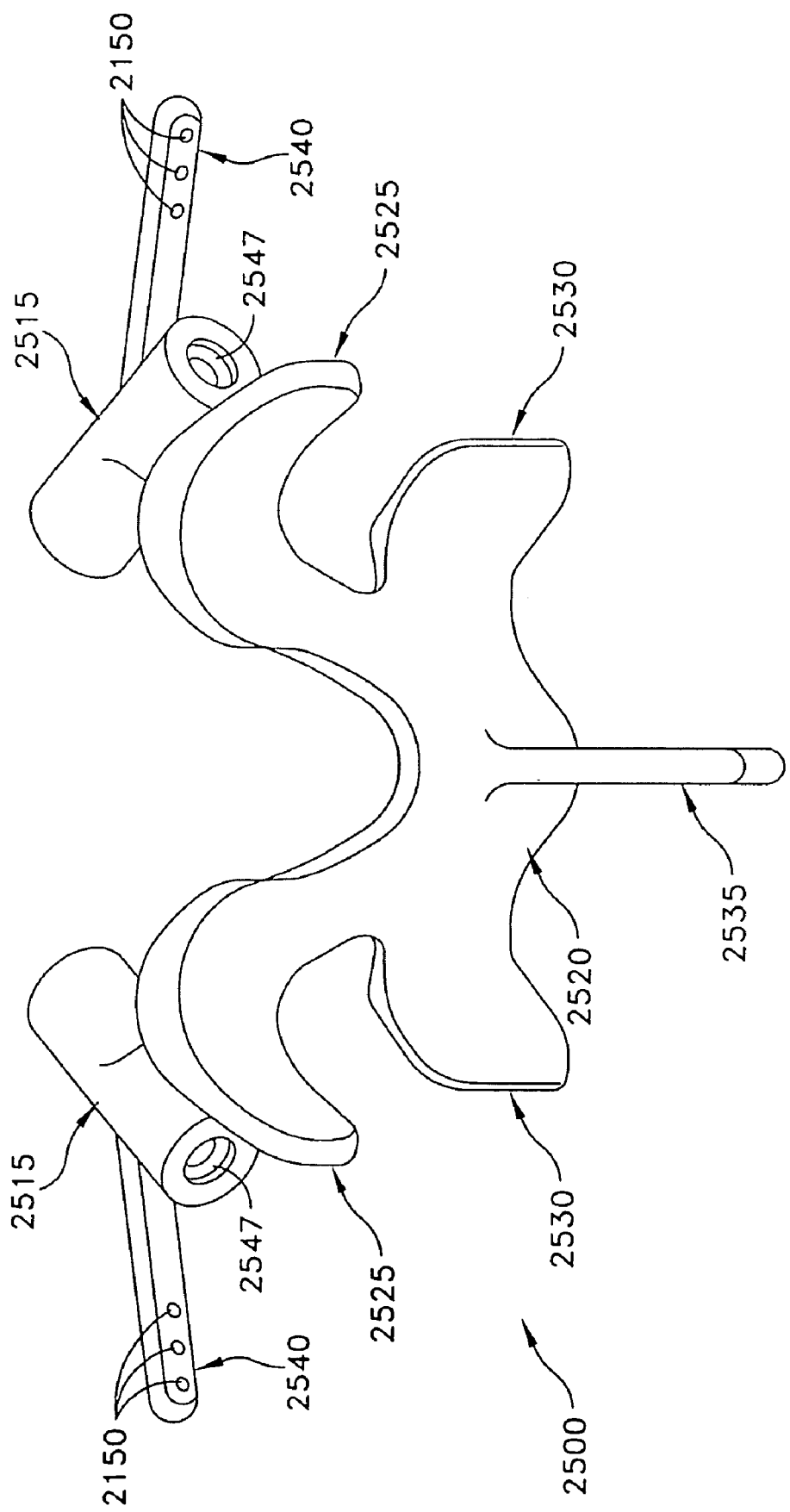
FIG. 45 is a perspective view of a novel prosthesis that replaces the two pedicles, the lamina, the four facets, the spinous process and the two transverse processes of a vertebra.
Figure 46:
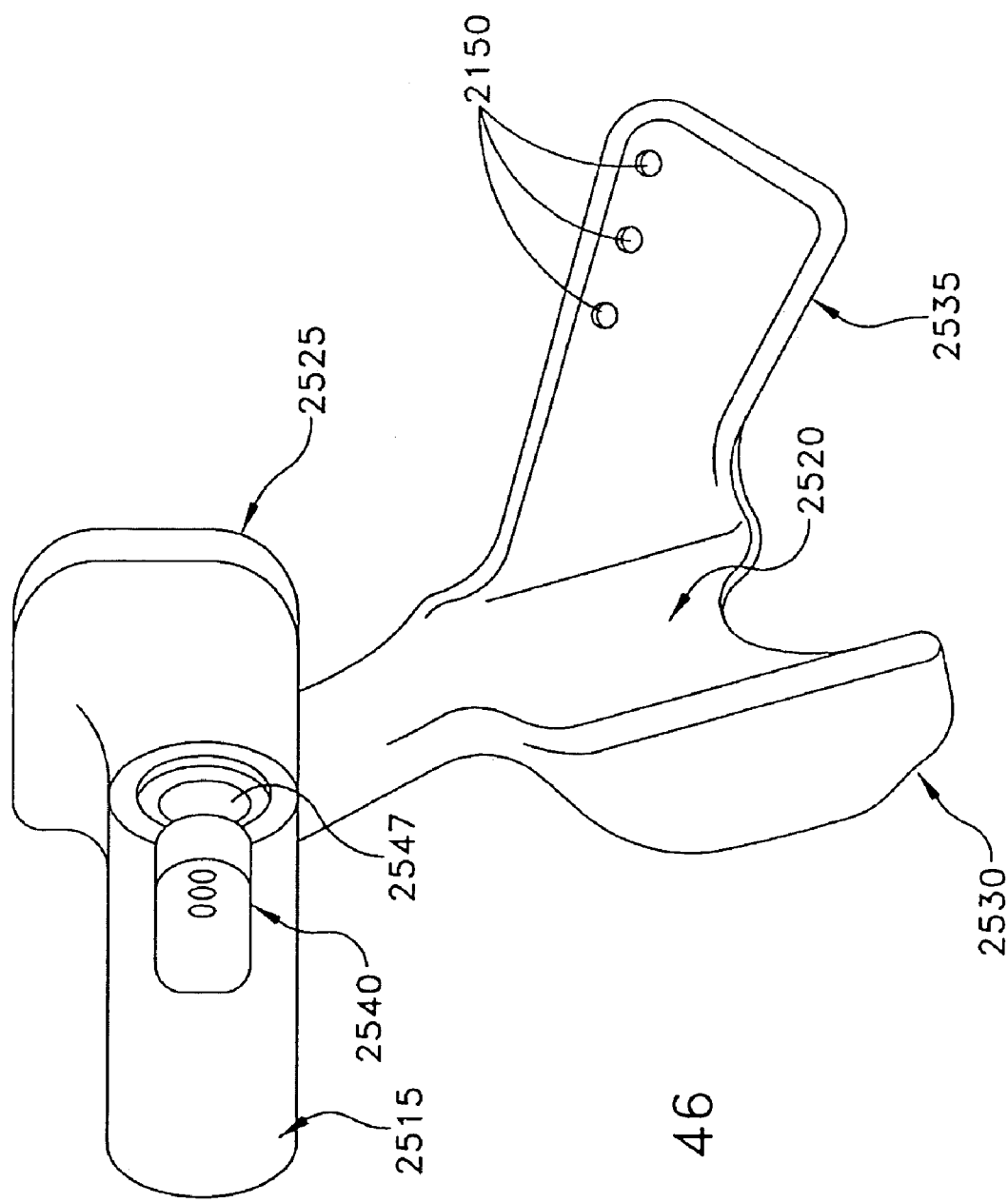
FIG. 46 is a lateral view of the prosthesis shown in FIG. 45.
Figure 47:
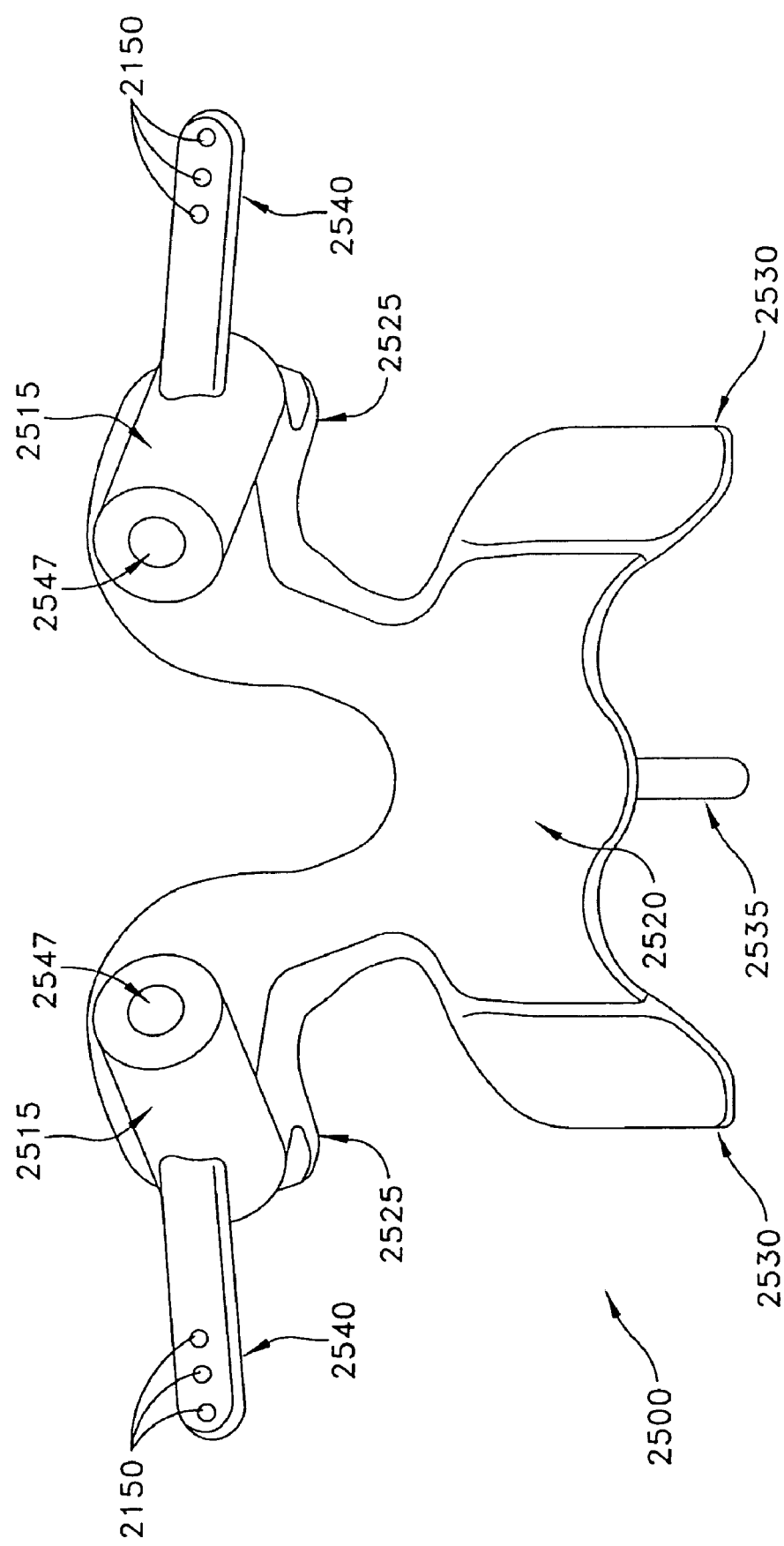
FIG. 47 is an anterior view of the prosthesis shown in FIG. 45.

Looking next at FIGS. 45-47, there is shown a novel prosthesis 2500 which is adapted to replace a pair of natural pedicles 2015, the natural lamina 2020, the two natural superior facets 2025, the two natural inferior facets 2030, the natural spinous process 2035, and the two natural transverse processes 2040. To this end, prosthesis 2500 comprises a pair of prosthetic pedicles 2515, a prosthetic lamina 2520 extending from prosthetic pedicles 2515, a pair of prosthetic superior facets 2525 extending from prosthetic pedicles 2515 and prosthetic lamina 2520, a pair of prosthetic inferior facets 2530 extending from prosthetic lamina 2520, a prosthetic spinous process 2535 extending from prosthetic lamina 2520, and a pair of prosthetic transverse processes 2540 extending from prosthetic pedicles 2515.

Figure 48:
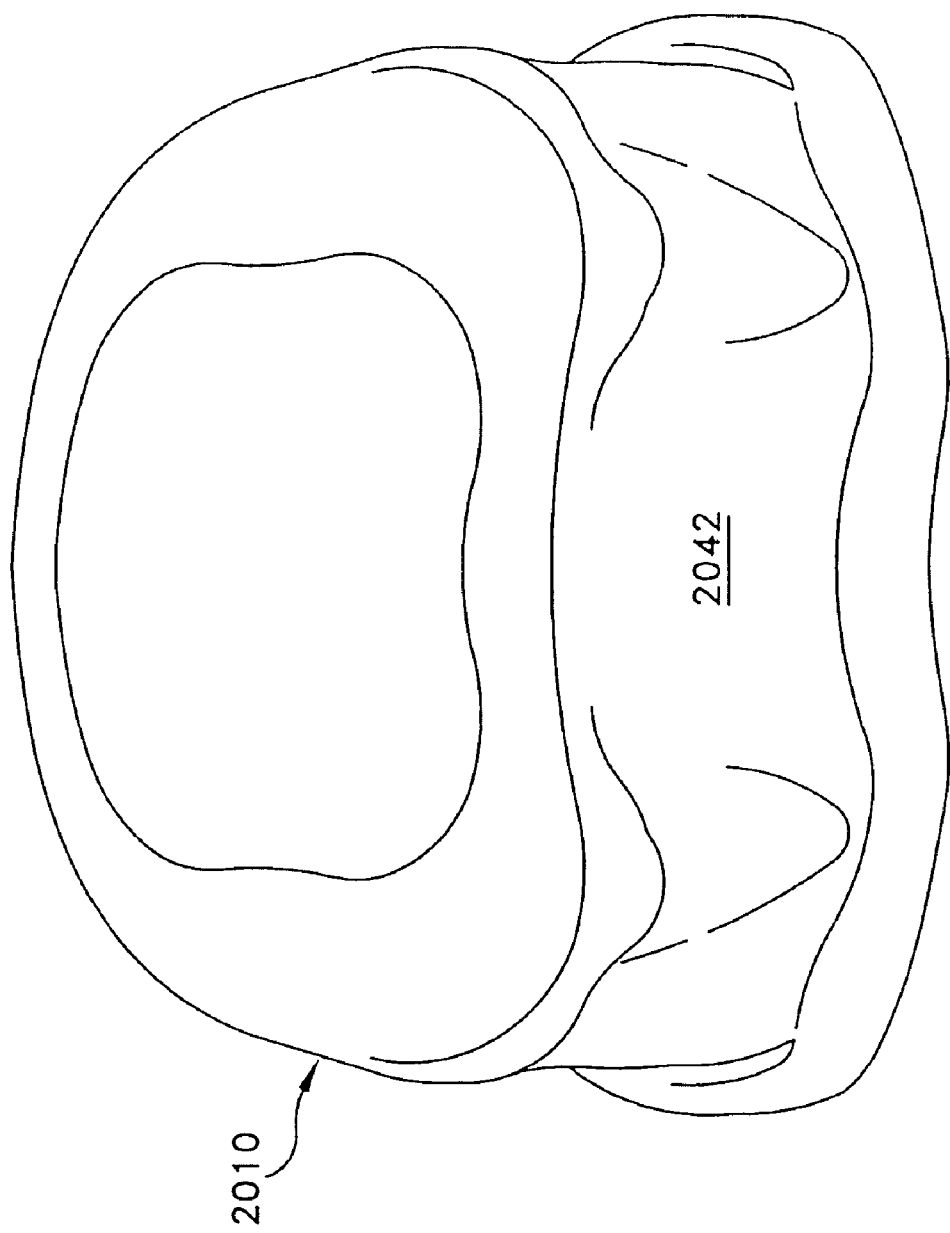
FIG. 48 is a perspective view of a vertebra which has been resected to receive the prosthesis shown in FIG. 45.
Figure 49:
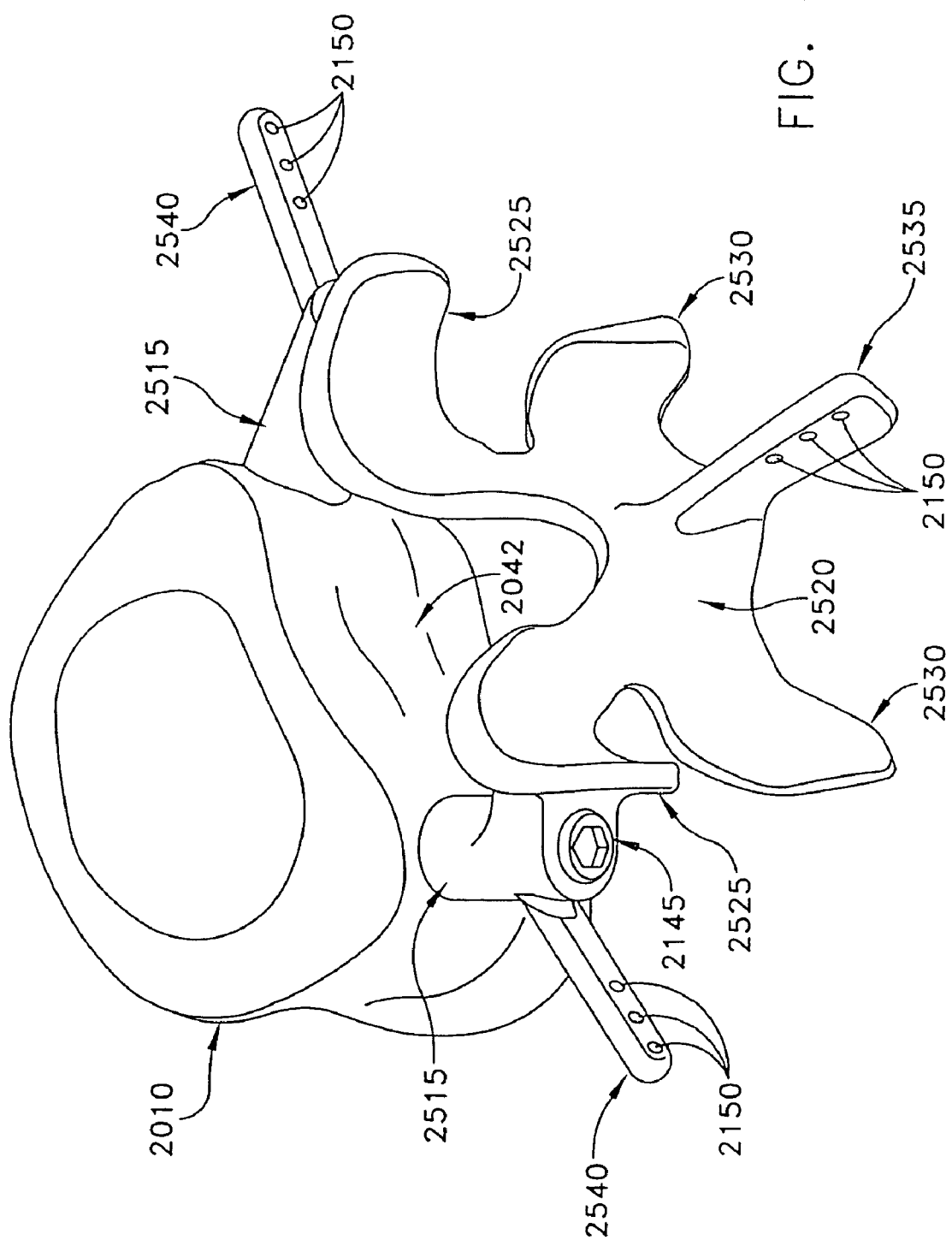
FIG. 49 is a perspective view showing the prosthesis of FIG. 45 mounted to the resected vertebra shown in FIG. 48.

In the use of prosthesis 2500, natural lumbar vertebra 2005 is resected at the bases of natural pedicles 2015 so as to remove to two natural pedicles 2015, the natural lamina 2020, the two natural superior facets 2025, the two natural inferior facets 2030, the natural spinous process 2035, and the two natural transverse processes 2040, leaving a vertebral body end face 2042 (FIG. 48). Then the prosthesis 2500 may be attached to the natural vertebral body 2010, e.g., by placing prosthetic pedicles 2515 against vertebral body end face 2042 and then passing screws 2145 through holes 2547 and into natural vertebral body 2010, as shown in FIG. 49. As seen in the drawings, the relative size, shape and positioning of the two prosthetic pedicles 2515, the prosthetic lamina 2520, the two prosthetic superior facets 2525, the two prosthetic inferior facets 2530, the prosthetic spinous process 2535, and the two prosthetic transverse processes 2540 essentially mimic the relative size, shape and positioning of the two natural pedicles 2015, the natural lamina 2020, the two natural superior facets 2025, the two natural inferior facets 2030, the natural spinous process 2035, and the two natural transverse processes 2040, whereby to effectively restore the vertebra. If desired, holes 2150 may be provided in prosthetic spinous process 2535 and the two prosthetic transverse processes 2540 so as to facilitate re-attaching soft tissue to these structures.

Figure 50:
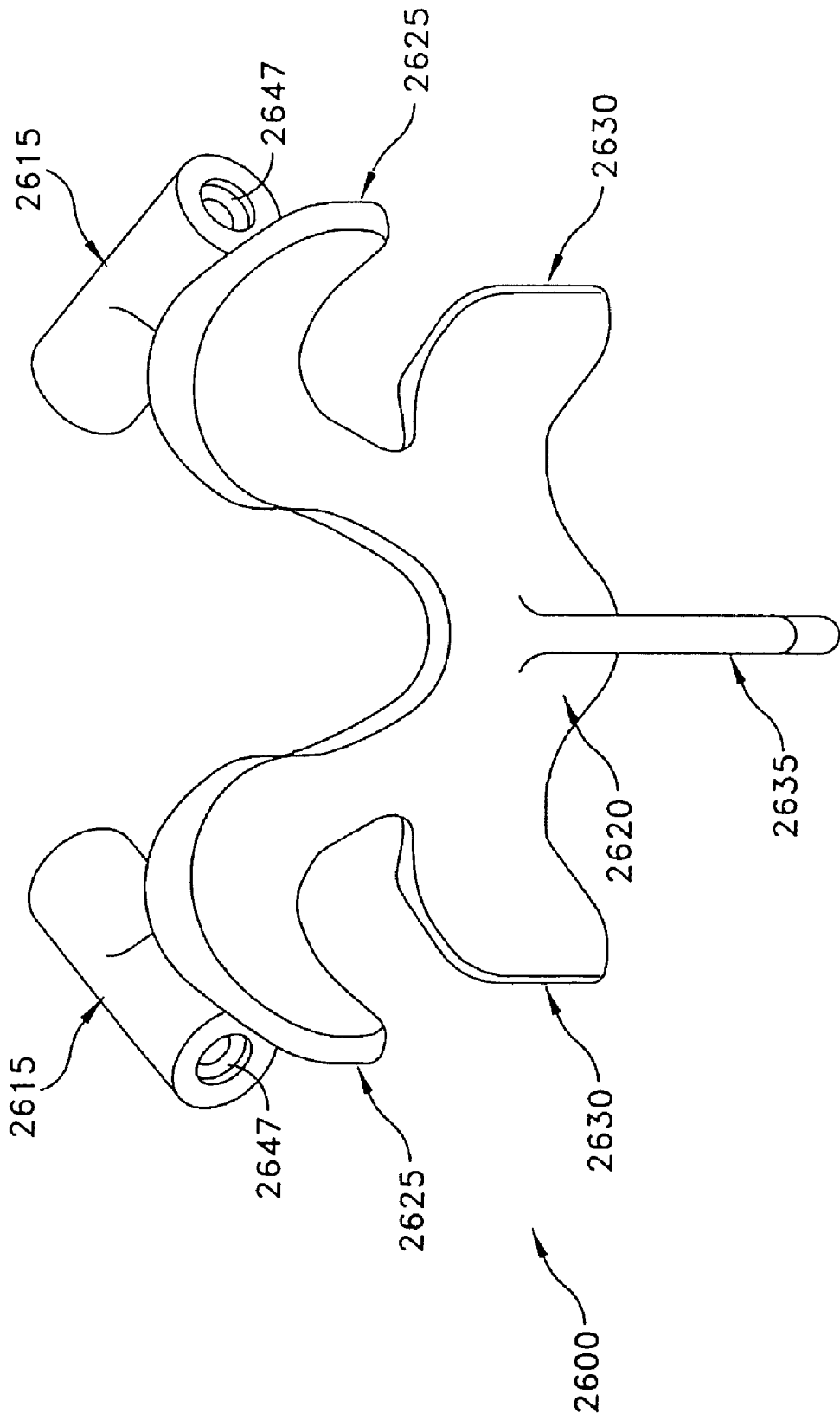
FIG. 50 is a perspective view of a novel prosthesis that replaces the two pedicles, the lamina, the four facets and the spinous process of a vertebra.

Looking next at FIG. 50, there is shown a novel prosthesis 2600 which is adapted to replace the two natural pedicles 2015, the natural lamina 2020, the two natural superior facets 2025, the two natural inferior facets 2030, and the natural spinous process 2035. To this end, prosthesis 2600 comprises a pair of prosthetic pedicles 2615, a prosthetic lamina 2620 extending from prosthetic pedicles 2615, a pair of prosthetic superior facets 2625 extending from prosthetic pedicles 2615 and prosthetic lamina 2620, a pair of prosthetic inferior facets 2630 extending from prosthetic lamina 2620, and a prosthetic spinous process 2635 extending from prosthetic lamina 2620.

In the use of prosthesis 2600, natural lumbar vertebra 2005 is resected at the bases of natural pedicles 2015 so as to remove the two natural pedicles 2015, the natural lamina 2020, the two natural superior facets 2025, the two natural inferior facets 2030, the natural spinous process 2035 and the two natural transverse processes 2040, leaving a vertebral body end face 2042 (FIG. 48). Then the prosthesis 2600 may be attached to the natural vertebral body 2010, e.g., by placing prosthetic pedicles 2615 against vertebral body end face 2042 and then passing screws 2145 through holes 2647 and into natural vertebral body 2010. As seen in the drawing, the relative size, shape and positioning of the two prosthetic pedicles 2615, the prosthetic lamina 2620, the two prosthetic superior facets 2625, the two prosthetic inferior facets 2630, and the prosthetic spinous process 2635 essentially mimic the relative size, shape and positioning of the two natural pedicles 2015, the natural lamina 2020, the two natural superior facets 2025, the two natural inferior facets 2030, and the natural spinous process 2035, whereby to effectively restore the vertebra. If desired, holes 2150 may be provided in prosthetic spinous process 2635 so as to facilitate re-attaching soft tissue to this structure.

Figure 51:
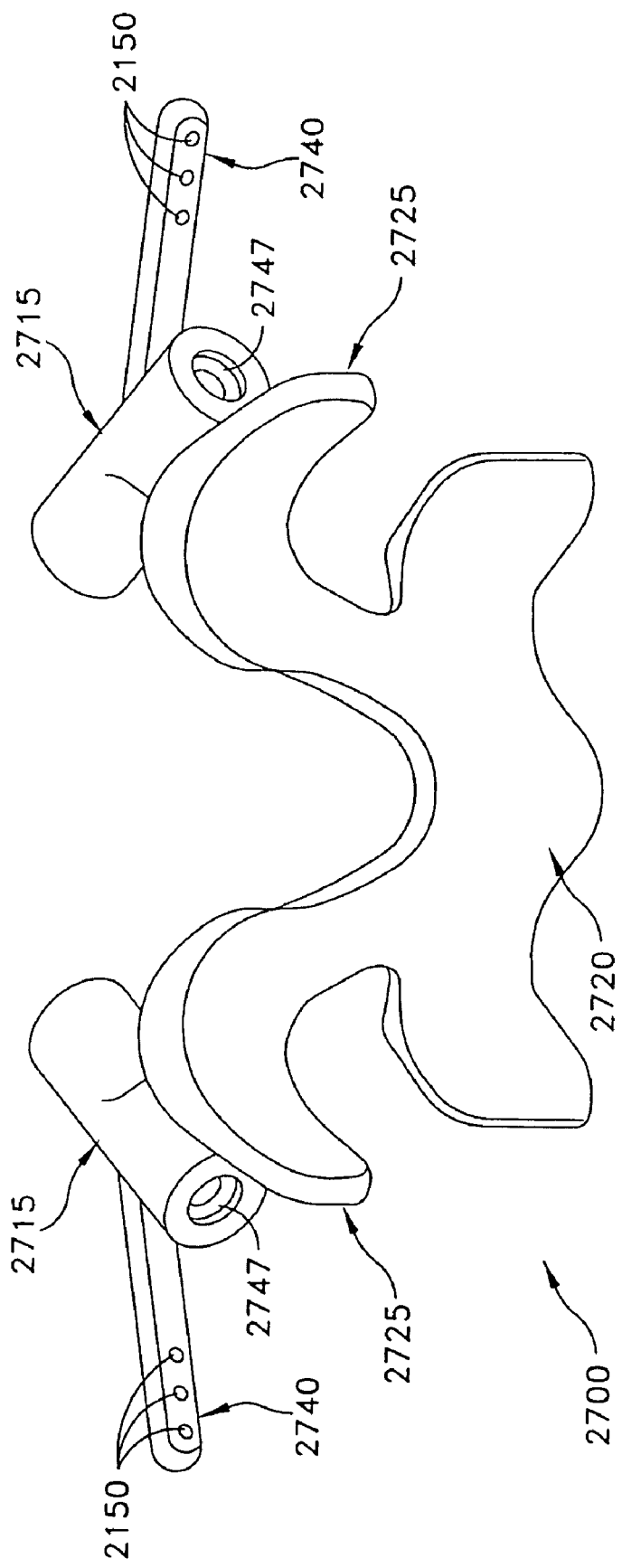
FIG. 51 is a perspective view of a novel prosthesis that replaces the two pedicles, the lamina, the four facets and the two transverse processes of a vertebra.

Looking next at FIG. 51, there is shown a novel prosthesis 2700 which is adapted to replace the two natural pedicles 2015, the natural lamina 2020, the two natural superior facets 2025, the two natural inferior facets 2030, and the two natural transverse processes 2040. To this end, prosthesis 2700 comprises a pair of prosthetic pedicles 2715, a prosthetic lamina 2720 extending from prosthetic pedicles 2715, a pair of prosthetic superior facets 2725 extending from prosthetic pedicles 2715 and prosthetic lamina 2720, a pair of prosthetic inferior facets 2730 extending from prosthetic lamina 2720, and a pair of prosthetic transverse processes 2740 extending from prosthetic pedicles 2715.

In the use of prosthesis 2700, natural lumbar vertebra 2005 is resected at the bases of natural pedicles 2015 so as to remove the two natural pedicles 2015, the natural lamina 2020, the two natural superior facets 2025, the two natural inferior facets 2030, the natural spinous process 2035, and the two natural transverse processes 2040, leaving a vertebral body end face 2042 (FIG. 48). Then the prosthesis 2700 may be attached to the natural vertebral body 2010, e.g., by placing prosthetic pedicles 2715 against vertebral body end face 2042 and then passing screws 2145 through holes 2747 and into vertebral body 2010. As seen in the drawing, the relative size, shape and positioning of the two prosthetic pedicles 2715, the prosthetic lamina 2720, the two prosthetic superior facets 2725, the two prosthetic inferior facets 2730, and the two prosthetic transverse processes 2740 essentially mimic the relative size, shape and positioning of the two natural pedicles 2015, the natural lamina 2020, the two natural superior facets 2025, the two natural inferior facets 2030, and the two natural transverse processes 2040, whereby to effectively restore the vertebra. If desired, holes 2150 may be provided in the two prosthetic transverse processes 2740 so as to facilitate re-attaching soft tissue to these structures.

Figure 52:
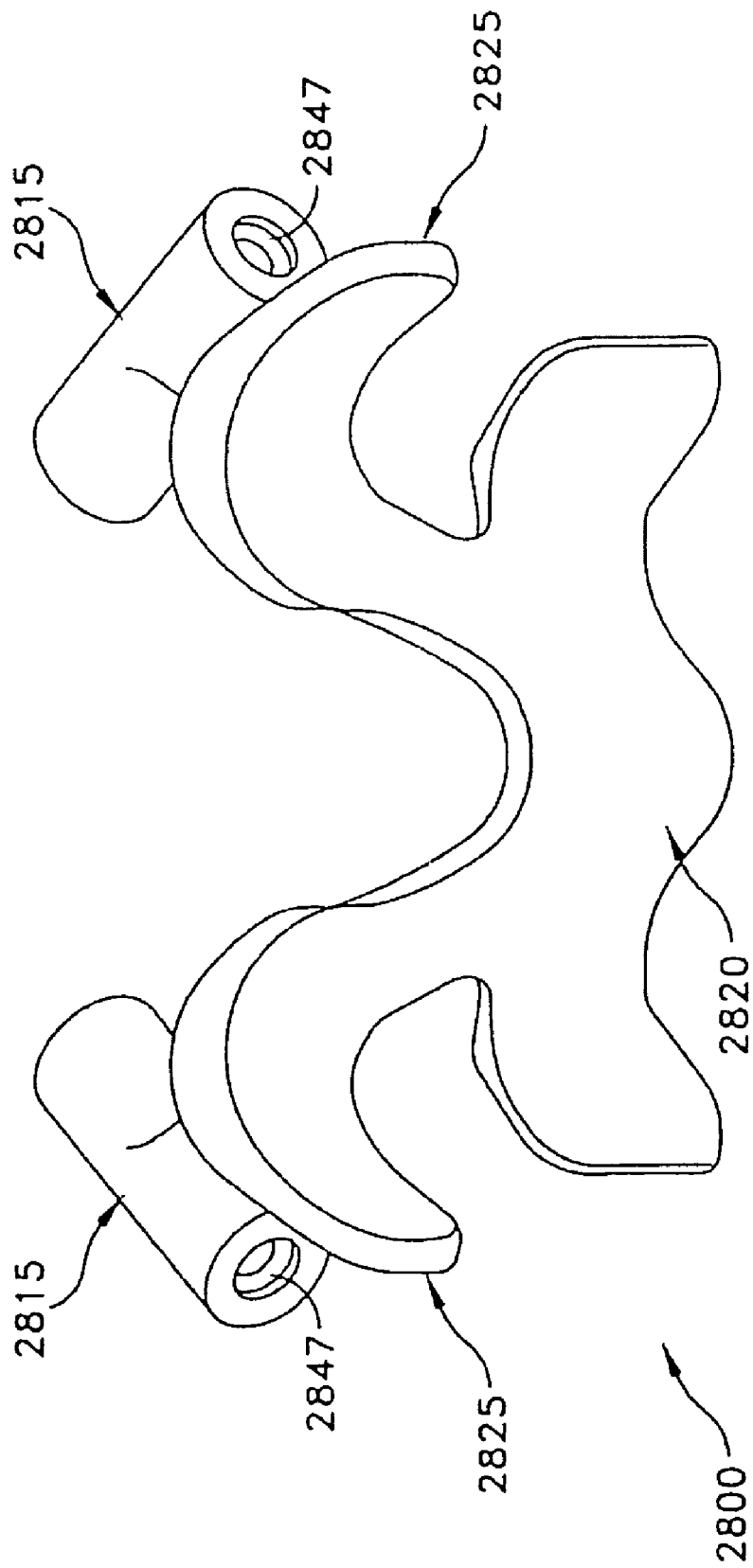
FIG. 52 is a perspective view of a novel prosthesis that replaces the two pedicles, the lamina and the four facets of a vertebra.

Looking next at FIG. 52, there is shown a novel prosthesis 2800 which is adapted to replace the two natural pedicles 2015, the natural lamina 2020, the two natural superior facets 2025, and the two natural inferior facets 2030. To this end, prosthesis 2800 comprises a pair of prosthetic pedicles 2815, a prosthetic lamina 2820 extending from prosthetic pedicles 2815, a pair of prosthetic superior facets 2825 extending from prosthetic pedicles 2815 and prosthetic lamina 2820, and a pair of prosthetic inferior facets 2830 extending from prosthetic lamina 2820.

In the use of prosthesis 2800, natural lumbar vertebra 2005 is resected at the bases of natural pedicles 2015 so as to remove the two natural pedicles 2015, the natural lamina 2020, the two natural superior facets 2025, the two natural inferior facets 2030, the natural spinous process 2035, and the two natural transverse processes 2040, leaving a vertebral body end face 2042 (FIG. 48). Then the prosthesis 2800 may be attached to natural vertebral body 2010, e.g., by placing prosthetic pedicles 2715 against vertebral body end face 2042 and then passing screws 2145 through holes 2847 and into natural vertebral body 2010. As seen in the drawing, the relative size, shape and positioning of the two prosthetic pedicles 2815, the prosthetic lamina 2820, the two prosthetic superior facets 2825, and the two prosthetic inferior facets 2830 essentially mimic the relative size, shape and positioning of the two natural pedicles 2015, the natural lamina 2020, the two natural superior facets 2025, and the two natural inferior facets 2030, whereby to effectively restore the vertebra.

It should also be appreciated that prostheses 2100, 2200, 2300, 2400, 2500, 2600, 2700 and 2800 may be attached to natural vertebra 2005 with apparatus other than the screws 2145 discussed above. Thus, for example, prostheses 2100, 2200, 2300, 2400, 2500, 2600, 2700 and 2800 may be attached to natural vertebra 2005 with rods or posts, etc. See, for example, FIG. 53, where prosthesis 2500 is shown attached to natural vertebra 2005 with rods 2146 which pass through, and snap into engagement with, prosthetic pedicles 2515.

Having thus described preferred embodiments of the invention with reference to the accompanying drawings, it is to be understood that the embodiments shown herein are provided by way of example only, and that various changes and modifications may be effected by one skilled in the art without departing from the scope or spirit of the invention as defined in the claims.

The invention claimed is:

1. A spinal joint kit for replacement of a portion of a mammalian spine comprising a spinal motion segment comprising an intervertebral disc between two consecutive vertebrae, the kit comprising:
    an artificial disc adapted to be incorporated into the spinal motion segment, the artificial disc comprising opposing end plates, wherein the end plates are movable relative to each other; and
    a prosthesis, wherein the prosthesis is discrete from the artificial disc and is adapted to be incorporated into the spinal motion segment, the prosthesis comprising an articular surface that replicates a natural articular surface of a vertebral facet;
    wherein, when the artificial disc and the prosthesis are operatively connected to the spinal motion segment, the artificial disc restores articulation between vertebral bodies of the vertebrae, the prosthesis articulates with another facet, no portion of the prosthesis contacts a posterior arch of the vertebrae, and the artificial disc and the prosthesis cooperate to restore natural biomechanics of the spinal motion segment.

2. The kit of claim 1, wherein the artificial disc comprises articulating structure disposed between the end plates.

3. The kit of claim 2, wherein the articulating structure comprises a rounded recess in a first of the end plates and a rounded protrusion extending from a second of the end plates and engaged in the recess.

4. The kit of claim 1, wherein the artificial disc comprises a deformable structure disposed between the end plates, wherein the deformable structure is selected from the group consisting of an elastomeric body and a polymer body.

5. The kit of claim 1, wherein the prosthesis comprises:
a fixation portion that is implantable into an interior bone space of the vertebrae, the articular surface being connected to the fixation portion.

6. The kit of claim 5, wherein the fixation portion is adapted to be fitted into an interior bone space of a pedicle.

7. The kit of claim 1, wherein the prosthesis comprises:
a bone-contacting surface that contacts one of an exterior surface of the vertebrae and a resected surface of the vertebrae, the articular surface being connected to the bone-contacting surface; and
a fixation element that attaches the bone-contacting surface to the vertebra.

8. A spinal joint kit for replacement of a portion of a mammalian spine comprising a spinal motion segment comprising an intervertebral disc between two consecutive vertebrae, the kit comprising:
an artificial disc adapted to be incorporated into the spinal motion segment, the artificial disc comprising opposing end plates, wherein the end plates are movable relative to each other;
a first prosthesis, wherein the first prosthesis is configured to replace at least one superior facet of an inferior one of the vertebrae and is adapted to be incorporated into the spinal motion segment, the first prosthesis comprising a first articular surface that replicates a natural articular surface of a superior facet; and
a second prosthesis, wherein the second prosthesis is configured to replace at least one inferior facet of a superior one of the vertebrae and is adapted to be incorporated into the spinal motion segment, the second prosthesis comprising a second articular surface that replicates a natural articular surface of an inferior facet, the inferior facet forming a joint with the superior facet;
wherein, when the artificial disc and the first and second prostheses are operatively connected to the spinal motion segment, the artificial disc restores articulation between vertebral bodies of the vertebrae, the first prosthesis articulates with the second prosthesis, no portion of the first and second prostheses contacts a posterior arch of the vertebrae, and the artificial disc and the first and second prostheses cooperate to restore natural biomechanics of the spinal motion segment.

9. The kit of claim 8, wherein the artificial disc comprises articulating structure disposed between the end plates.

10. The kit of claim 9, wherein the articulating structure comprises a rounded recess in a first of the end plates and a rounded protrusion extending from a second of the end plates and engaged in the recess.

11. The kit of claim 8, wherein the artificial disc comprises a deformable structure disposed between the end plates, wherein the deformable structure is selected from the group consisting of an elastomeric body and a polymer body.

12. The kit of claim 8, wherein the prosthesis is substantially duplicative of at least a portion of a facet of the vertebra.

13. The kit of claim 8, wherein the first prosthesis comprises:
a first fixation portion that is implantable into an interior bone space of the first vertebra, the first articular surface being connected to the first fixation portion;
wherein the second prosthesis comprises:
a second fixation portion that is implantable into an interior bone of the second vertebra, the second articular surface being connected to the second fixation portion.

14. The kit of claim 13, wherein each of the first and second fixation portions is adapted to be fitted into an interior bone space of a pedicle.

15. The kit of claim 8, wherein the first prosthesis comprises:
a first bone-contacting surface that contacts one of an exterior surface of the first vertebra and a resected surface of the first vertebra, the first articular surface being connected to the first bone-contacting surface; and
a first fixation element that attaches the first bone-contacting surface to the first vertebra;
wherein the first prosthesis is configured so that no portion of the first prosthesis contacts a posterior arch of the first vertebra;
wherein the second prosthesis comprises:
a first bone-contacting surface that contacts one of an exterior surface of the first vertebra and a resected surface of the first vertebra, the first articular surface being connected to the first bone-contacting surface; and
a first fixation element that attaches the first bone-contacting surface to the first vertebra;
wherein the first prosthesis is configured so that no portion of the first prosthesis contacts a posterior arch of the first vertebra.

* * * * *